United States Patent
Sahin et al.

(10) Patent No.: US 10,604,568 B2
(45) Date of Patent: Mar. 31, 2020

(54) DIAGNOSIS AND THERAPY OF CANCER INVOLVING CANCER STEM CELLS

(71) Applicants: BioNTech AG, Mainz (DE); Astellas Pharma Inc., Tokyo (JP); TRON-TRANSLATIONALE ONKOLOGIE AN DER UNIVERSITÄTSMEDIZIN JOHANNES GUTENBERG-UNIVERSITÄT MAINZ GEMEINNÜTZIGE GMBH, Mainz (DE)

(72) Inventors: Ugur Sahin, Mainz (DE); Ozlem Tureci, Mainz (DE); Korden Walter, Mainz (DE); Meike Wagner, Mainz (DE); Maria Kreuzberg, Mainz (DE); Sabine Hacker, Mainz (DE); Stefan Jacobs, Mainz-Kastel (DE)

(73) Assignees: BioN Tech AG, Mainz (DE); TRON-TRANSLATIONALE ONKOLOGIE AN DER UNIVERSITÄTSMEDIZIN DER JOHANNES GUTENBERG-UNIVERSITÄT MAINZ GEMEINNÜTZIGE GMBH, Mainz (DE); Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/904,011

(22) PCT Filed: Jul. 30, 2014

(86) PCT No.: PCT/EP2014/066330
§ 371 (c)(1),
(2) Date: Jan. 8, 2016

(87) PCT Pub. No.: WO2015/014870
PCT Pub. Date: Feb. 5, 2015

(65) Prior Publication Data
US 2016/0159901 A1    Jun. 9, 2016

(30) Foreign Application Priority Data
Jul. 31, 2013 (WO) ................ PCT/EP2013/002272

(51) Int. Cl.
| | | |
|---|---|---|
| *A61K 39/395* | (2006.01) |
| *A61K 47/68* | (2017.01) |
| *A61K 31/337* | (2006.01) |
| *A61K 31/5365* | (2006.01) |
| *A61K 31/7048* | (2006.01) |
| *A61K 31/7064* | (2006.01) |
| *C07K 16/28* | (2006.01) |
| *G01N 33/574* | (2006.01) |
| *A61K 33/24* | (2019.01) |
| *A61N 5/10* | (2006.01) |
| *C07K 16/30* | (2006.01) |
| *A61K 39/00* | (2006.01) |

(52) U.S. Cl.
CPC .......... *C07K 16/28* (2013.01); *A61K 31/337* (2013.01); *A61K 31/5365* (2013.01); *A61K 31/7048* (2013.01); *A61K 31/7064* (2013.01); *A61K 33/24* (2013.01); *A61K 39/39558* (2013.01); *A61K 47/6851* (2017.08); *A61N 5/10* (2013.01); *C07K 16/30* (2013.01); *G01N 33/57484* (2013.01); *G01N 33/57492* (2013.01); *A61K 2039/505* (2013.01); *C07K 2317/56* (2013.01); *C07K 2317/73* (2013.01); *C07K 2317/732* (2013.01); *C07K 2317/76* (2013.01); *G01N 2333/705* (2013.01); *G01N 2800/52* (2013.01)

(58) Field of Classification Search
CPC .................. A61K 39/395; A61K 2039/505
See application file for complete search history.

(56) References Cited

U.S. PATENT DOCUMENTS

| | | | |
|---|---|---|---|
| 4,946,778 | A | 8/1990 | Ladner et al. |
| 5,624,821 | A | 4/1997 | Winter et al. |
| 5,648,260 | A | 7/1997 | Winter et al. |
| 6,121,022 | A | 9/2000 | Presta et al. |
| 6,194,551 | B1 | 2/2001 | Idusogie et al. |
| 6,277,375 | B1 | 8/2001 | Ward |
| 7,431,927 | B2 | 10/2008 | Couto et al. |
| 9,321,842 | B2 | 4/2016 | Sahin et al. |
| 9,487,584 | B2 | 11/2016 | Sahin et al. |
| 9,718,886 | B2 | 8/2017 | Sahin et al. |
| 2002/0086356 | A1 | 7/2002 | Tuschl et al. |
| 2002/0127584 | A1 | 9/2002 | Baker et al. |
| 2003/0017534 | A1 | 1/2003 | Buelow et al. |
| 2003/0036635 | A1 | 2/2003 | Baker et al. |
| 2003/0118592 | A1 | 6/2003 | Ledbetter et al. |
| 2003/0133939 | A1 | 7/2003 | Ledbetter et al. |

(Continued)

FOREIGN PATENT DOCUMENTS

| | | |
|---|---|---|
| CA | 2379661 | 9/2003 |
| CN | 101312989 | 11/2008 |

(Continued)

OTHER PUBLICATIONS

Paul, Fundamental Immunology, 3rd Edition, 1993, pp. 292-295.*

(Continued)

*Primary Examiner* — Hong Sang
(74) *Attorney, Agent, or Firm* — McAndrews, Held & Malloy, Ltd.

(57) ABSTRACT

The present invention provides methods for diagnosis or treatment of cancer diseases involving cancer stem cells comprising targeting CLDN6. In particular, the present invention provides a method of determining cancer stem cells comprising detecting cells expressing CLDN6. Furthermore, the present invention provides a method of treating or preventing cancer comprising inhibiting and/or eliminating cancer stem cells by administering an antibody having the ability of binding to CLDN6 to a cancer patient.

10 Claims, 34 Drawing Sheets
Specification includes a Sequence Listing.

(56) References Cited

U.S. PATENT DOCUMENTS

| | | |
|---|---|---|
| 2007/0082345 A1 | 4/2007 | Ota et al. |
| 2007/0207142 A1* | 9/2007 | Crowley .............. C07K 14/705 424/133.1 |
| 2011/0044894 A1* | 2/2011 | Karsunky .............. C07K 16/28 424/1.11 |
| 2011/0059469 A1 | 3/2011 | Aburatani |
| 2011/0300144 A1 | 12/2011 | Sahin et al. |
| 2012/0308478 A1 | 12/2012 | Sahin et al. |
| 2013/0183305 A1 | 7/2013 | Sahin et al. |
| 2014/0127219 A1 | 5/2014 | Sahin et al. |
| 2016/0222125 A1 | 8/2016 | Sahin et al. |
| 2016/0264677 A1 | 9/2016 | Sahin et al. |
| 2016/0355604 A1 | 12/2016 | Sahin et al. |
| 2018/0119146 A1 | 5/2018 | Sahin et al. |
| 2018/0142033 A1 | 5/2018 | Sahin et al. |
| 2018/0162938 A1 | 6/2018 | Sahin et al. |

FOREIGN PATENT DOCUMENTS

| | | |
|---|---|---|
| CN | 101687929 | 3/2010 |
| EP | 0338841 | 10/1989 |
| EP | 1067182 | 1/2001 |
| EP | 2011886 | 1/2009 |
| EP | 2241578 | 10/2010 |
| EP | 2322555 | 5/2011 |
| JP | H11503014 | 3/1999 |
| JP | 2001506275 | 5/2001 |
| JP | 2002-536995 | 11/2002 |
| JP | 2004-537534 | 12/2004 |
| JP | 2007-529416 | 10/2007 |
| JP | 2010178650 | 8/2010 |
| JP | 2011-501758 | 1/2011 |
| JP | 2011-516580 | 5/2011 |
| JP | 2012-512778 | 6/2012 |
| JP | 2012-518608 | 8/2012 |
| JP | 2012-518609 | 8/2012 |
| RU | 2010133547 | 2/2012 |
| WO | 87/04462 | 7/1987 |
| WO | 89/01036 | 2/1989 |
| WO | 92/04381 | 3/1992 |
| WO | 96/33265 | 10/1996 |
| WO | 96/33739 | 10/1996 |
| WO | 99/24463 | 5/1999 |
| WO | 99/45962 | 9/1999 |
| WO | 00/12708 | 3/2000 |
| WO | 2000/26360 | 5/2000 |
| WO | 00/35937 | 6/2000 |
| WO | 00/73348 | 12/2000 |
| WO | 00/78961 | 12/2000 |
| WO | 01/51513 | 7/2001 |
| WO | 01/53312 | 7/2001 |
| WO | 01/93983 | 12/2001 |
| WO | 02/00690 | 1/2002 |
| WO | 02/08284 | 1/2002 |
| WO | 02/08288 | 1/2002 |
| WO | 02/43478 | 6/2002 |
| WO | 03/088808 | 10/2003 |
| WO | 2004/030615 | 4/2004 |
| WO | 2004/035607 | 4/2004 |
| WO | 2004/060270 | 7/2004 |
| WO | 2004110363 | 12/2004 |
| WO | 2005/005601 | 1/2005 |
| WO | 2006/033664 | 3/2006 |
| WO | 2008/114733 | 9/2008 |
| WO | 2009/025759 | 2/2009 |
| WO | 2009/028663 | 3/2009 |
| WO | 2009/087978 | 7/2009 |
| WO | 2010043650 | 4/2010 |
| WO | 2010/094499 | 8/2010 |
| WO | 2011057788 | 5/2011 |
| WO | 2011105551 | 9/2011 |
| WO | 2012003956 | 1/2012 |
| WO | WO 2012156018 A1 * | 11/2012 .............. C07K 16/28 |
| WO | 2013035824 | 3/2013 |
| WO | 2013/087929 | 6/2013 |
| WO | 2014/015148 | 1/2014 |

OTHER PUBLICATIONS

Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Cancer information from National Institute of Cancer, Apr. 29, 2010, pp. 1-2.*
Vogelstein et al., Nature Medicine, 2004, 10(8): 789-799.*
International Search Report of PCT/EP2014/066330 dated Nov. 17, 2014.
T. Ushiku et al., "Distinct Expression Pattern of Claudin-6, a Primitive Phenotypic Tight Junction Molecule, in Germ Cell Tumours and Visceral Carcinomas", Histopathology, vol. 61, No. 6, Jul. 17, 2012, XP055107355, pp. 1043-1056.
U. David et al., "Immunoligic and Chemical Targeting of the Tight-Junction Protein Claudin-6 Eliminates Tumorigenic Human Pluripotent Stem Cells", Natural Communications 2013, vol. 4, Jun. 18, 2013, XP008168176, p. 1992.
W. Dormeyer et al., "Plasma Membrane Proteomics of Human Embryonic Stem Cells and Human Embroyonal Carcinoma Cells", Journal of Proteome Research, American Chemical Society, Washington, DC., US, vol. 7, XP002599270, Jul. 3, 2008, pp. 2936-2951.
P. Trail, "Antibody Drug Conjugates as Cancer Therapeutics", Antibodies, M D P I AG, CH, vol. 2, No. 1, Feb. 27, 2013, XP002725437, pp. 113-129.
M. Kwon, "Emerging Roles of Claudins in Human Cancer", International Journal of Molecular Science, vol. 14, No. 9, Sep. 4, 2013, XP0055107170, pp. 18148-18180.
K. Turksen, "Claudins and Cancer Stem Cells", Stem Cell Reviews and Reports, Humana Press Inc., New York, vol. 7, No. 4, Apr. 28, 2011, XP019985913, pp. 797-798.
A. Prat et al, "Phenotypic and Molecular Characterization of the Claudin-Low Intrinsic Subtype of Breast Cancer", Breast Cancer Research, Current Science, London, GB, vol. 12, No. 5, Sep. 2, 2010, XP021085380, p. R68.
L. Wang et al, "Claudin 6: A Novel Surface Marker for Characterizing Mouse Pluripotent Stem Cells", Cell Research, vol. 22, No. 6, May 8, 2012, XP055107350, pp. 1082-1085.
Allard et al, Clin Cancer Res 10: 6897-904, 2004.
Altman et al., Science 274:94-96, 1996.
Anonymous: "Tumor Markers—National Cancer Institute", Dec. 7, 2011 (Dec. 7, 2011), Retrieved from the Internet: URL:http://www.cancer.gov/cancertopics/diagnosis-staging/diagnosis/tumor-markers-fact-sheet [retrieved on Mar. 20, 2015].
Beadling et al. Nature Medicine 12:1208 (2006).
Kuby, Janis Immunology, W. H. Freeman and Company New York, NY (1992).
Ming-Ming Tsai: "Potential prognostic, diagnostic and therapeutic markers for human gastric cancer", World Journal of Gastroenterology, vol. 20, No. 38, Oct. 14, 2014 (Oct. 14, 2014), p. 13791.
NCBI, *Homo sapiens* claudin 6 (CLDN6, mRNA, May 1, 2015, 4 pages.
Tuschl T. et al., "The siRNA User Guide", revised Oct. 11, 2002.
Vajdos F. F. et al., Comprehensive Functional Maps of the Antigenbinding Site of an Anti-ErbB2 Antibody Obtained with Shotgun Scanning Mutagenesis, J. Mol. Biol., 2002, vol. 320, pp. 415-428.
Yuan et al. (Cytotherapy 8:498, 2006).
Adams, G.P. et al., Cancer Res., (2001), vol. 61, pp. 4750-4755.
K. Fujimori et al., J. Nucl. Med., 31: 1191-1198, 1990.
Sharon, J., Proc. Natl. Acad. Sci. USA, (1990), vol. 87, pp. 4814-4817.
Anderson et al., J. Immunol. 143: 1899-1904, 198.
Casset et al. (Biochemical and Biophysical Research Communications, 2003, 307:198-205).
Chen et al. (Journal of Molecular Biology, 1999, 293:865-881).

(56) References Cited

OTHER PUBLICATIONS

Clark, W.R. (1986), The Experimental Foundations of Modern Immunology.
Cristofanilli et al, N Eng.J Med 351: 781-91,2004.
Dunbar et al., Curro Biol. 8:413-416, 1998.
European Search Report corresponding to European Patent Application Serial No. 09014136.7 dated Mar. 23, 2010.
Extended European Search Report for 10006957.4-2406 dated Nov. 10, 2010.
Extended European Search Report for European Patent Application No. 09002452.2-1212, dated Oct. 22, 2009.
Gardsvoll, J. Immunol. Methods 234: 107-116, 2000.
GenBank. *Homo sapiens* claudin 6 (CLDN6), mRNA NCB | Reference Sequence: NM_021195.4, 2014.
Hall (1995) Science 268: 1432-1434.
Hewitt et al., "The claudin gene family: expression in normal and neoplastic tissdues." BMC Cancer, Biomed Central. vol. 6, No. 1, Jul. 12, 2006. XP021016181.
Hong Yeon-Hee et al., "Up-regulation of the claudin-6 gene in adipongenesis." Bioscience Biotechnology, and Biochemistry, Nov. 2005, vol. 69, No. 11, pp. 2117-2121, XP002547908.
Huang Yu-Hung et al., "Claudin-3 gene silencing with siRNA suppresses ovarian tumor growth and metastasis." Proceedings of the National Academy of Sciences of the United States of America 3, Mar. 2009, vol. 106, No. 9, Feb. 10, 2009, pp. 3426-3430, XP002547909.
Iacobuzio-Donahue et al. Amer. Journ. Pathology, vol. 160, No. 4, pp. 1239-1249, Apr. 2002.
ISR & WO for PCT/EP2011/003312, dated Oct. 5, 2011.
IPRP for PCT/EP2010/001062, dated Sep. 1, 2011.
IPRP for PCT/EP2010/006888 dated May 15, 2012.
ISR & WO for PCT/EP2010/006888, dated Feb. 4, 2011.
Kessels et al., Nat Immunol. 2:957-61, 2001.
Kraeft et al, Clin Cancer Res 10: 3020-8, 2004.
Lamminmaki et al. (Journal of Biological Chemistry, 2001, 276:36687-36694.
Lu et al (2004) Clinical Cancer Research vol. 10: 3291-3300.
Maloy et al., Proc Natl Acad Sci USA 98:3299-303,2001.
Morita et al., "Endothelial claudin: Claudin-5/TMVCF constitutes tight junction strands in endothelial cells." The Journal of Cell Biology, vol. 147, No. 1, Oct. 4, 1999, pp. 185-194, XP002239048.
Neefies et al., Nature Reviews, Immunology, vol. 11, pp. 823-836 (Dec. 2011).
Osanai Makoto et al., "Epigenetic silencing of claudin-6 promotes anchorage-independent growth of breast carcinoma cells." Cancer Science Oct. 2007, vol. 98, No. 10, pp. 1557-1562, XP002547907.
Ossendorp et al., Immunol Lett. 74:75-9, 2000.
Ossendorp et al., J. Exp. Med. 187:693-702, 1998.
Padlan et al. (Proceedings of the National Academy of Sciences, 1989, 86:5938-5942).
Pakula A. A. et al., Genetic analysis of protein stability and function. Annu. Rev. Genet., 1989 No. 23, pp. 289-310.
Pascalis et al. (The Journal of Immunology, 2002, 169, 2076-3084).
Reddehase et al., Nature vol. 337, pp. 651-653 (Feb. 1989).
Robinson, J.R., ed. Sustained and Controlled Release Drug Delivery Systems, Marcel Dekker, Inc., New York, 1978.
Roitt, I. (1991), Essential Immunology, 7th Edition, Blackwell Scientific Publications, Oxford.
Rudikoff et al. (Proceedings of the National Academy of Science USA, 1982, 79:1979).
Satohisa et al. (Experimental Cell Research, 2005: 310:66-78).
Science 268: 1432-1434, 1995, by Hall.
Smirnov et al, Cancer Res 65: 4993-7, 2005.
Stanislawski et al., Nat Immunol. 2:962-70, 2001.
International Preliminary Report on Patentability for International Patent Application No. PCT/EP2012/001721 dated Nov. 19, 2013.
Amon et al. Monoclonal Antibodies for Immunotargeting of Drugs in Cancer Therapy Resifeld et al. (eds.), pp. 243-256 (Alan R. Liss, Inc. 1985).
Babcock et al., Proc. Natl. Acad. Sci, USA, vol. 93, pp. 7843-7848, Jul. 1996; A novel strategy for generating monoclonal antibodies from single, isolated lymphocytes producing antibodies of defined strategy.
Baldwin et al. (eds.), pp. 303-316 Analysis, Results, and Future Prospective of the Therapeutic Use of Radiolabeled Antibody in Cancer Therapy, in Monoclonal Antibodies for Cancer Detection and Therapy, (Academic Press 1985).
Berge, S.M., et al. (1977) J. Pharm. Sci. 66:12-19.
Berzofsky et al., "Antibody-Antigen Interactions" in Fundamental Immunology, Paul, W. E., Ed., Raven Press New York, NY (1984), Kuby, Janis Immunology, W. H. Freeman and Company New York, N Y (1992).
Bird et al. (1988) Science 242: 423-426.
Cunningham-Rundles C, Zhuo Z, Griffith B, Keenan J. (1992) Biological activities of polyethylene-glycol immunoglobulin conjugates. Resistance to enzymatic degradation. 1. Immunol. Methods, 152: 177-190.
Fischer, R., et al. (1999) Biol. Chem. 380: 825-839.
Goodman and Gilman, "The Pharmacological Basis of Therapeutics", 8th Edition, 1990, McGraw-Hill, Inc., in particular Chapter 52 Antineoplastic Agents Paul Calabresi and Bruce A. Chabner.
Hellstrom et al., "Antibodies for Drug Delivery" in Controlled Drug Delivery (2nd Ed.), Robinson et al. (eds.), pp. 623-653 (Marcel Dekker, Inc. 1987).
Holliger, P., et al. (1993) Proc. Natl. Acad. Sci. USA 90: 6444-6448.
Huston et al. (1988) Proc. Natl. Acad. Sci. USA 85: 5879-5883.
Jones, P. et al. (1986) Nature 321: 522-525.
Kohler and Milstein, Nature 256: 495 (1975).
Kozak, 1991, J. Biol. Chem. 266: 19867-19870.
Krieg et al., Nature 374:546-9, 1995.
Landor M. (1995) Maternal-fetal transfer of immunoglobulins, Ann. Allergy Asthma Immunol. 74: 279-283.
Matz et al. (Nucleic Acids research, 1999 vol. 27, No. 6 1558-60.
Monteiro, R. C. et al. (1992) J. Immunol. 148: 1764).
Morrison, S. (1985) Science 229: 1202.
Morton, H.C. et al. (1996) Critical Reviews in Immunology 16: 423-440).
Neddleman and Wunsch, 1970, J. Mol. Biol. 48, 443.
Pearson and Lipman, 1988, Proc. Natl Acad. Sci. USA 85, 2444.
Poljak, R. J., et al. (1994) Structure 2: 1121-1123.
Pollock, et al. (1999) J. Immunol. Meth. 231: 147-157.
Queen, C. et al aL (1989) Proc. NatL Acad. Sci. U. S. A. 86: 10029-10033.
Remington: The Science and Practice of Pharmacy, 19th Edition, Gennaro, Ed., Mack Publishing Co., Easton, PA, 1995.
Riechmann, L. et al aL (1998) Nature 332: 323-327.
Rossi et al., Am. J. Clin. Pathol. 124: 295 (2005).
Sambrook et al., Molecular Cloning: A Laboratory Manual, 1. Editors, 2nd Edition, Cold Spring Harbor Laboratory Press, Cold Spring Harbor, New York, 1989 or Current Protocols in Molecular Biology, F.M. Ausubel et al., Editors, John Wiley & Sons, Inc., New York.
Scatchard et al., Ann N.Y. Acad. ScL, 51:660 (1949).
Shields et al. (2002) JBC, 277: 26733.
Smith and Waterman, 1981, Ads App. Math. 2, 482.
So et al., 1997, Mol. Cells 7: 178-186.
Spieker-Polet et al. Proc. Natl. Acad. Sci. U.S.A. 92:9348 (1995).
Strejan et al. (1984) J. Neuroimmunol. 7: 27.
Thorpe et al., "The Preparation and Cytotoxic Properties of Antibody-Toxin Conjugates" Immunol. Rev., 62: 119-58 (1982).
Thorpe, "Antibody Carriers of Cytotoxic Agents in Cancer Therapy: A Review" in Monoclonal Antibodies '84: Biological and Clinical Applications, Pinchera et al. (eds. ), pp. 475-506 (1985).
Verma, R., et al. (1998) J. Immunol. Meth. 216: 165-181.
Ward et al., (1989) Nature 341: 544-546.
Arabzadeh A et al: "Changes in the distribution pattern of claudin tight junction proteins during the progression of mouse skin tumorigenesis", BMC Cancer, Biomed Central, London, GB, vol. 7, Oct. 18, 2007 (Oct. 18, 2007), XP008139355, ISSN: 1471-2407, DOI: 10.1186/1471-2407-7-196.
Int'l Search Report for PCT/EP2012/001721, dated Jul. 25, 2012.

(56) References Cited

OTHER PUBLICATIONS

Benny K.C. Lo Antibody Engineering ISBN: 1-58829-092-1, Dec. 5, 2003.
Documentation of Affymetrix probe set "75948_AT", Oct. 2013.
Harlow et al. "Antibodies: A Laboratory Manual" ISBN: 0879693142, Dec. 1, 1988.
Harlow et al. "Using Antibodies: A Laboratory Manual: Portable Protocol NO" ISBN 0879695447, Mar. 1, 2000.
Koslowski et al, "The human X chromosome is enriched for germline genes expressed in premeiotic germ cells of both sexes", Human Molecular Genetics, vol. 15, No. 15, 2392-2399, Jun. 22, 2006.
Koslowski et al, "A Placenta-Specific Gene Ectopically Activated in Many Human Cancers Is Essentially Involved in Malignant Cell Processes", Cancer Res, 67: (19), 9528-9534, Oct. 1, 2007.
Merrifield, 1964.
Shepherd et al. "Monoclonal Antibodies: A Practical Approach" ISBN 0-19-963722-9, Jul. 13, 2000.
Kraus et al., in Methods in Molecular Biology series, "Recombinant Antibodies for Cancer Therapy: Methods and Protocols", ISBN-0-89603-918-8, Jul. 15, 2002.
Morris, Glenn E. "Epitope Mapping Protocols (Methods in Molecular Biology)" ISBN-089603-375-9, Aug. 1, 1996.
Westwood, et al. "Epitope Mapping: A Practical Approach" Practical Approach Series, Book 248, Mar. 15, 2001.
Almagro & Fransson, Frontiers in Bioscience 2008; 13:1619-33.
De Genst et al., Developmental and Comparative Immunology, 2006, 30:187-98.
Barthelemy et al., Journal of Biological Chemistry, 2008, 283:3639-3654.
Choi et al., 2011, Molecular BioSystems, 2011, 7:3327-334.
Griffiths et al., The EMBO Journal, 1993, 12:725-734.
Klimka et al., British Journal of Cancer, 2000, 83:252-260.
Beiboer et al., Journal of Molecular Biology, 2000, 296:833-849.
"Bunshi Saibo Seibutsugaku Jiten" (Molecular Cell Biology Dictionary), 1stEd., 2002, Tokyo Kagaku Dojin Co., Ltd., p. 282, definition of antigen binding site.
"Menekigaku Jiten" (Dictionary of Immunology), 2nd Ed., 2001, Tokyo Kagaku Dojin Co., Ltd., p. 501, definition of humanized antibody.
Brown, et al., "Tolerance to Single, but not Multiple, Amino Acid Replacements in Antibody VH CDR2," J. Immunol. May 1996; 156 (9):3285-91.
Vare, et al., "Twist is inversely associated with claudins in germ cell tumors of the testis," APMIS 118: 640-647, published online Jun. 11, 2010.
Mariuzza et al., "The Structural Basis of Antigen-Antibody Recognition", Ann. Rev. Biophys. Biophys. Chem. 1987, 16: 139-59.
Kohler, "Immunoglobulin chain loss in hybridoma lines," Proc. Natl. Acad. Sci. USA, vol. 77, No. 4 pp. 2197-2199, Apr. 1980.
Ozturk et al., "Loss of Antibody Productivity During Long-Term Cultivation of a Hybridoma Cell Line in Low Serum and Serum-Free Media," Hybridoma, vol. 9, No. 2, 1990.
Sela-Culang et al., "The structural basis of antibody-antigen recognition," Frontiers in Immunology, vol. 4, Article 302, Oct. 8, 2013.
Wu et al., "Humanization of a Murine Monoclonal Antibody by Simultaneous Optimization of Framework and CDR Residues," Journal of Molecular Biology, 294, 1999.
Xu et al. "Diversity in the CDR3 Region of VH is Sufficient for Most Antibody Specificities", Immunity, vol. 13, No. 1, Jul. 2000.
Arabzadeh et al. "Role of the Cldn6 Cytoplasmic Tail Domain in Membrane Targeting and Epidermal Differentiation in Vivo", Molecular and Cellular Biology, vol. 26(15), Aug. 2006.
GenBank: NP_ 067018.1, 2008.
Kang et al., "Studies on SP6 promoter using a new plasmid vector that allows gene insertion at the transcription initiation site", Nuc. Acids Res., 15, pp. 2279-2294, Mar. 1987.
Fuh et al., "Anti-CD22 and anti-CD79b antibody-drug conjugates preferentially target proliferating B cells", British Journal of Pharmacology (2017), 174, 628-640.
Shan et al., "Constitutive Endocytosis and Degradation of CD22 by Human B Cells'", The Journal of Immunology (1994), retrieved from the Internet on Oct. 6, 2018, 4466-4475.

\* cited by examiner

A

B

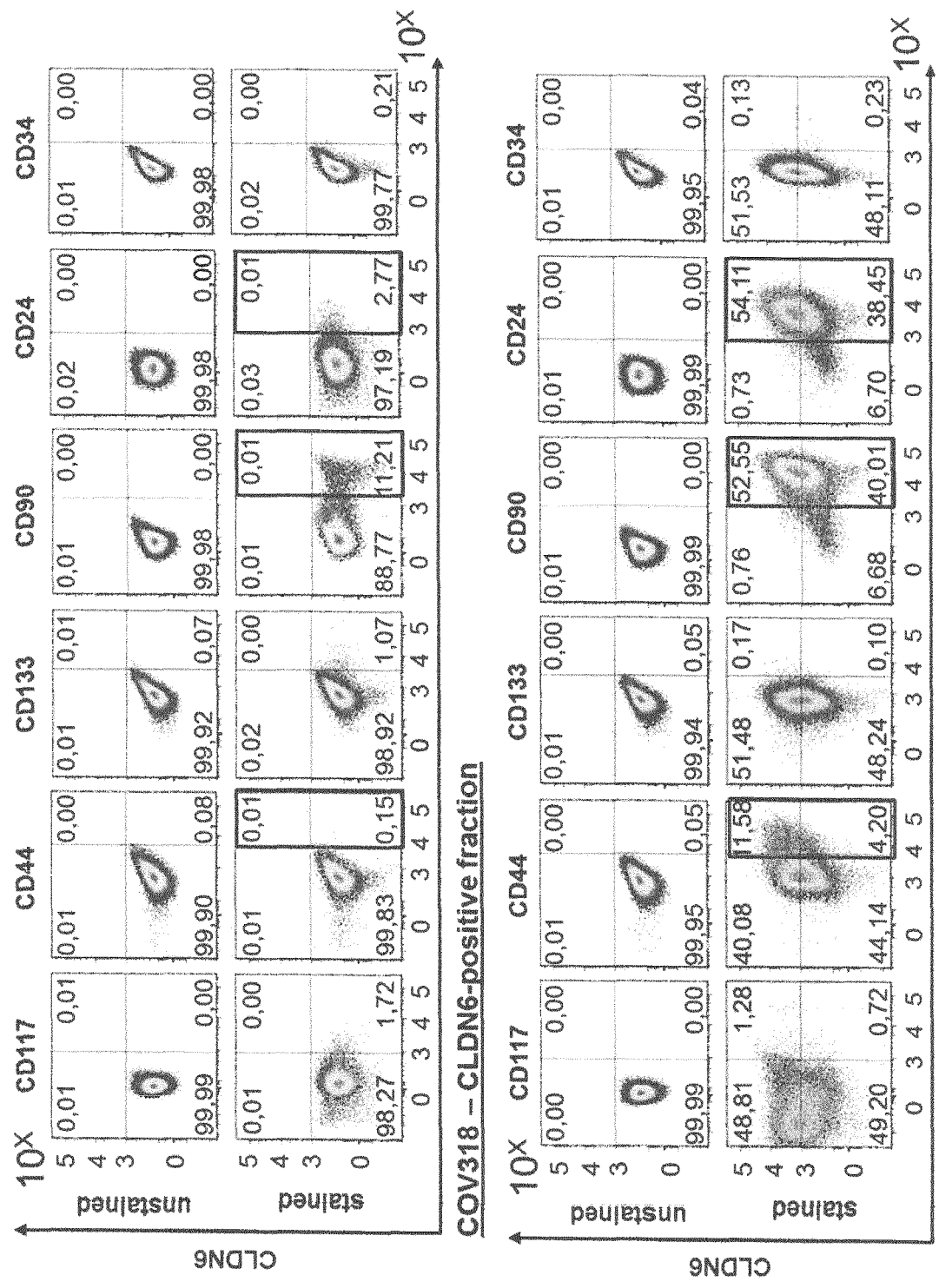

| Name | PA-1 | | OV90 | | NEC14 | |
|---|---|---|---|---|---|---|
| | relative EC50 | relative maximum | relative EC50 | relative maximum | relative EC50 | relative maximum |
| IMAB027 binding | 100% | 100% | 100% | 100% | 100% | 100% |
| IMAB027 endocytosis | 100% | 100% | 100% | 100% | 100% | 100% |
| chimAB5F2D2 binding | 92% | 143% | 69% | 97% | 80% | 93% |
| chimAB5F2D2 endocytosis | 102% | 50% | 237% | 39% | 980% | 71% |

SEQUENCE LISTING

```
<160> NUMBER OF SEQ ID NOS: 12

<210> SEQ ID NO 1
<211> LENGTH: 220
<212> TYPE: PRT
<213> ORGANISM: Homo sapiens

<400> SEQUENCE: 1

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
                100                 105                 110

Ser Lys Ala Arg Leu Val Leu Thr Ser Gly Ile Val Phe Val Ile Ser
            115                 120                 125

Gly Val Leu Thr Leu Ile Pro Val Cys Trp Thr Ala His Ala Ile Ile
        130                 135                 140
```

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
                180                 185                 190

Pro Ser His Tyr Met Ala Arg Tyr Ser Thr Ser Ala Pro Ala Ile Ser
                195                 200                 205

Arg Gly Pro Ser Glu Tyr Pro Thr Lys Asn Tyr Val
    210                 215                 220

<210> SEQ ID NO 2
<211> LENGTH: 220
<212> TYPE: PRT
<213> ORGANISM: Homo sapiens

<400> SEQUENCE: 2

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
                35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
                100                 105                 110

Ser Lys Ala Arg Leu Val Leu Thr Ser Gly Ile Val Phe Val Ile Ser
    115                 120                 125

Gly Val Leu Thr Leu Ile Pro Val Cys Trp Thr Ala His Ala Val Ile
130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
                180                 185                 190

Pro Ser His Tyr Met Ala Arg Tyr Ser Thr Ser Ala Pro Ala Ile Ser
                195                 200                 205

Arg Gly Pro Ser Glu Tyr Pro Thr Lys Asn Tyr Val
    210                 215                 220

<210> SEQ ID NO 3
<211> LENGTH: 117
<212> TYPE: PRT
<213> ORGANISM: Artificial Sequence
<220> FEATURE:
<223> OTHER INFORMATION: Antibody fragment

```
<400> SEQUENCE: 3

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Tyr Val Leu Asp Tyr Trp Gly Gln Gly Thr Thr
            100                 105                 110

Leu Thr Val Ser Ser
        115

<210> SEQ ID NO 4
<211> LENGTH: 106
<212> TYPE: PRT
<213> ORGANISM: Artificial Sequence
<220> FEATURE:
<223> OTHER INFORMATION: Antibody fragment

<400> SEQUENCE: 4

Ile Val Leu Thr Gln Ser Pro Ala Ile Met Ser Ala Ser Pro Gly Glu
1               5                   10                  15

Lys Val Thr Ile Thr Cys Ser Ala Ser Ser Ser Val Ser Tyr Leu His
            20                  25                  30

Trp Phe Gln Gln Lys Pro Gly Thr Ser Pro Lys Leu Trp Val Tyr Ser
        35                  40                  45

Thr Ser Asn Leu Pro Ser Gly Val Pro Ala Arg Phe Gly Gly Ser Gly
    50                  55                  60

Ser Gly Thr Ser Tyr Ser Leu Thr Ile Ser Arg Met Glu Ala Glu Asp
65                  70                  75                  80

Ala Ala Thr Tyr Tyr Cys Gln Gln Arg Ser Ile Tyr Pro Pro Trp Thr
                85                  90                  95

Phe Gly Gly Gly Thr Lys Leu Glu Ile Lys
            100                 105

<210> SEQ ID NO 5
<211> LENGTH: 117
<212> TYPE: PRT
<213> ORGANISM: Artificial Sequence
<220> FEATURE:
<223> OTHER INFORMATION: Antibody fragment

<400> SEQUENCE: 5

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60
```

```
Lys Gly Lys Ala Thr Leu Thr Val Asp Lys Ser Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Asp Tyr Gly Phe Val Leu Asp Tyr Trp Gly Gln Gly Thr Thr
             100                 105                 110

Leu Thr Val Ser Ser
        115
```

<210> SEQ ID NO 6
<211> LENGTH: 106
<212> TYPE: PRT
<213> ORGANISM: Artificial Sequence
<220> FEATURE:
<223> OTHER INFORMATION: Antibody fragment

<400> SEQUENCE: 6

```
Ile Val Leu Thr Gln Ser Pro Ser Ile Met Ser Val Ser Pro Gly Glu
 1               5                  10                  15

Lys Val Thr Ile Thr Cys Ser Ala Ser Ser Ser Val Ser Tyr Met His
             20                  25                  30

Trp Phe Gln Gln Lys Pro Gly Thr Ser Pro Lys Leu Cys Ile Tyr Ser
             35                  40                  45

Thr Ser Asn Leu Ala Ser Gly Val Pro Ala Arg Phe Ser Gly Arg Gly
 50                  55                  60

Ser Gly Thr Ser Tyr Ser Leu Thr Ile Ser Arg Val Ala Ala Glu Asp
 65                  70                  75                  80

Ala Ala Thr Tyr Tyr Cys Gln Gln Arg Ser Asn Tyr Pro Pro Trp Thr
                 85                  90                  95

Phe Gly Gly Gly Thr Lys Leu Glu Ile Lys
             100                 105
```

<210> SEQ ID NO 7
<211> LENGTH: 117
<212> TYPE: PRT
<213> ORGANISM: Artificial Sequence
<220> FEATURE:
<223> OTHER INFORMATION: Antibody fragment

<400> SEQUENCE: 7

```
Glu Val Gln Leu Gln Gln Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
             20                  25                  30

Thr Met Asn Trp Val Lys Gln Ser His Gly Lys Asn Leu Glu Trp Ile
             35                  40                  45

Gly Leu Ile Asn Pro Tyr Asn Gly Gly Ile Ile Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Leu Ser Leu Thr Ser Glu Asp Ser Ala Val Phe Tyr Cys
                 85                  90                  95

Ala Arg Asp Phe Gly Tyr Val Leu Asp Tyr Trp Gly Gln Gly Thr Thr
             100                 105                 110

Leu Thr Val Ser Ser
        115
```

```
<210> SEQ ID NO 8
<211> LENGTH: 106
<212> TYPE: PRT
<213> ORGANISM: Artificial Sequence
<220> FEATURE:
<223> OTHER INFORMATION: Antibody fragment

<400> SEQUENCE: 8

Ile Val Leu Thr Gln Ser Pro Ala Ile Met Ser Ala Ser Pro Gly Glu
1               5                   10                  15

Lys Val Thr Ile Thr Cys Ser Ala Ser Ser Val Ser Tyr Met His
            20                  25                  30

Trp Phe Gln Gln Lys Pro Gly Thr Ser Pro Lys Leu Trp Ile Tyr Ser
        35                  40                  45

Thr Ser Asn Leu Ala Ser Gly Val Pro Ala Arg Phe Ser Gly Ser Gly
    50                  55                  60

Ser Gly Thr Ser Tyr Ser Leu Thr Ile Ser Arg Val Ala Ala Glu Asp
65                  70                  75                  80

Ala Ala Thr Tyr Tyr Cys Gln Gln Arg Ser Thr Tyr Pro Pro Trp Thr
                85                  90                  95

Phe Gly Gly Gly Thr Lys Leu Glu Ile Lys
            100                 105

<210> SEQ ID NO 9
<211> LENGTH: 117
<212> TYPE: PRT
<213> ORGANISM: Artificial Sequence
<220> FEATURE:
<223> OTHER INFORMATION: Antibody fragment

<400> SEQUENCE: 9

Glu Val Gln Leu Gln Gln Ser Arg Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Leu Asn Trp Val Lys Gln Ser His Gly Lys Asn Leu Glu Trp Ile
        35                  40                  45

Gly Leu Ile Asn Pro Tyr Asn Gly Gly Ser Ser Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Tyr Val Phe Asp Tyr Trp Gly Gln Gly Thr Thr
            100                 105                 110

Leu Thr Val Ser Ser
        115

<210> SEQ ID NO 10
<211> LENGTH: 106
<212> TYPE: PRT
<213> ORGANISM: Artificial Sequence
<220> FEATURE:
<223> OTHER INFORMATION: Antibody fragment

<400> SEQUENCE: 10

Ile Val Leu Thr Gln Ser Pro Ala Ile Met Ser Ala Ser Pro Gly Glu
1               5                   10                  15

Lys Val Thr Ile Thr Cys Ser Ala Ser Ser Val Asn Tyr Met His
            20                  25                  30
```

```
Trp Phe Gln Leu Lys Pro Gly Thr Ser Pro Lys Leu Leu Ile Tyr Ser
            35                  40                  45

Thr Ser Asn Leu Ala Ser Gly Val Pro Ala Arg Phe Ser Gly Arg Gly
        50                  55                  60

Ser Gly Thr Ser Tyr Ser Leu Thr Ile Ser Arg Met Glu Ala Glu Asp
 65                  70                  75                  80

Ala Ala Thr Tyr Tyr Cys Gln Gln Arg Asn Asn Tyr Pro Pro Trp Thr
                85                  90                  95

Phe Gly Gly Gly Thr Lys Leu Glu Ile Lys
            100                 105

<210> SEQ ID NO 11
<211> LENGTH: 106
<212> TYPE: PRT
<213> ORGANISM: Artificial Sequence
<220> FEATURE:
<223> OTHER INFORMATION: Antibody fragment

<400> SEQUENCE: 11

Ile Val Leu Thr Gln Ser Pro Ser Ile Met Ser Val Ser Pro Gly Glu
 1               5                  10                  15

Lys Val Thr Ile Thr Cys Ser Ala Ser Ser Val Ser Tyr Met His
            20                  25                  30

Trp Phe Gln Gln Lys Pro Gly Thr Ser Pro Lys Leu Gly Ile Tyr Ser
            35                  40                  45

Thr Ser Asn Leu Ala Ser Gly Val Pro Ala Arg Phe Ser Gly Arg Gly
        50                  55                  60

Ser Gly Thr Ser Tyr Ser Leu Thr Ile Ser Arg Val Ala Ala Glu Asp
 65                  70                  75                  80

Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105

<210> SEQ ID NO 12
<211> LENGTH: 106
<212> TYPE: PRT
<213> ORGANISM: Artificial Sequence
<220> FEATURE:
<223> OTHER INFORMATION: Antibody fragment

<400> SEQUENCE: 12

Ile Val Leu Thr Gln Ser Pro Ser Ile Met Ser Val Ser Pro Gly Glu
 1               5                  10                  15

Lys Val Thr Ile Thr Cys Ser Ala Ser Ser Val Ser Tyr Met His
            20                  25                  30

Trp Phe Gln Gln Lys Pro Gly Thr Ser Pro Lys Leu Ser Ile Tyr Ser
            35                  40                  45

Thr Ser Asn Leu Ala Ser Gly Val Pro Ala Arg Phe Ser Gly Arg Gly
        50                  55                  60

Ser Gly Thr Ser Tyr Ser Leu Thr Ile Ser Arg Val Ala Ala Glu Asp
 65                  70                  75                  80

Ala Ala Thr Tyr Tyr Cys Gln Gln Arg Ser Asn Tyr Pro Pro Trp Thr
                85                  90                  95

Phe Gly Gly Gly Thr Lys Leu Glu Ile Lys
            100                 105
```

DIAGNOSIS AND THERAPY OF CANCER INVOLVING CANCER STEM CELLS

Conventional cancer therapies have mainly attempted to selectively detect and eradicate cancer cells that are largely fast-growing (i.e., cells that form the tumor bulk) and exert their toxic effects on cancer cells largely by interfering with cellular mechanisms involved in cell growth and DNA replication. Furthermore, standard oncology regimens have been largely designed to administer the highest dose of irradiation or a chemotherapeutic agent without undue toxicity, i.e., often referred to as the "maximum tolerated dose" (MTD).

Chemotherapy protocols also often involve administration of a combination of chemotherapeutic agents in an attempt to increase the efficacy of treatment. Despite the availability of a large variety of chemotherapeutic agents, these therapies have many drawbacks. For example, chemotherapeutic agents cause significant, and often dangerous, side effects due to non-specific side effects on fast-growing cells whether normal or malignant.

Other types of cancer therapies include surgery, hormonal therapy, immunotherapy, epigenetic therapy, anti-angiogenesis therapy, targeted therapy, and radiation treatment to eradicate neoplastic cells in a patient.

However, all of the conventional approaches for cancer therapy have significant drawbacks for the patient including a lack of efficacy (in particular in terms of long-term outcome) and toxicity. Accordingly, new therapies for treating cancer patients are needed.

There is increasing evidence that a subpopulation of cancer cells exists within the tumor which retain stem-like properties. This subpopulation is termed cancer stem cells (CSC). Cancer stem cells have similar properties compared to normal stem cells, they have the capability for self-renewal and formation of all heterogeneous cell types of a tumor. A potent assay to analyze CSC-like properties of tumor cells is the colony formation assay. Using this assay, one can easily examine self-renewal capacity and tumor formation potency of single tumor cells.

Cancer stem cells are thought to be capable to initiate tumor formation, maintain tumor growth and possibly lead to tumor dissemination to distant organ sites in the body. Cancer stem cells comprise a unique subpopulation of a tumor that, relative to the remaining cells of the tumor (i.e., the tumor bulk), are more tumorigenic, relatively more slow-growing or quiescent, and often relatively more chemoresistant than the tumor bulk. Since conventional cancer therapies target rapidly proliferating cells (i.e., cells that form the tumor bulk) these treatments are believed to be relatively ineffective at targeting and impairing cancer stem cells. Cancer stem cells can express other features which make them relatively chemoresistant such as multi-drug resistance and anti-apoptotic pathways. The failure to adequately target and eradicate cancer stem cells would constitute a key reason for the failure of standard oncology treatment regimens to ensure long-term benefit in many cancer patients. Thus, the cancer stem cells may not only be the main reason for cancer recurrence after treatment and the ineffectiveness of drugs but also the main reason for malignant cancer metastasis. Thus, one opportunity to cure cancers is to eliminate the cancer stem cells.

Claudins are integral membrane proteins located within the tight junctions of epithelia and endothelia. Claudins are predicted to have four transmembrane segments with two extracellular loops, and N- and C-termini located in the cytoplasm. The claudin (CLDN) family of transmernbrane proteins plays a critical role in the maintenance of epithelial and endothelial tight junctions and might also play a role in the maintenance of the cytoskeleton and in cell signaling. CLDN6 is expressed in a series of different human cancer cells while expression in normal tissues is limited to placenta.

Here we present data demonstrating that CLDN6 expression is upregulated during the generation of pluripotent cells. Furthermore, CLDN6 is strongly associated with known markers for cancer stem cells and CLDN6 positive tumor cells show enhanced formation of colonies. It is also demonstrated that therapy using CLDN6 specific antibodies can overcome the chemotherapeutic resistance of tumors such as ovarian cancer and the combination of chemotherapy and CLDN6 antibody therapy has a remarkable synergistic effect.

The findings presented herein indicate that CLDN6 is a novel marker for cancer stem cells and that cancer stem cells can be targeted for diagnostic and therapeutic purposes by targeting CLDN6.

SUMMARY OF THE INVENTION

In one aspect, the present invention relates to a method of determining cancer stem cells comprising detecting cells expressing CLDN6.

In one embodiment, the presence of cells expressing CLDN6 indicates the presence of cancer stem cells and/or the amount of cells expressing CLDN6 correlates with the amount of cancer stem cells. In one embodiment, cells expressing CLDN6 are detected in a sample obtained from a cancer patient such as prior to, during and/or following treatment for cancer. In one embodiment, the method comprises a quantitative and/or qualitative determination of cells expressing CLDN6. In one embodiment, the method comprises comparing the amount of cells expressing CLDN6 to the amount of cells expressing CLDN6 in a reference sample or to a predetermined reference range. The reference sample may be a sample from a patient who has not been diagnosed with cancer. The predetermined reference range may be based on a population of patients who have not been diagnosed with cancer. In one embodiment, the method comprises monitoring the amount of cancer stem cells in a cancer patient, wherein monitoring the amount of cancer stem cells in a cancer patient preferably comprises comparing the amount of cancer stem cells in a sample obtained from the cancer patient to the amount of cancer stem cells in a sample obtained earlier from the cancer patient. In one embodiment, the sample obtained from the cancer patient is a sample taken from the cancer patient during or following the administration of cancer therapy.

In a further aspect, the present invention relates to a method of monitoring the efficacy of a cancer therapy in a cancer patient comprising: (i) determining the amount of cancer stem cells in a sample obtained from the cancer patient during or following the administration of the cancer therapy; and (ii) comparing the amount of cancer stem cells in the sample obtained from the cancer patient to the amount of cancer stem cells in a sample obtained earlier from the cancer patient, wherein determining the amount of cancer stem cells in the sample obtained from the cancer patient and/or determining the amount of cancer stem cells in the sample obtained earlier from the cancer patient comprises determining the amount of cells expressing CLDN6.

In one embodiment, the sample obtained earlier from the cancer patient is a sample taken from the cancer patient prior to, during or following the administration of cancer therapy.

In one embodiment of the method of all aspects of the invention, a stabilization or a decrease in the amount of cancer stem cells indicates that the cancer therapy is effective. In one embodiment of the method of all aspects of the invention, an increase in the amount of cancer stem cells indicates that the cancer therapy is ineffective. In one embodiment of the method of all aspects of the invention, the cancer therapy is cancer therapy directed against cancer stem cells. In one embodiment of the method of all aspects of the invention, the sample obtained from the cancer patient is a biological fluid or a tumor biopsy. In one embodiment of the method of all aspects of the invention, the sample has been subjected to one or more pretreatment steps. In one embodiment of the method of all aspects of the invention, the cells expressing CLDN6 are detected or their amount is determined by detecting or determining the amount of CLDN6 protein and/or CLDN6 mRNA. In one embodiment of the method of all aspects of the invention, the cells expressing CLDN6 are detected or their amount is determined by using an immunoassay, wherein the immunoassay is preferably selected from the group consisting of western blots, immunohistochemistry, radioimmunoassays, ELISA (enzyme linked immunosorbent assay), "sandwich" immunoassays, immunoprecipitation assays, precipitation reactions, gel diffusion precipitation reactions, immunodiffusion assays, agglutination assays, complement-fixation assays, immunoradiometric assays, fluorescent immunoassays, immunofluorescence, protein A immunoassays, flow cytometry and FACS analysis. In one embodiment of the method of all aspects of the invention, the cells expressing CLDN6 are detected or their amount is determined by using an antibody having the ability of binding to CLDN6. In one embodiment of the method of all aspects of the invention, the cells expressing CLDN6 are cancer cells expressing CLDN6 and/or are cells which are present at a tumor site.

In a further aspect, the present invention relates to a method of treating or preventing cancer comprising inhibiting and/or eliminating cancer stem cells by administering an antibody having the ability of binding to CLDN6 to a cancer patient.

In one embodiment, the cancer stem cells express CLDN6. In one embodiment, the method further comprises administering chemotherapy and/or radiation therapy. In one embodiment, inhibiting and/or eliminating cancer stem cells enhances the anti-cancer effect of chemotherapy and/or radiation therapy, wherein enhancement of the anti-cancer effect of chemotherapy and/or radiation therapy preferably comprises an expansion of the lifespan of a cancer patient undergoing chemotherapy and/or radiation therapy.

In a further aspect, the present invention relates to a method of treating or preventing cancer comprising administering (i) an antibody having the ability of binding to CLDN6 and (ii) chemotherapy to a cancer patient.

In one embodiment, the cancer involves cancer stem cells expressing CLDN6. In one embodiment, administering an antibody having the ability of binding to CLDN6 results in inhibition or elimination of cancer stem cells expressing CLDN6. In one embodiment, administering an antibody having the ability of binding to CLDN6 enhances the anti-cancer effect of chemotherapy, wherein enhancement of the anti-cancer effect of chemotherapy preferably comprises an expansion of the lifespan of a cancer patient undergoing chemotherapy.

In one embodiment of the method of all aspects of the invention, elimination of cancer stem cells results in curing of cancer. In one embodiment of the method of all aspects of the invention, the antibody having the ability of binding to CLDN6 and the chemotherapy are administered in synergistically effective amounts. In one embodiment of the method of all aspects of the invention, the chemotherapy is administered at a dose which is below the maximum tolerated dose. In one embodiment of the method of all aspects of the invention, the chemotherapy comprises administering an agent selected from the group consisting of taxanes, platinum compounds, nucleoside analogs, camptothecin analogs, anthracyclines, prodrugs thereof, salts thereof, and combinations thereof. In one embodiment of the method of all aspects of the invention, the chemotherapy comprises administering an agent selected from the group consisting of paclitaxel, cisplatin, carboplatin, prodrugs thereof, salts thereof, and combinations thereof. In one embodiment of the method of all aspects of the invention, the cancer stem cells are at a tumor site of the cancer patient. In one embodiment of the method of all aspects of the invention, the cancer is resistant to chemotherapy, in particular if administered as monotherapy. In one embodiment of the method of all aspects of the invention, the antibody having the ability of binding to CLDN6 has an inhibitory and/or cytotoxic effect on cancer stem cells, wherein the antibody having the ability of binding to CLDN6 exerts its inhibitory and/or cytotoxic effect on cancer stem cells preferably by mediating one or more of complement dependent cytotoxicity (CDC) mediated lysis, antibody dependent cellular cytotoxicity (ADCC) mediated lysis, induction of apoptosis and inhibition of proliferation. In one embodiment of the method of all aspects of the invention, the antibody having the ability of binding to CLDN6 is coupled to a therapeutic moiety and may be an antibody drug conjugate as described herein. In one embodiment, the therapeutic moiety is a cytotoxic agent, a chemotherapeutic agent or a radionuclide. In one embodiment, the therapeutic moiety acts on slow-growing cells. In one embodiment of the method of all aspects of the invention, the antibody having the ability of binding to CLDN6 binds to the first extracellular loop of CLDN6. In one embodiment of the method of all aspects of the invention, the antibody having the ability of binding to CLDN6 comprises a heavy chain variable region (VH) comprising an amino acid sequence represented by SEQ ID NO: 5 or a fragment thereof and a light chain variable region (VL) comprising an amino acid sequence represented by SEQ ID NO: 4 or a fragment thereof.

In a further aspect, the present invention relates to a method of treating or preventing cancer comprising administering an antibody drug conjugate comprising an antibody having the ability of binding to CLDN6 covalently attached by a linker to at least one toxin drug moiety to a cancer patient.

In one embodiment, the toxin drug moiety is cell membrane-permeable. In one embodiment, at least one of the toxin drug moieties acts on slow-growing cells. In one embodiment, the toxin drug moiety is a maytansinoid or an auristatin. In one embodiment, the maytansinoid is selected from the group consisting of DM1 and DM4. In one embodiment, the auristatin is selected from the group consisting of monomethyl auristatin E (MMAE) and monomethyl auristatin F (MMAF). In one embodiment, the linker is a cleavable linker, preferably a cathepsin-cleavable linker. In one embodiment, the antibody is attached to the linker through a cysteine thiol of the antibody.

In one embodiment, the cancer involves cancer stem cells expressing CLDN6. In one embodiment, administering the antibody drug conjugate results in inhibition or elimination of cancer stem cells expressing CLDN6. In one embodiment, elimination of cancer stem cells results in curing of cancer. In one embodiment, the cancer stem cells are at a tumor site of the cancer patient. In one embodiment, the antibody drug conjugate has an inhibitory and/or cytotoxic effect on cancer stem cells, wherein the antibody drug conjugate exerts its inhibitory and/or cytotoxic effect on cancer stem cells preferably by induction of apoptosis and/or inhibition of proliferation.

In one embodiment, the method further comprises administering chemotherapy and/or radiation therapy. In one embodiment, administering the antibody drug conjugate enhances the anti-cancer effect of chemotherapy and/or radiation therapy, wherein enhancement of the anti-cancer effect of chemotherapy and/or radiation therapy preferably comprises an expansion of the lifespan of a cancer patient undergoing chemotherapy and/or radiation therapy.

In one embodiment, the antibody drug conjugate and the chemotherapy are administered in synergistically effective amounts. In one embodiment, the chemotherapy is administered at a dose which is below the maximum tolerated dose. In one embodiment, the chemotherapy comprises administering an agent selected from the group consisting of taxanes, platinum compounds, nucleoside analogs, camptothecin analogs, anthracyclines, prodrugs thereof, salts thereof, and combinations thereof. In one embodiment, the chemotherapy comprises administering an agent selected from the group consisting of paclitaxel, cisplatin, carboplatin, prodrugs thereof, salts thereof, and combinations thereof. In one embodiment, the cancer is resistant to chemotherapy, in particular if administered as monotherapy.

In one embodiment, the antibody having the ability of binding to CLDN6, in particular when present in the antibody drug conjugate, has an affinity and/or specificity for CLDN6 appropriate to allow endocytosis of the antibody and/or the antibody drug conjugate. In one embodiment, the antibody having the ability of binding to CLDN6 in the antibody drug conjugate binds to the first extracellular loop of CLDN6. In one embodiment, the antibody having the ability of binding to CLDN6 in the antibody drug conjugate comprises a heavy chain variable region (VH) comprising an amino acid sequence represented by SEQ ID NO: 5 or a fragment thereof and a light chain variable region (VL) comprising an amino acid sequence represented by SEQ ID NO: 4 or a fragment thereof.

In one embodiment of the method of all aspects of the invention, CLDN6 has the amino acid sequence according to SEQ ID NO: 1 or SEQ ID NO: 2. In one embodiment of the method of all aspects of the invention, the cancer comprises primary cancer, advanced cancer, metastatic cancer, recurrent cancer or a combination thereof.

In a further aspect, the present invention relates to a method of treating or preventing cancer comprising: (i) determining cancer stem cells in a cancer patient by the method of the invention and (ii) administering to the cancer patient cancer therapy directed against cancer stem cells. In one embodiment, the cancer therapy directed against cancer stem cells comprises performing the method of treating or preventing cancer of the invention.

In a further aspect, the present invention relates to a method of preventing cancer chemoresistance, cancer recurrence, or cancer metastasis, in particular during or after cancer treatment, comprising treating cancer by the method of the invention.

In a further aspect, the present invention provides a medical preparation for treating or preventing cancer comprising (i) an antibody having the ability of binding to CLDN6 and (ii) a chemotherapeutic agent. The antibody having the ability of binding to CLDN6 and the chemotherapeutic agent may be present in the medical preparation in a mixture or separate from each other. The medical preparation may be present in the form of a kit comprising a first container including the antibody having the ability of binding to CLDN6 and a second container including the chemotherapeutic agent. The medical preparation may further include printed instructions for use of the preparation for treatment or prevention of cancer, in particular for use of the preparation in a method of the invention. Different embodiments of the medical preparation, and, in particular, of the antibody having the ability of binding to CLDN6 and the chemotherapeutic agent are as described herein.

In a particular aspect, the present invention provides a medical preparation comprising (i) an antibody having the ability of binding to CLDN6 and (ii) paclitaxel. The antibody having the ability of binding to CLDN6 and paclitaxel may be present in the medical preparation in a mixture or separate from each other. The medical preparation may be for treating or preventing cancer such as ovarian cancer. The medical preparation may be present in the form of a kit comprising a first container including the antibody having the ability of binding to CLDN6 and a second container including paclitaxel. The medical preparation may further include printed instructions for use of the preparation for treatment or prevention of cancer such as ovarian cancer, in particular for use of the preparation in a method of the invention. Different embodiments of the medical preparation, and, in particular, of the antibody having the ability of binding to CLDN6 are as described herein.

In a further aspect, the present invention provides an antibody drug conjugate comprising an antibody having the ability of binding to CLDN6 covalently attached by a linker to at least one toxin drug moiety.

In one embodiment, the toxin drug moiety is cell membrane-permeable. In one embodiment, at least one of the toxin drug moieties acts on slow-growing cells. In one embodiment, the toxin drug moiety is a maytansinoid or an auristatin. In one embodiment, the maytansinoid is selected from the group consisting of DM1 and DM4. In one embodiment, the auristatin is selected from the group consisting of monomethyl auristatin E (MMAE) and monomethyl auristatin F (MMAF). In one embodiment, the linker is a cleavable linker, preferably a cathepsin-cleavable linker. In one embodiment, the antibody is attached to the linker through a cysteine thiol of the antibody.

In one embodiment, the antibody having the ability of binding to CLDN6, in particular when present in the antibody drug conjugate, has an affinity and/or specificity for CLDN6 appropriate to allow endocytosis of the antibody and/or the antibody drug conjugate. In one embodiment, the antibody having the ability of binding to CLDN6 in the antibody drug conjugate binds to the first extracellular loop of CLDN6. In one embodiment, the antibody having the ability of binding to CLDN6 in the antibody drug conjugate comprises a heavy chain variable region (VH) comprising an amino acid sequence represented by SEQ ID NO: 5 or a fragment thereof and a light chain variable region (VL) comprising an amino acid sequence represented by SEQ ID NO: 4 or a fragment thereof.

In a further aspect, the present invention provides a pharmaceutical formulation comprising the antibody drug conjugate of the invention, and a pharmaceutically acceptable diluent, carrier or excipient.

In a further aspect, the present invention provides a medical preparation comprising the antibody drug conjugate of the invention, and a chemotherapeutic agent. Preferably, the medical preparation is for treating or preventing cancer.

The antibody drug conjugate and the chemotherapeutic agent may be present in the medical preparation in a mixture or separate from each other. The medical preparation may be present in the form of a kit comprising a first container including the antibody drug conjugate and a second container including the chemotherapeutic agent. The medical preparation may further include printed instructions for use of the preparation for treatment or prevention of cancer, in particular for use of the preparation in a method of the invention. Different embodiments of the medical preparation, and, in particular, of the antibody drug conjugate and the chemotherapeutic agent are as described herein.

In a particular aspect, the present invention provides a medical preparation comprising the antibody drug conjugate of the invention and paclitaxel. The antibody drug conjugate and paclitaxel may be present in the medical preparation in a mixture or separate from each other. The medical preparation may be for treating or preventing cancer such as ovarian cancer. The medical preparation may be present in the form of a kit comprising a first container including the antibody drug conjugate and a second container including paclitaxel. The medical preparation may further include printed instructions for use of the preparation for treatment or prevention of cancer such as ovarian cancer, in particular for use of the preparation in a method of the invention. Different embodiments of the medical preparation, and, in particular, of the antibody drug conjugate are as described herein.

The present invention also provides the agents and compositions described herein such as the antibody drug conjugate, the antibody having the ability of binding to CLDN6 and/or the chemotherapeutic agent for use in the methods described herein. For example, the present invention also provides the antibody drug conjugate or the antibody having the ability of binding to CLDN6 for administration in conjunction with a chemotherapeutic agent such as paclitaxel.

In one embodiment, the antibody having the ability of binding to CLDN6 is a monoclonal, chimeric or humanized antibody, or a fragment of an antibody. In one embodiment, the antibody mediates cell killing when bound to cellular CLDN6, in particular to CLDN6 expressed by cells on their cell surface, wherein the cells are preferably cancer stem cells, such as cancer stem cells of the cancers described herein.

According to the invention, a cancer is preferably selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, large cell carcinoma (LCC), gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, placental choriocarcinoma, cervical cancer, testicular cancer, in particular testicular seminoma, testicular teratoma and testicular embryonal carcinoma, uterine cancer, germ cell tumors such as a teratocarcinoma or embryonal carcinoma, in particular germ cell tumors of the testis and ovary, and the metastatic forms thereof.

According to the invention, cancer cells and/or cancer stem cells expressing CLDN6 preferably are cells of a cancer described herein.

In one embodiment, a cancer described herein is CLDN6 positive. In one embodiment, cancer cells of a cancer described herein are CLDN6 positive. In one embodiment, cancer cells of a cancer described herein express CLDN6 on their cell surface.

In one embodiment, a cancer described herein comprises primary cancer, advanced cancer, metastatic cancer, recurrent cancer or a combination thereof such as a combination of primary cancer and metastatic cancer. In one embodiment, the cancer is partially or completely refractory to chemotherapy such as paclitaxel monotherapy. In one embodiment, the cancer is ovarian cancer, in particular ovarian cancer partially or completely refractory to chemotherapy such as paclitaxel monotherapy.

Other features and advantages of the instant invention will be apparent from the following detailed description and claims.

To analyze the clonogenic behavior, COV318, PA-1 50 and PA-1 54 cells were stained with 1 µg/ml IMAB027-AF647 for 30 min at 4° C. and afterwards 700 (COV318) or 500 (PA-1 50/54) CLDN6-positive or CLDN6-negative cells were sorted into 6 well plates. Cells were allowed to form colonies for 14 days and were afterwards stained with 0.5% crystal violet for 20 min. (A) A representative picture for each cell line is shown. (B) Quantification of colonies was performed by manually counting. Mean and standard deviation of three independent experiments is shown.

Figure 5:
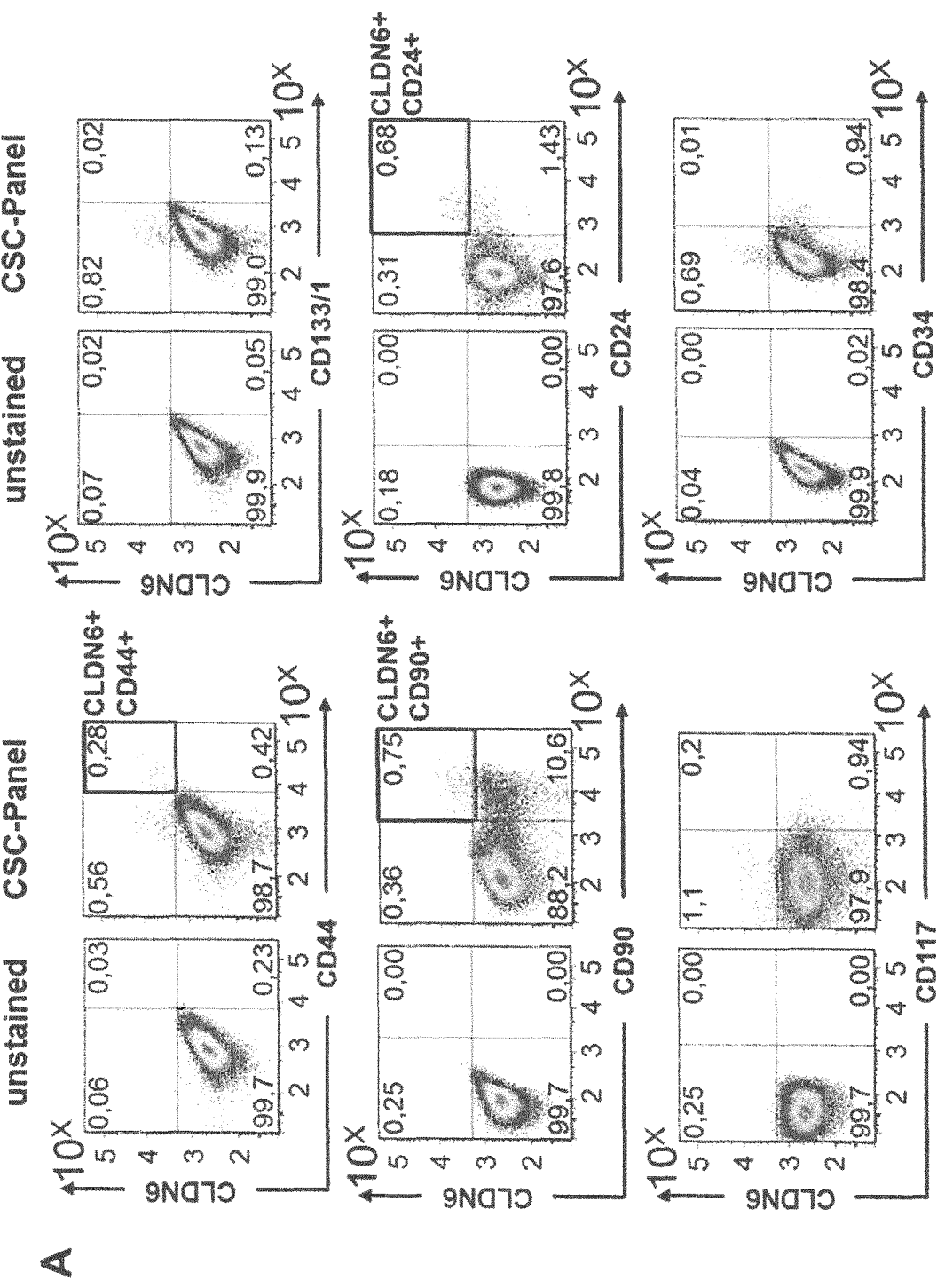
Figure 5:
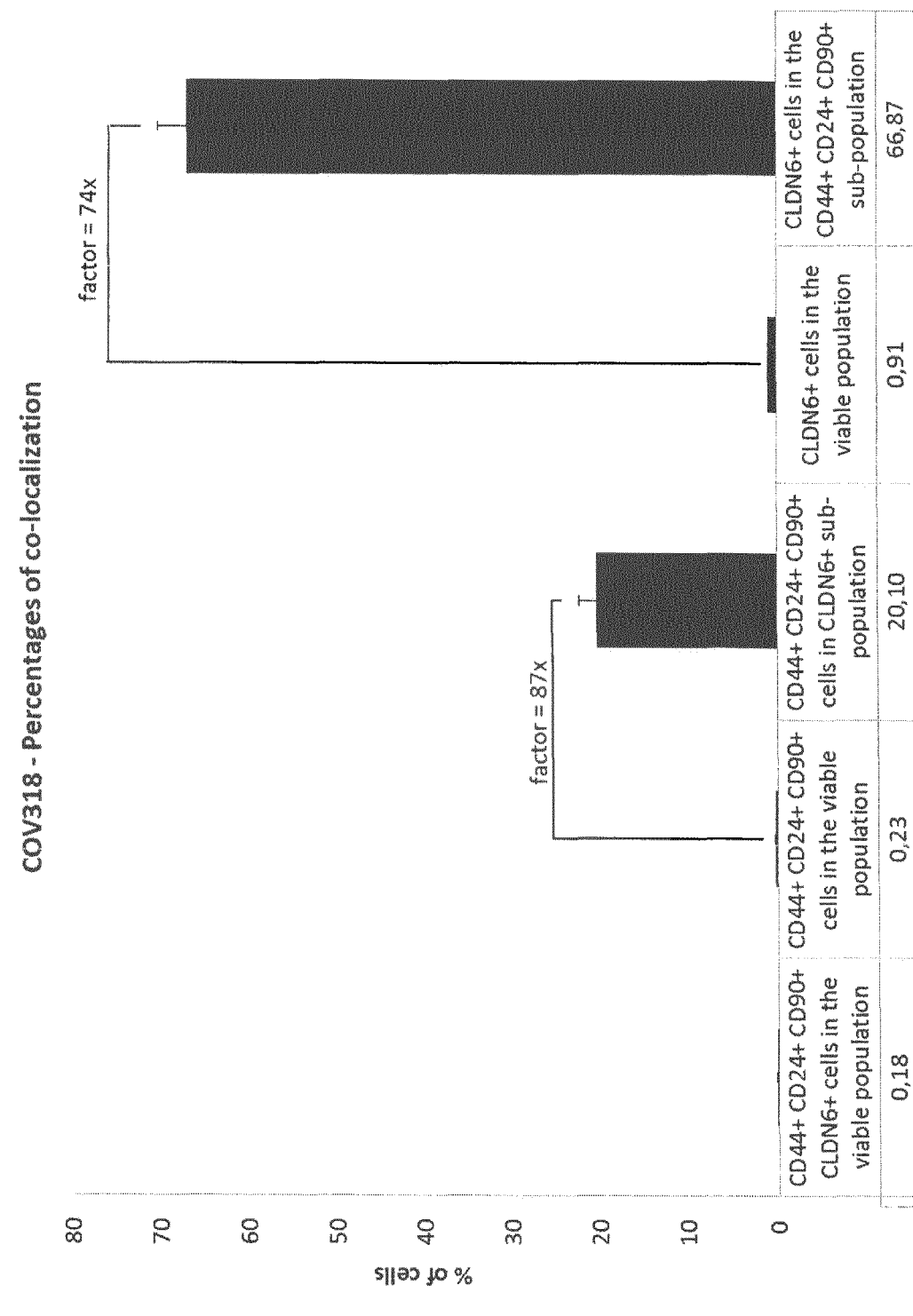

FIG. 5: CLDN6 is co-expressed with CSC markers CD24, CD90 and CD44 in the ovarian cancer cell line COV318.

1E6 COV318 cells were stained for 30 min at 4° C. with antibodies against the different surface markers according to the FACS panel shown in Table 1 and CSC marker expression was analyzed by flow cytometry. Experiments were performed in triplicates. In (A) representative dot plots of co-localization of CLDN6 with different established CSC markers are shown. In (B) percentages of co-localization of CD44, CD24, CD90 and CLDN6 positive cells were calculated using different gating strategies indicated on the x-axis of the diagram. Mean values of triplicates and standard deviation are shown.

Figure 6:
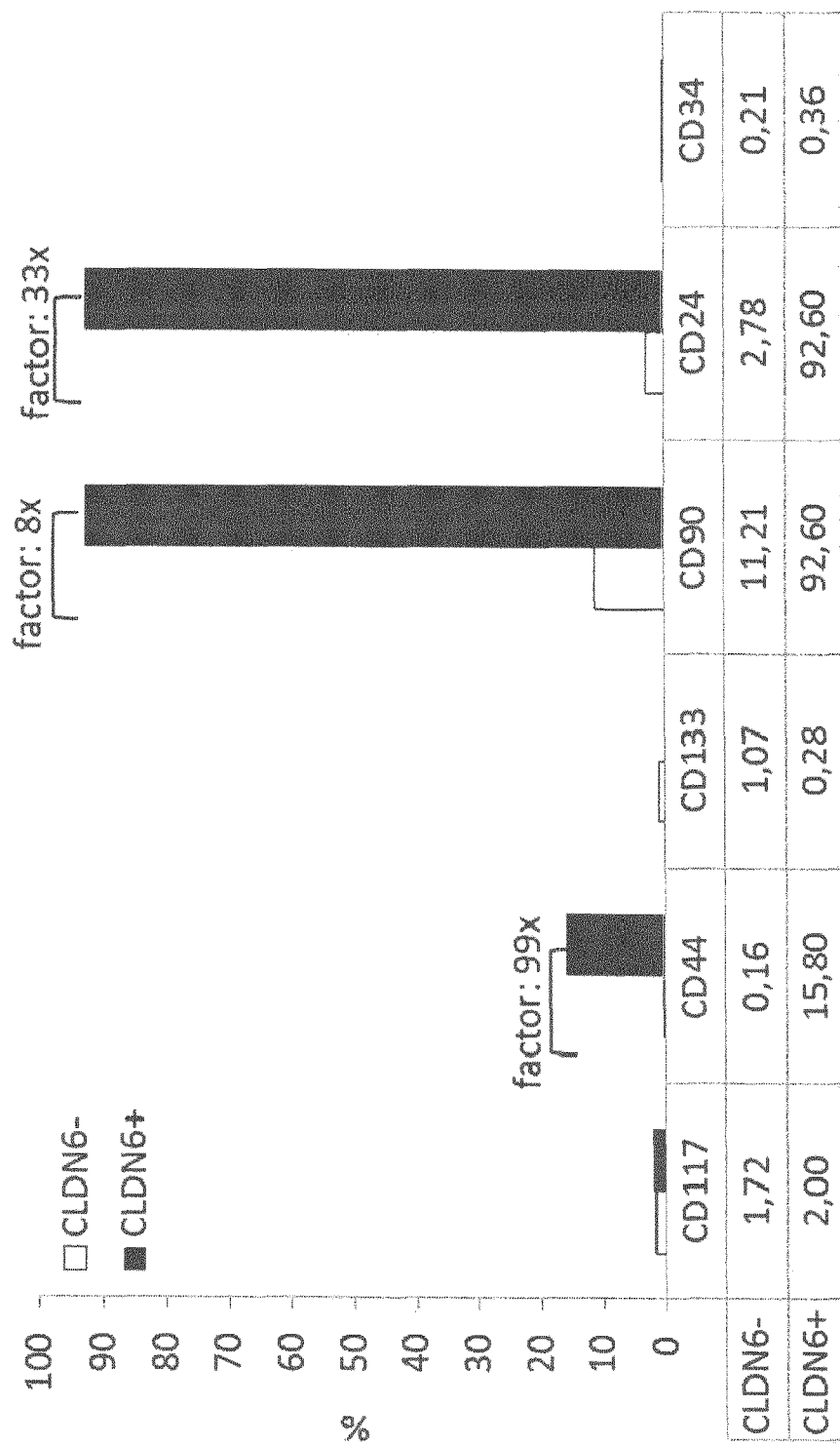

FIG. 6: Enrichment of CLDN6 expressing cells leads to an accumulation of established CSC markers.

COV318 cells were stained with 0.5 µh/ml IMAB027 and secondary APC-conjugated goat anti-human IgG secondary antibody (1:300) and CLDN6-positive and CLDN6-negative fractions were afterwards isolated by FACS sorting. Cells of both fractions were expanded for 10 days. 1E6 cells of each fraction were stained for 30 min at 4° C. with antibodies against the different surface markers according to the FACS panel shown in Table 1. The experiment was performed in triplicates. In (A) representative dot plots of expression levels of the different CSC markers in the CLDN6-positive and CLDN6-negative fraction are shown as well as their co-localization with CLDN6. In (B) percentages of CSC marker expression levels are shown as diagram and enrichment factors (fold expression) for the relevant markers CD44, CD90 and CD24 were calculated by comparing percentages of positive cells in the CLDN6-positive and CLDN6-negative fraction.

Figure 7:
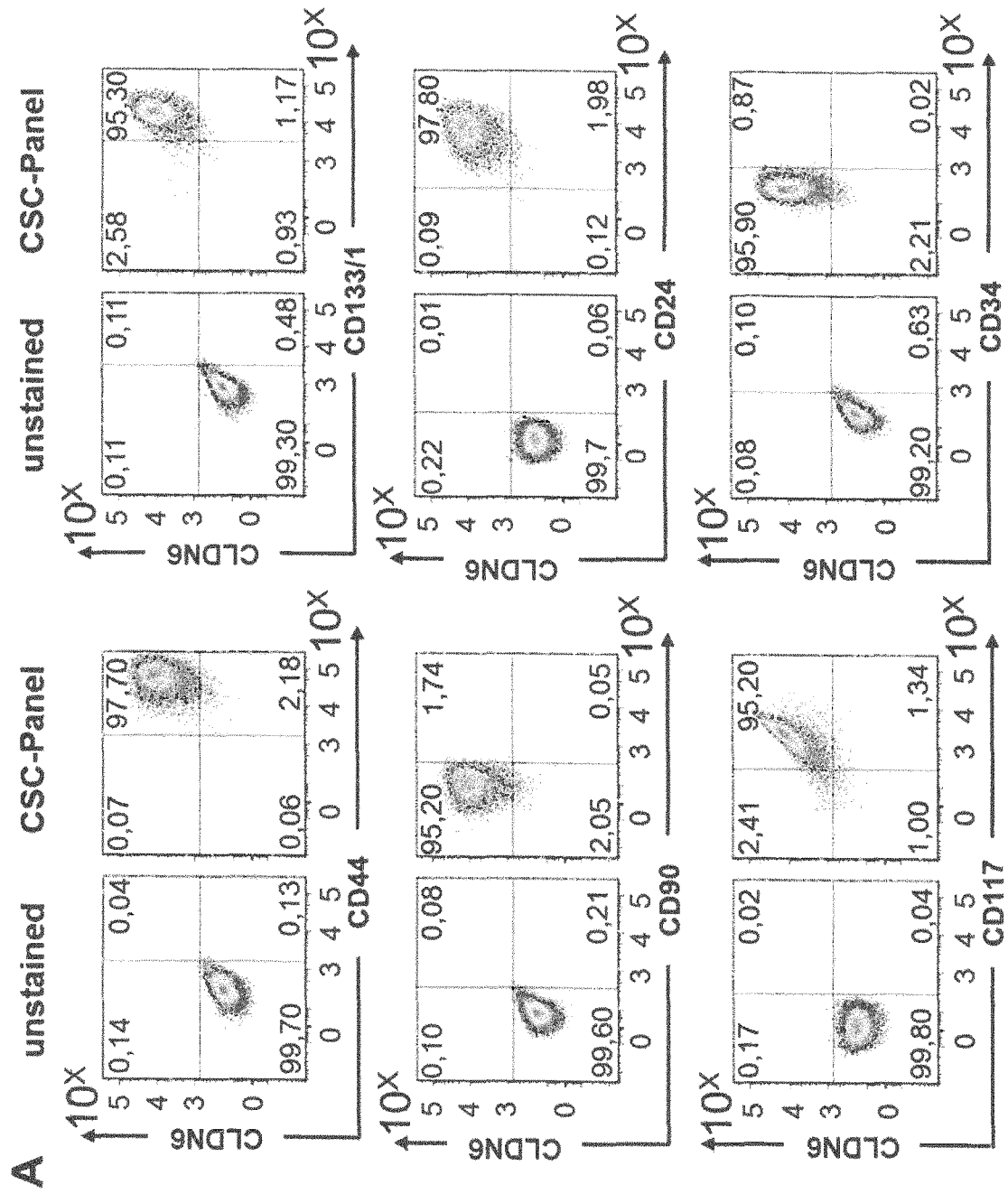
Figure 7:
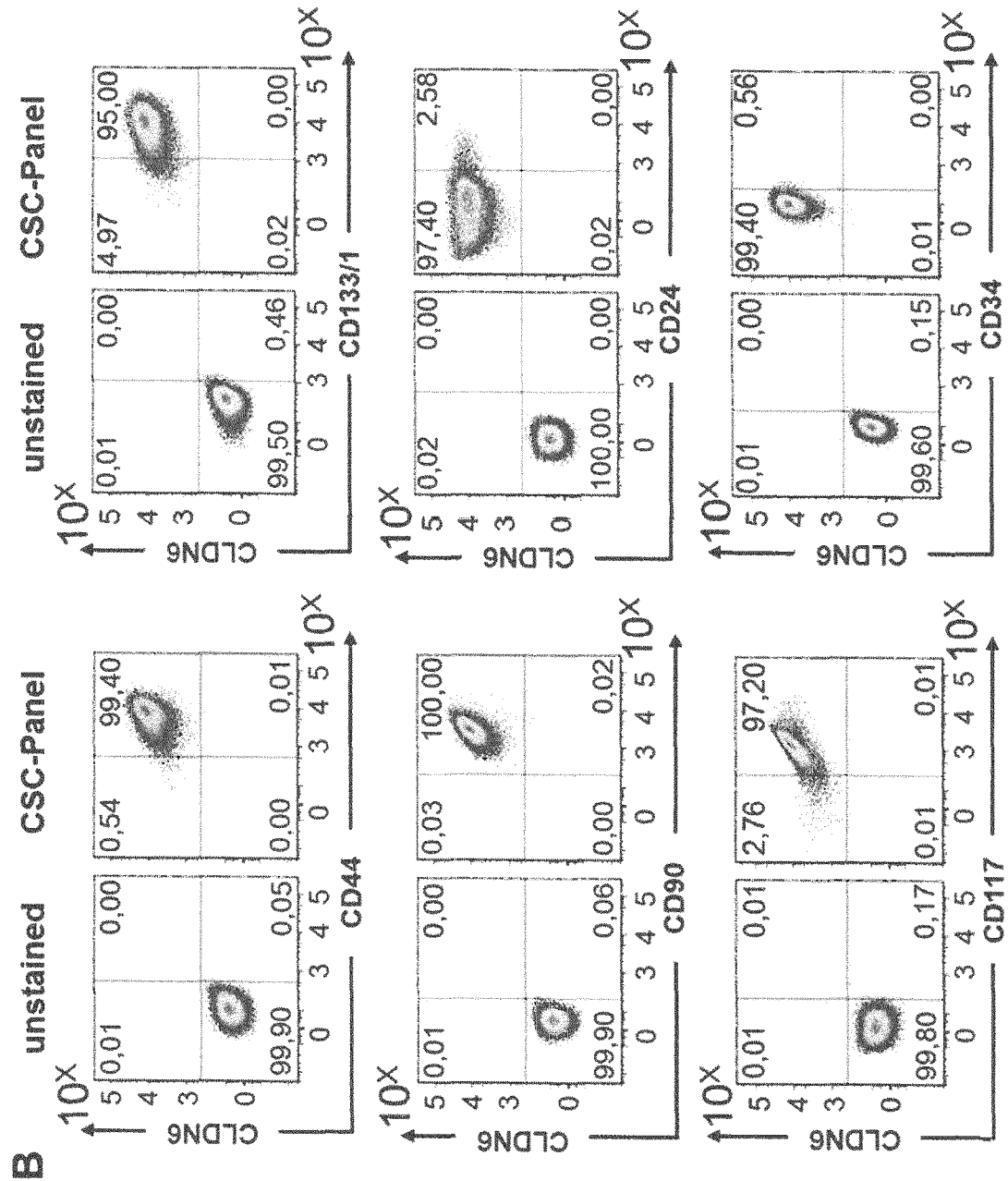
Figure 7:
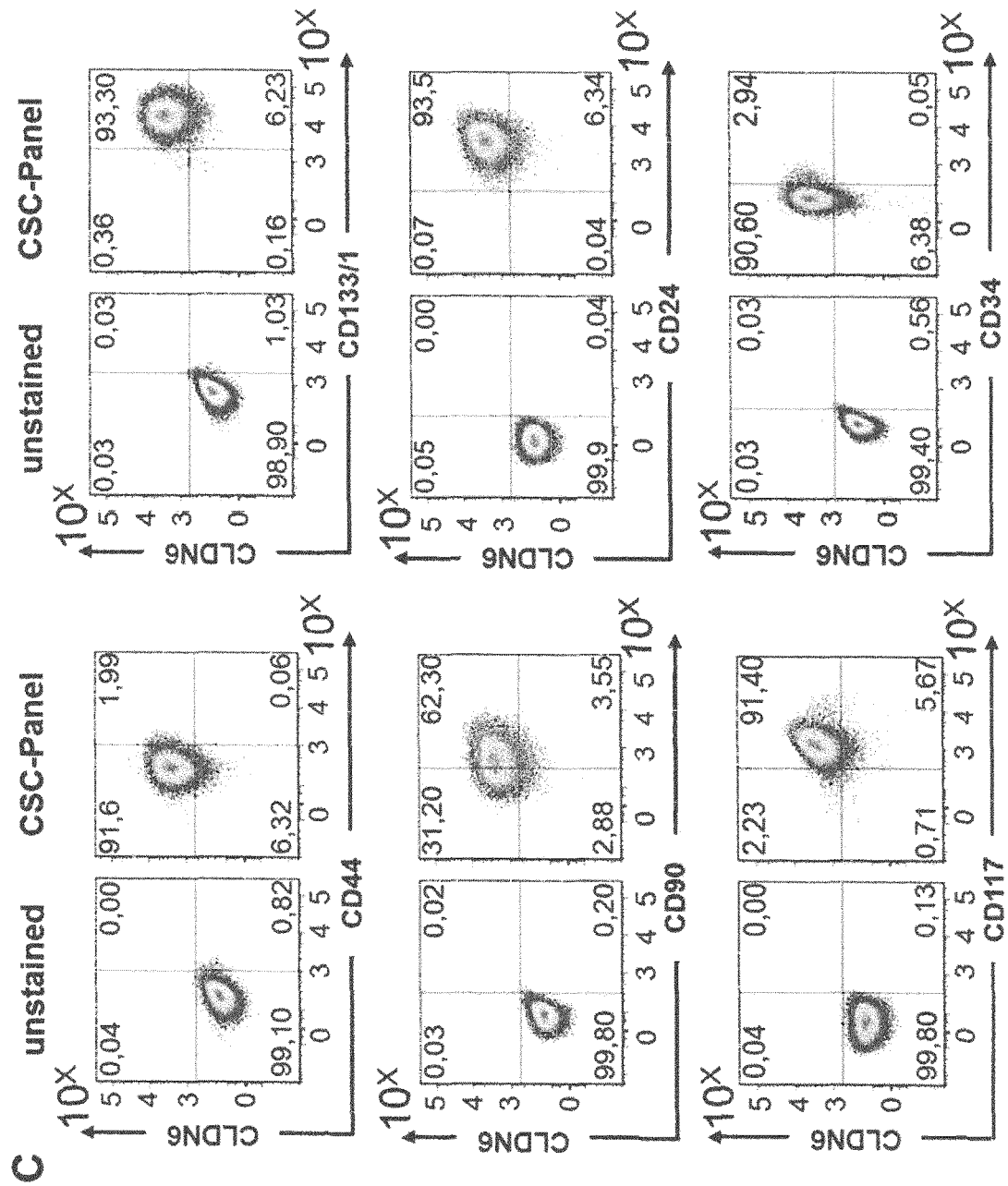
Figure 7:
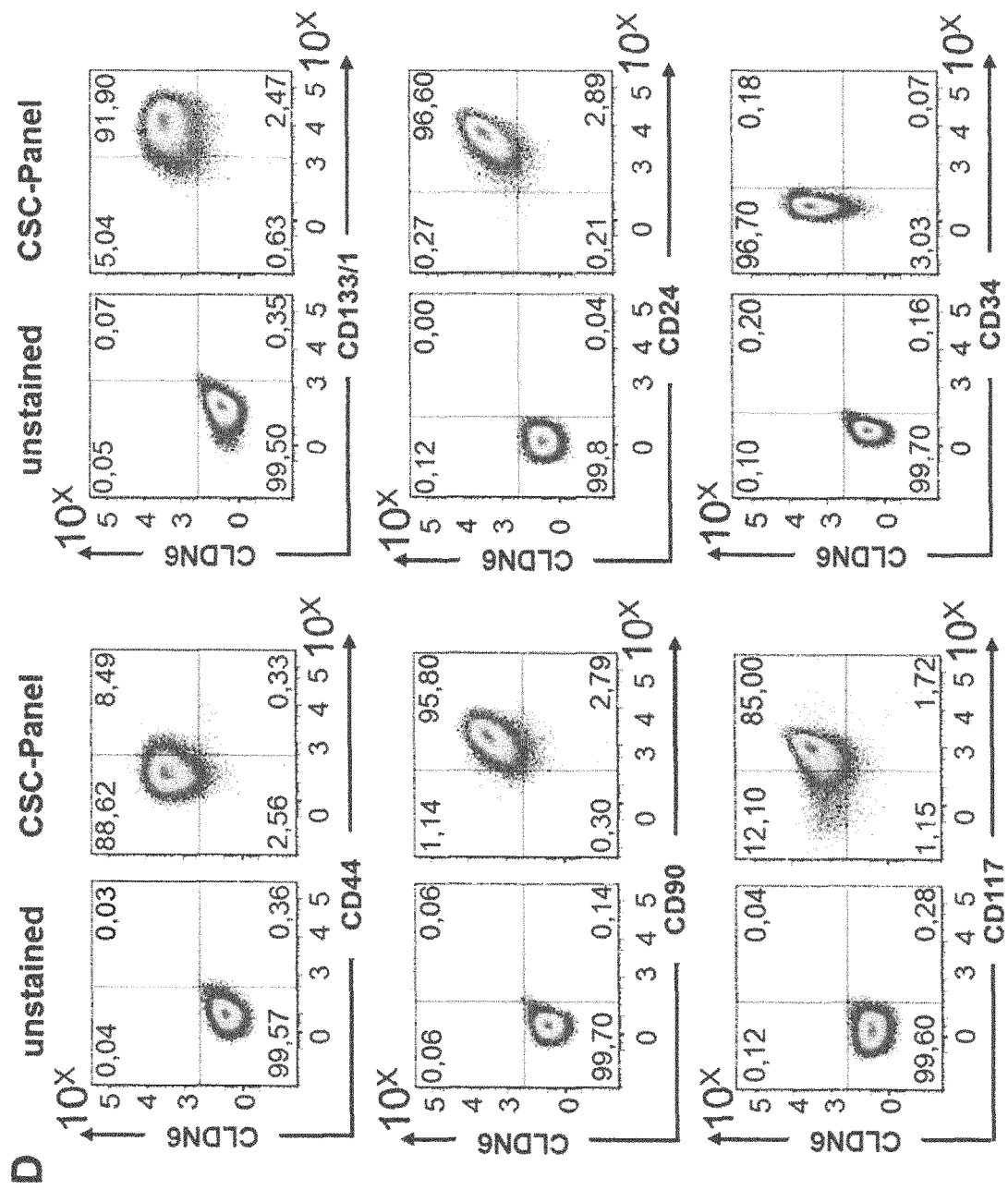

FIG. 7: CLDN6 high expressing cell lines show an enrichment of CSC markers compared to CLDN6 low expressing cells.

1E6 cells of the CLDN6-high expressing ovarian cancer cell lines OV90 (A) and PA-1 (B) or testis carcinoma cell lines NEC-8 (C) and NEC-14 (D) were stained for 30 min at 4° C. with antibodies against the different surface markers according to the FACS panel shown in Table 1 and CSC marker expression was analyzed by flow cytometry. Experiments were performed in triplicates and representative dot plots are shown.

Figure 8:
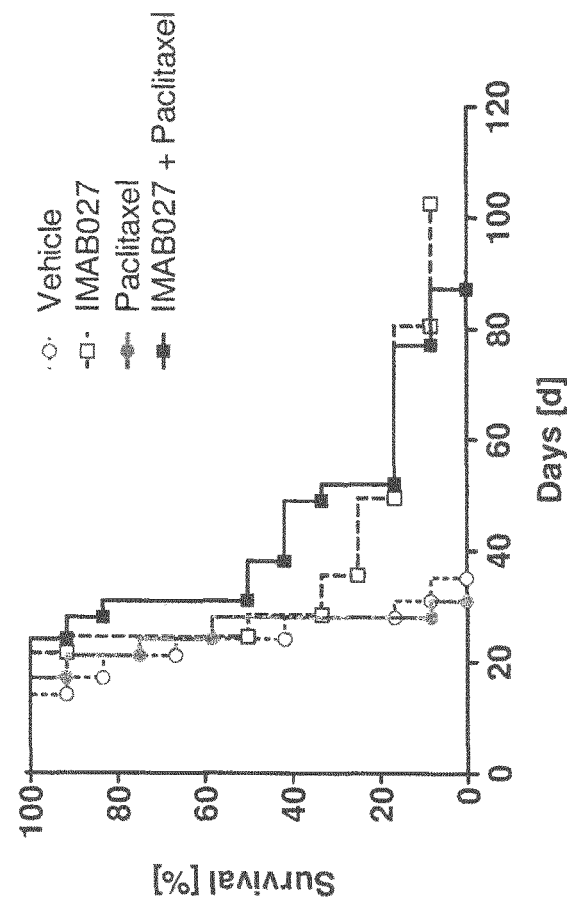
Figure 8:
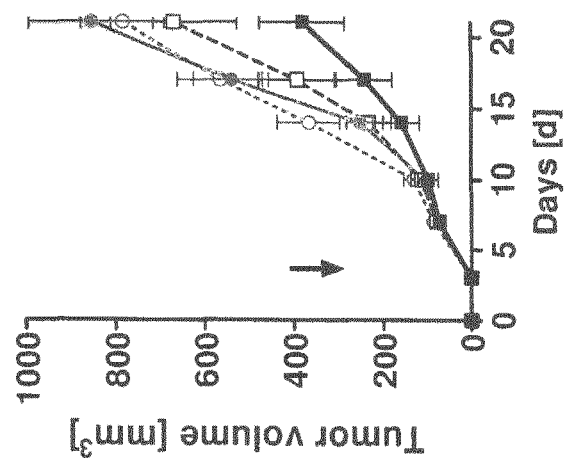

FIG. 8: Anti-tumoral effect of IMAB027 in combination with paclitaxel in an early xenograft tumor model.

Subcutaneous human ES-2 xenograft tumors ectopically expressing human CLDN6 were treated with 15 mg/kg paclitaxel on day 3, 10 and 17 post graft by i.p. injections. Antibody maintenance therapy started on day 4 with three 35 mg/kg IMAB027 injections per week (alternating i.v./i.p/i.p.). (A) Mean tumor growth kinetic (+SEM) after treatment with IMAB027 (white square), paclitaxel (grey circle), IMAB027 in combination with paclitaxel (black square) or the vehicle control (white circle). The arrow marks the time point of therapy start. (B) Survival curves of treated mice. Group size: n=12.

Figure 9:
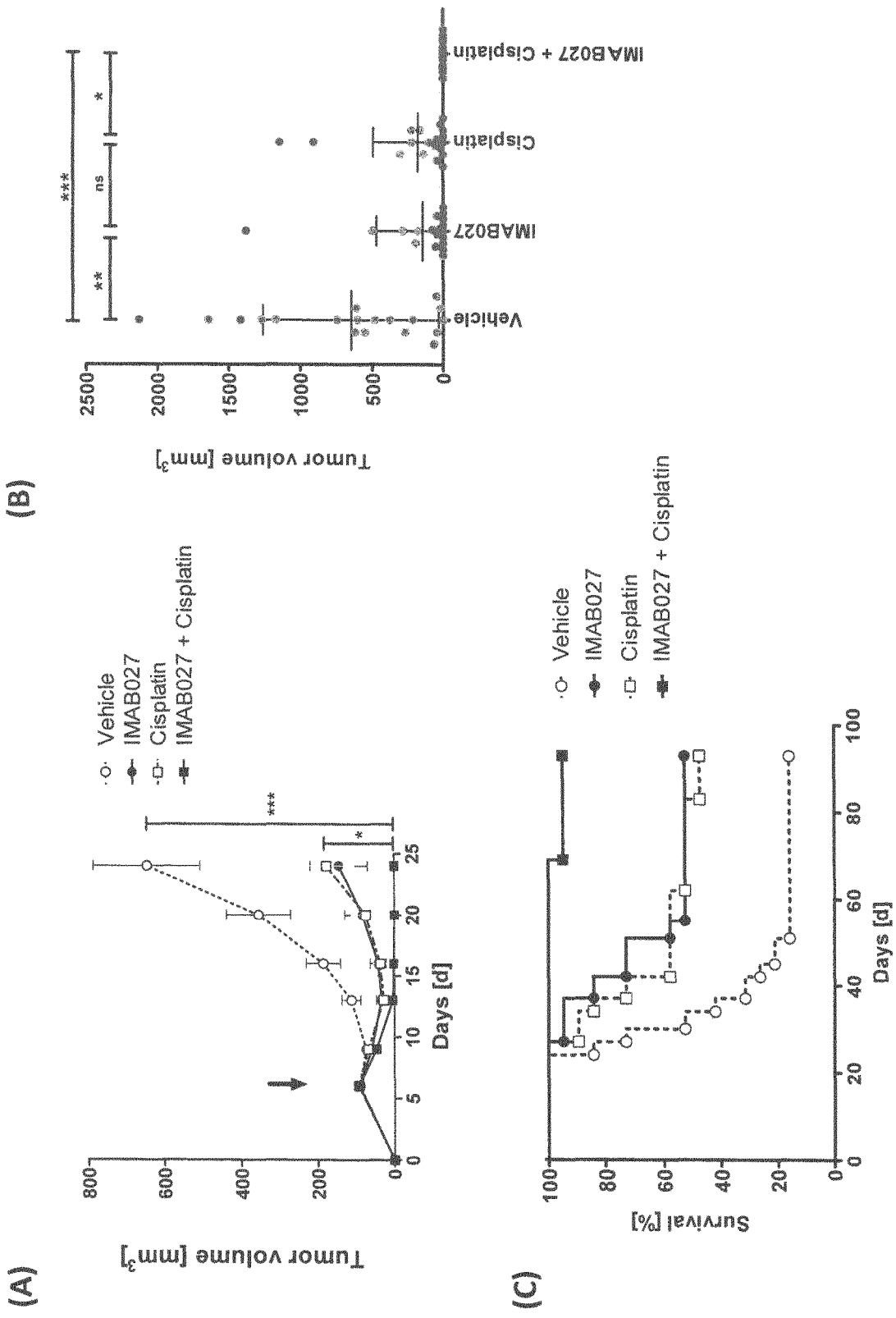

FIG. 9: Anti-tumoral effect of IMAB027 in combination with cisplatin in an advanced xenograft tumor model.

Subcutaneous human NEC14 xenograft tumors were grown to a median size of ~100 mm$^3$ before the beginning of the treatment. Mice were treated with 1 mg/kg cisplatin by i.p. injections daily from day 6 to 10 post engraftment and with three 35 mg/kg IMAB027 injections per week (alternating i.v./i.p./i.p.) starting on day 6 as maintenance therapy. (A) Mean tumor growth kinetic (±SEM) after treatment with IMAB027 (solid circle), cisplatin (open square), IMAB027 in combination with cisplatin (solid square) or the vehicle control (open circle). The arrow marks the time point of therapy start. (B) Individual tumor size in mice at day 24 post graft (mean with ±standard diviation). (C) Survival curves of treated mice. Group size: n=19. P-values: *, $p<0.05$; , $p<0.01$ and *, $p<0.001$.

Figure 10:
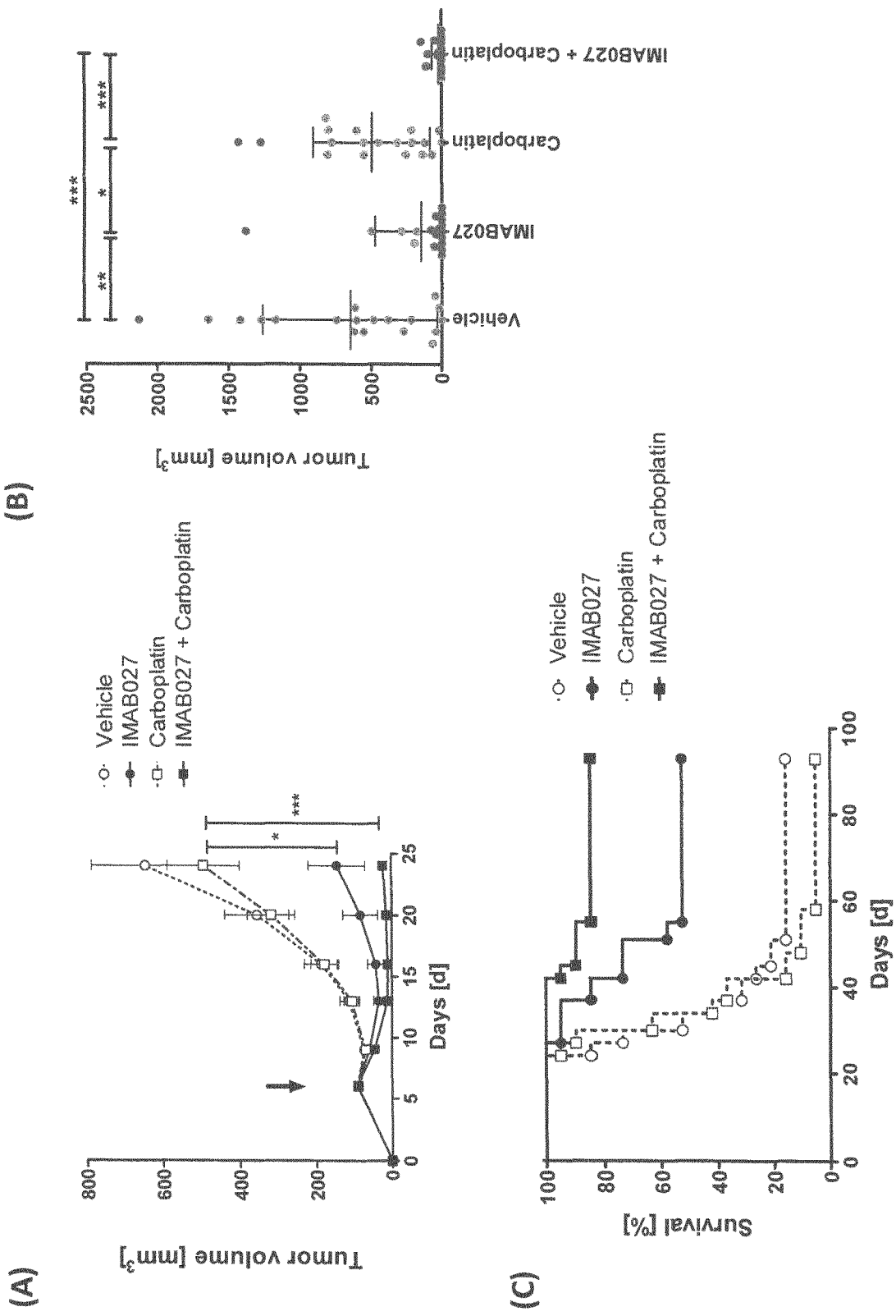

FIG. 10: Anti-tumoral effect of IMAB027 in combination with carboplatin in an advanced xenograft tumor model.

Advanced human NEC14 xenograft tumors were treated with IMAB027 alone or in combination with a cytostatic drug as described in FIG. 9. Instead of cisplatin, mice were treated with 30 mg/kg carboplatin on days 6, 13 and 20 by bolus i.p. injections. (A) Mean tumor growth kinetic (±SEM) after treatment with IMAB027 (solid circle), carboplatin (open square), IMAB027 in combination with carboplatin (solid square) or the vehicle control (open circle). The arrow marks the time point of therapy start. (B) Individual tumor size in mice at day 24 post graft (mean with ±standard diviation). (C) Survival curves of treated mice. Group size: n=19. P-values: *, $p<0.05$; , $p<0.01$ and *, $p<0.001$.

Figure 11:
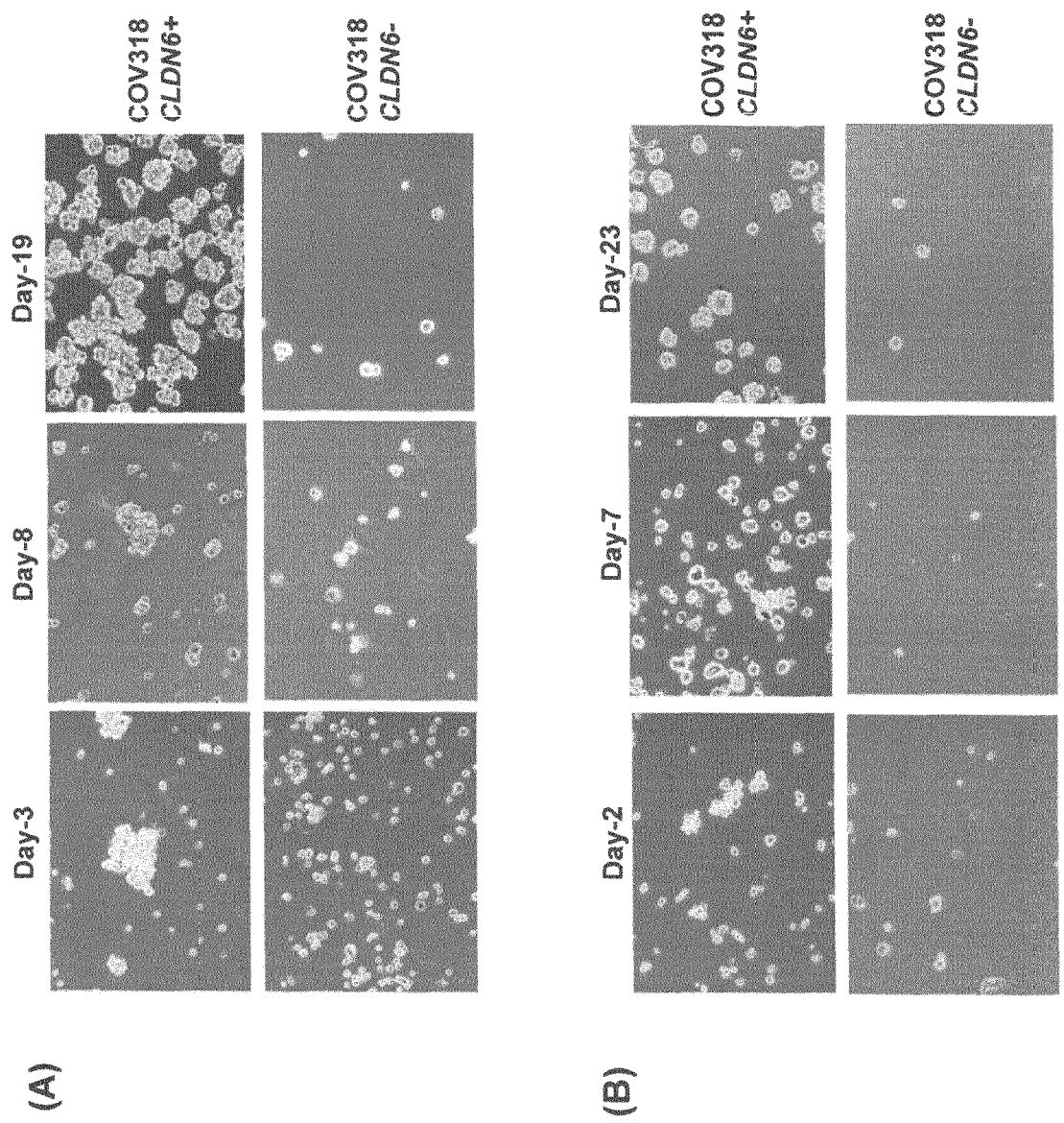

FIG. 11: CLDN6 is important for the spheres forming behavior of ovarian cancer cells.

To analyze the impact of CLDN6 on sphere formation, CLDN6 positive and CLDN6 negative COV318 cells were isolated by fluorescence activated cell sorting after staining with 0.5 µg/ml IMAB027. CLDN6 positive and CLDN6 negative COV318 cells were grown in ultra low attachment plates under sphere formation conditions (serum-free DMEM/F12 medium containing 0.4% bovine serum albumin, 20 ng/ml basic fibroblast growth factor, 10 ng/ml epidermal growth factor and 5 µg/ml insulin). (A) Representative pictures of first generation spheres of CLDN6 positive (CLDN6+) and CLDN6 negative (CLDN6-) COV318 cells at day 3, 8 and 19 post sort. (B) Representative pictures of second generation spheres obtained from single cells of CLDN6+ first generation spheres from (A) at day 22 post sort.

Figure 12:
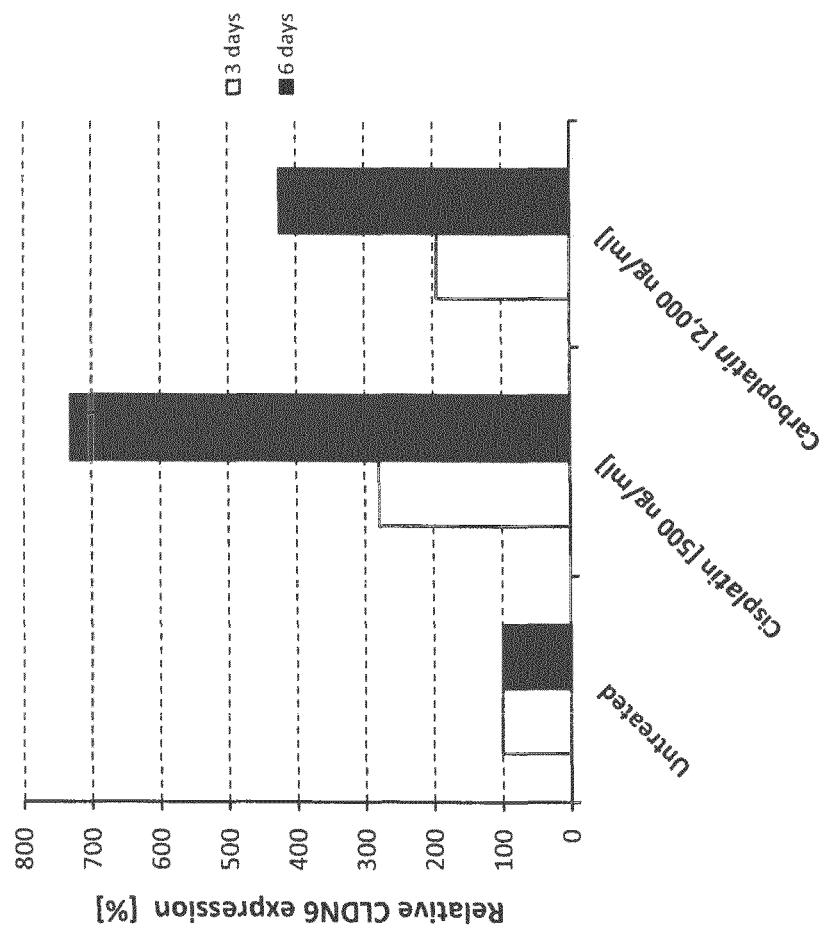

FIG. 12: Enrichment of CLDN6-positive cells after treatment with platin-derivatives.

COV318 cells were treated with 500 ng/ml cisplatin or 2,000 ng/ml carboplatin for 4 days. After treatment, cells were grown in the absence of cytostatic drugs for additional 3 days (white bars) and 6 days (black bars), respectively. The expression of CLDN6 was analyzed by flow cytometry using the CLDN6 specific antibody IMAB027 and an isotype control antibody. Expression of treated COV318 cells is shown relative to untreated cells. For evaluation, values of the isotype control were subtracted from CLDN6 staining.

Figure 13:
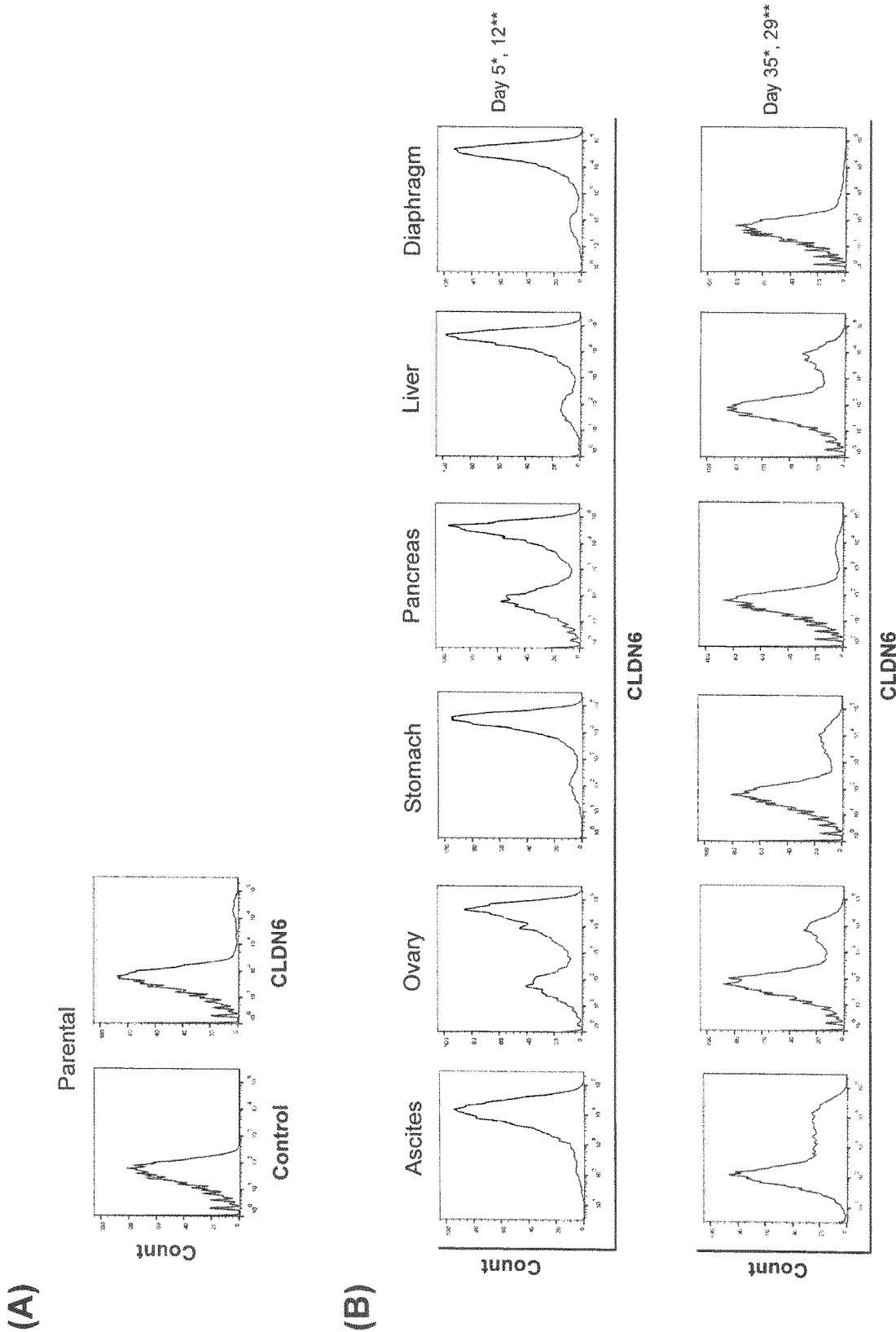

FIG. 13: Enrichment of CLDN-positive cells after intraperitoneal engraftment.

COV318 cells were injected intraperitoneally in athymic nude mice. Mice which developed ascites were euthanized, and both ascites and solid tumors were collected for further characterization. Isolated cells were analyzed for CLDN6 expression immediately after preparation and after they have been maintained in culture for several passages. (A) Flow cytometric analysis of CLDN6 expression on parental COV318 cells using the CLDN6 specific antibody IMAB027 and an isotype control. (B) CLDN6 expression on cells derived from ascites and solid tumors from ovary, liver, stomach, pancreas and diaphragm at different time points after isolation (*: ascites on days 5 and 35; **: solid tumors on days 12 and 29). Fluorescence intensity is displayed on the X-axis. The count of events displayed on the Y-axis is scaled as a percentage of the maximum count for events.

Figure 14:
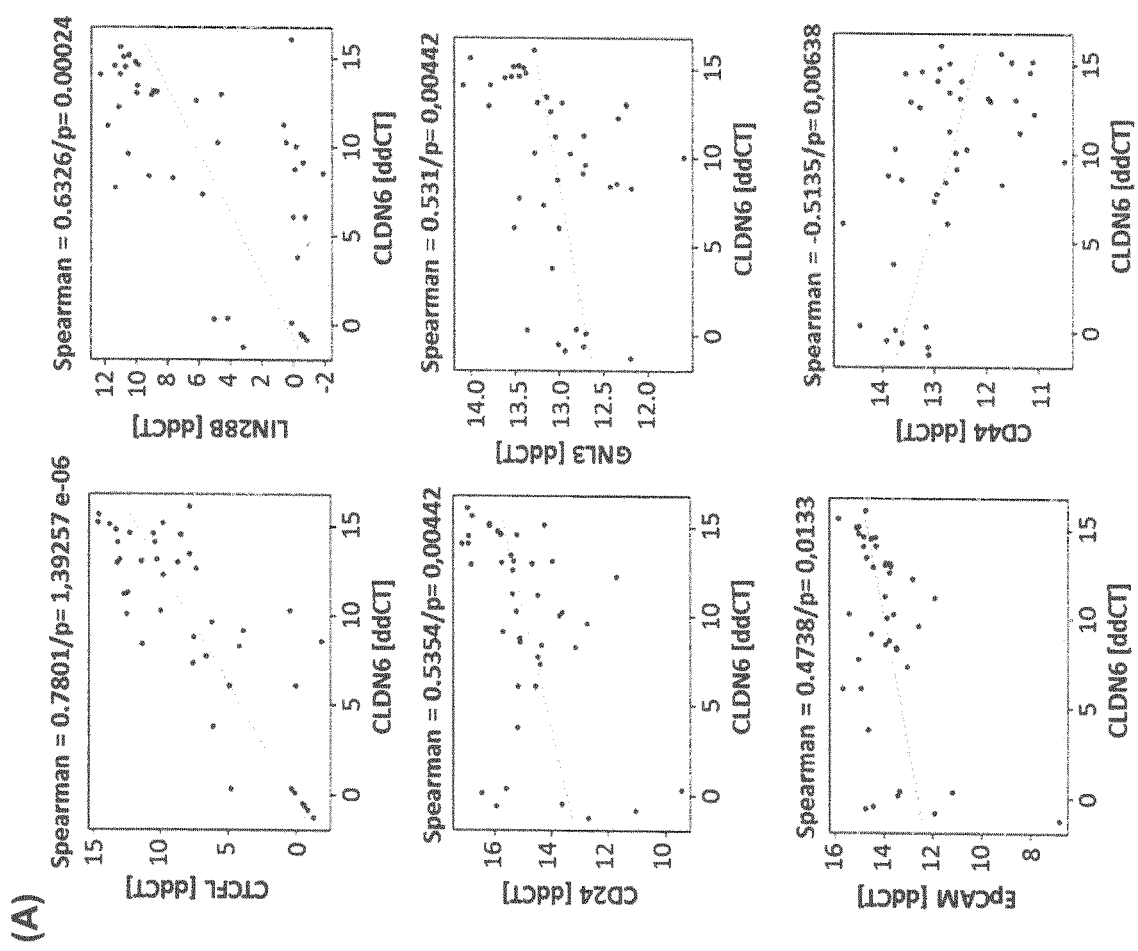

FIG. 14: CLDN6 correlates with ovarian cancer stem cell markers in primary tumor samples.

42 ovarian cancer samples were analyzed for their mRNA expression levels of CLDN6 and a variety of described ovarian cancer stem cell markers by qRT-PCR using a Fluidigm detection system and software. Spearman correlation analysis was performed to analyze CLDN6 correlation with the cancer stem cell specific markers. In (A) scatter plots of significant correlations are shown (P-values≤0.05). In (B) a summary of all correlations is shown.

Figure 15:
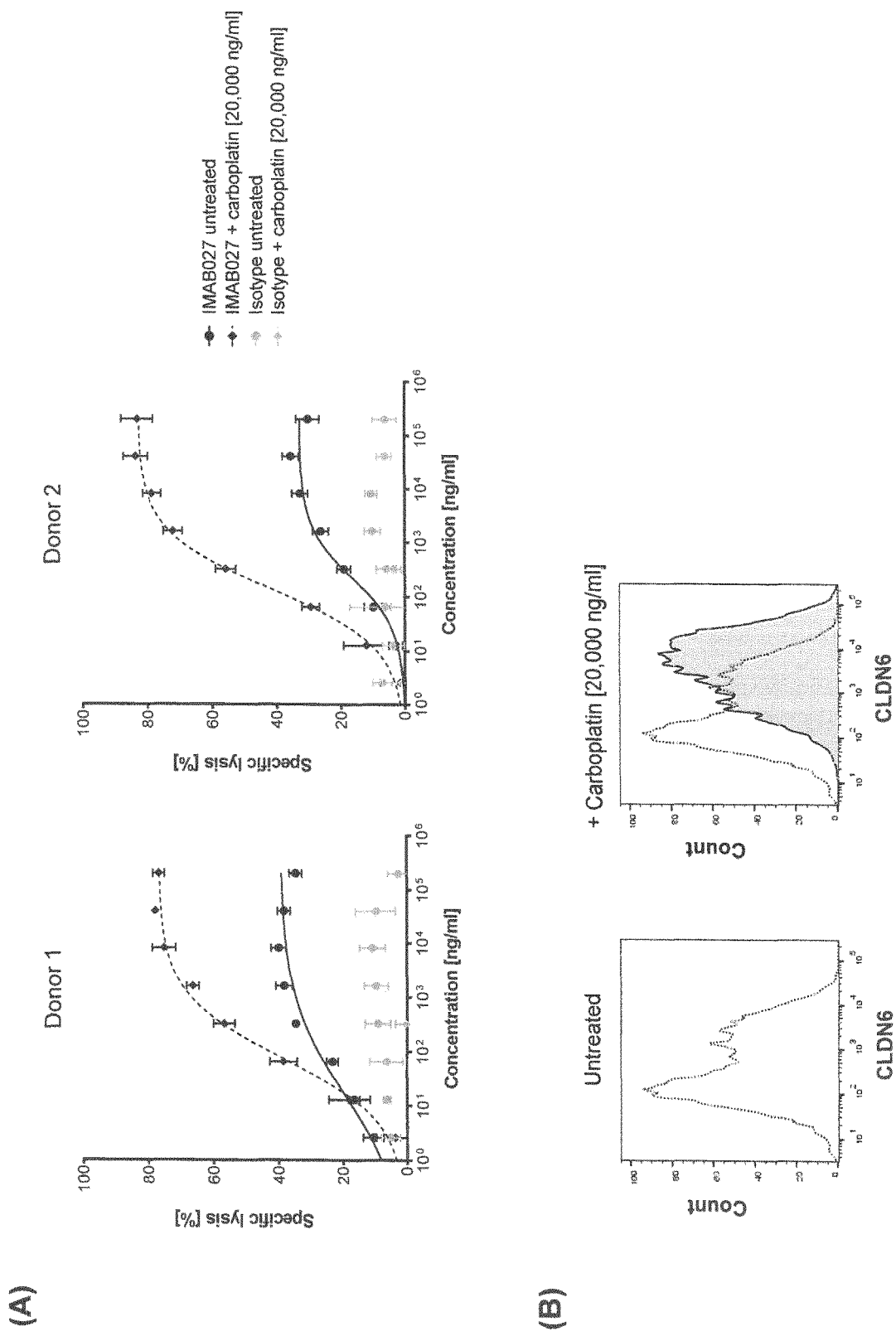
Figure 15:
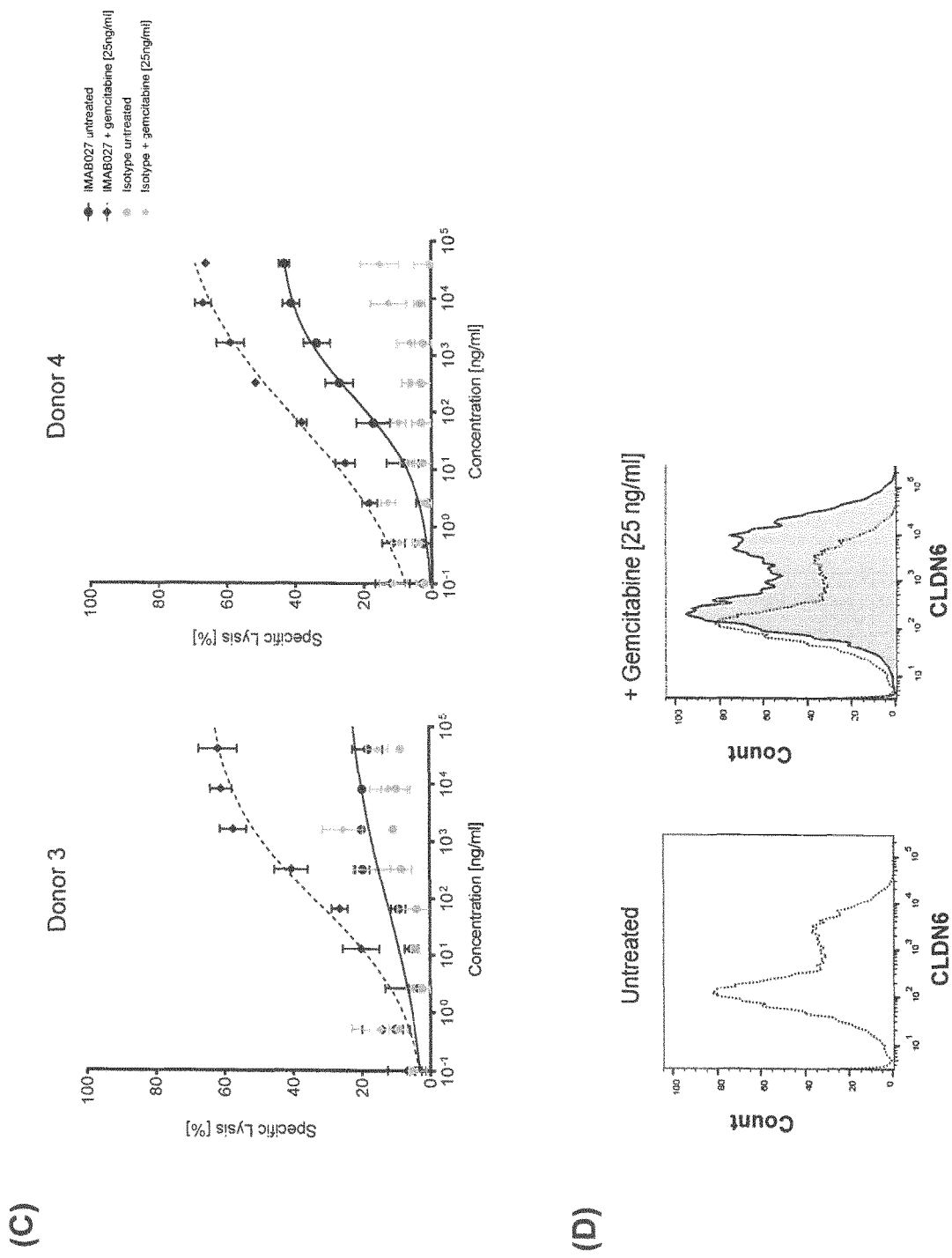
Figure 15:
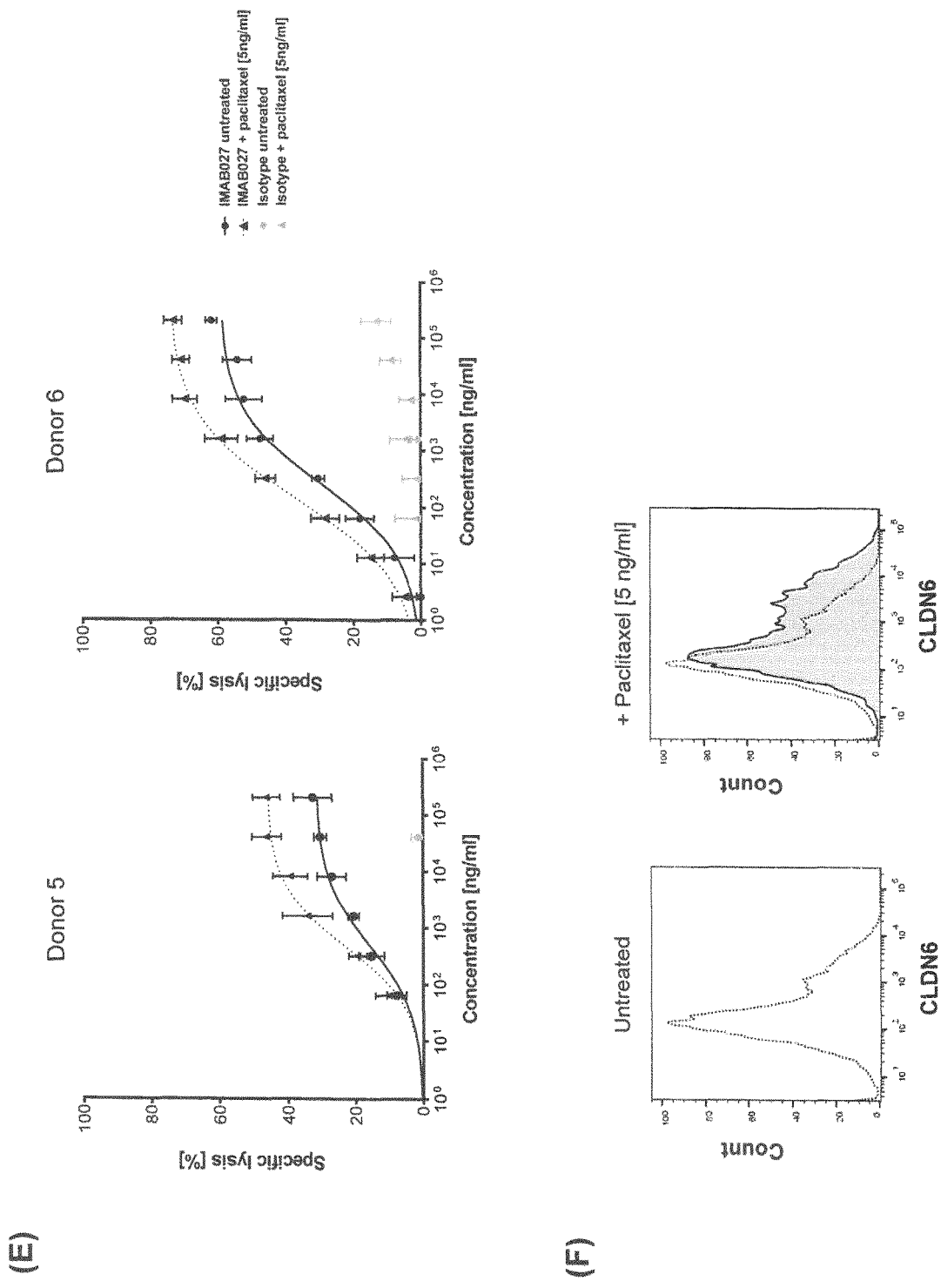
Figure 15:
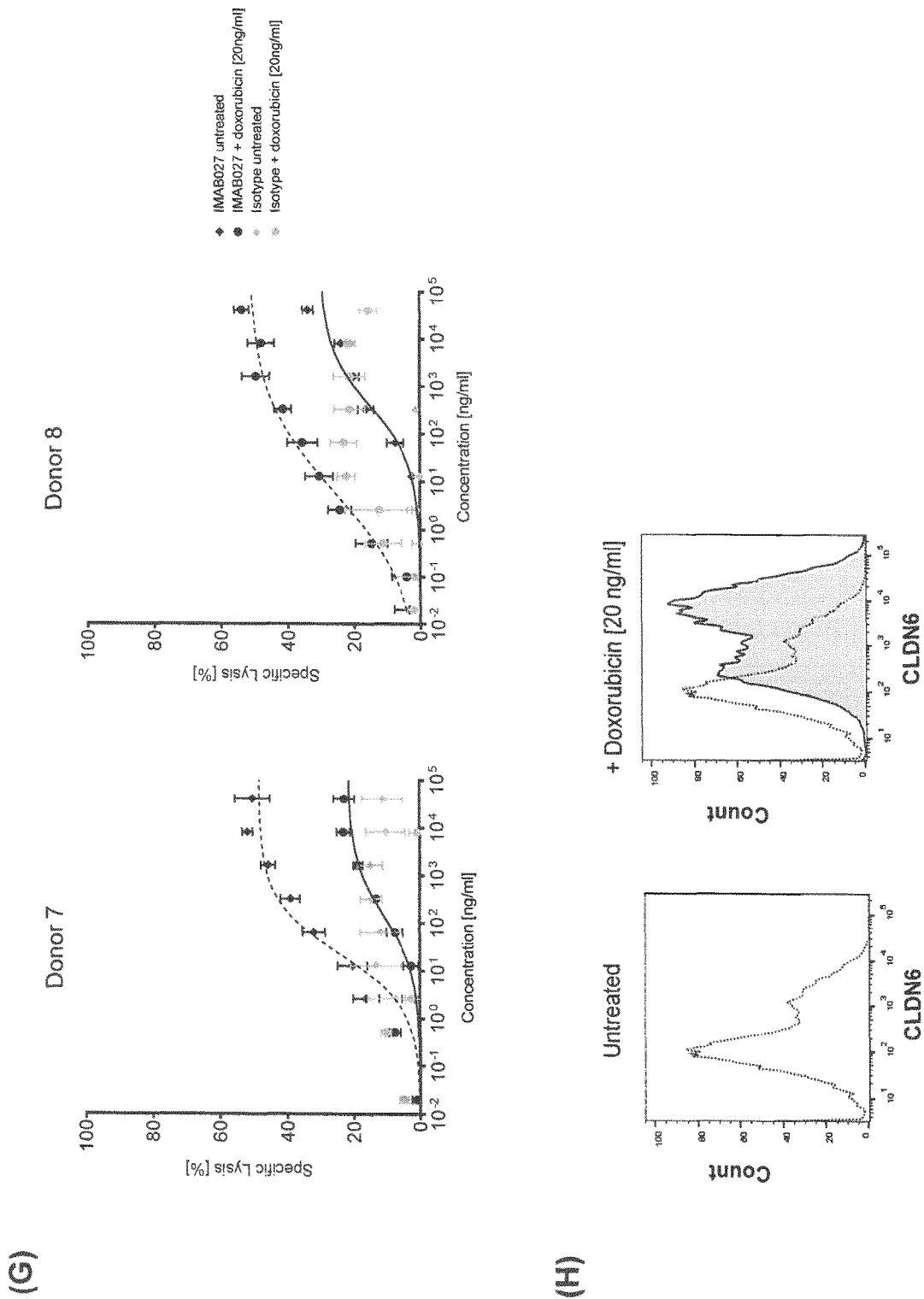
Figure 15:
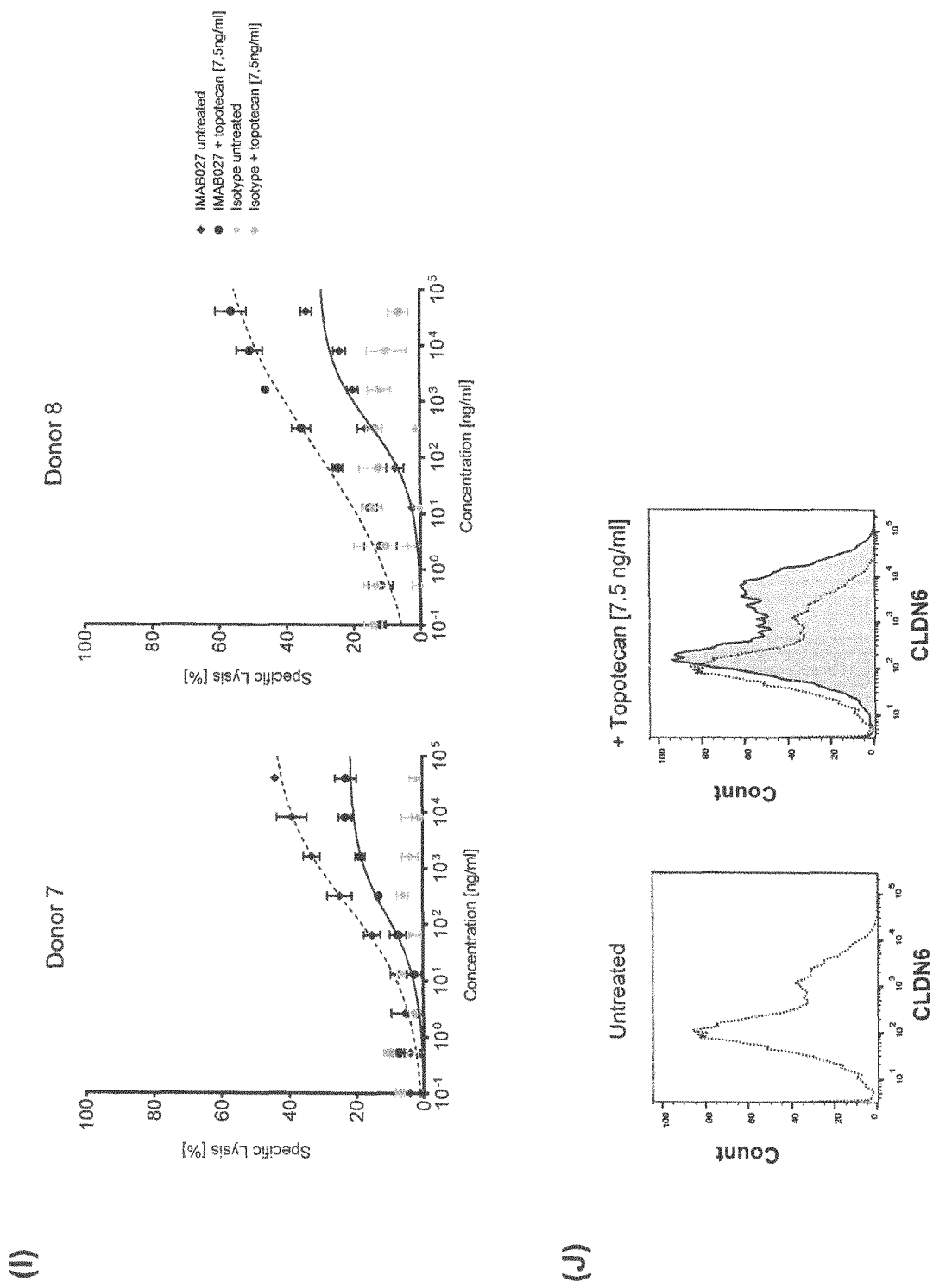

FIG. 15: IMAB027-mediated ADCC after treatment with carboplatin and paclitaxel.

ADCC activity of IMAB027 in combination with chemotherapy was analyzed using COV362(Luc) target cells. Therefore, cells were treated for 4 days with carboplatin, gemcitabine, paclitaxel, doxorubicin or topotecan at indicated concentrations. After treatment, cells were grown for 3 (A-D) and 10 days (E-J) in the absence of cytostatic drugs, respectively. Control cells were cultured without cytostatics. (A, C, E, G, I) ADCC experiments were performed with IMAB027 (black lines) or an isotype control antibody (grey lines) using PBMC from healthy donors at an effector (PBMC) to target cell ratio of ~40:1. Data points (n=4 replicates) are depicted as mean±SD. (B, D, F, H, J) Expression of CLDN6 was analyzed by flow cytometry using IMAB027. Black dotted lines demonstrate CLDN6 expression in untreated cells, gray filled histograms represent CLDN6 expression after treatment.

Figure 16:
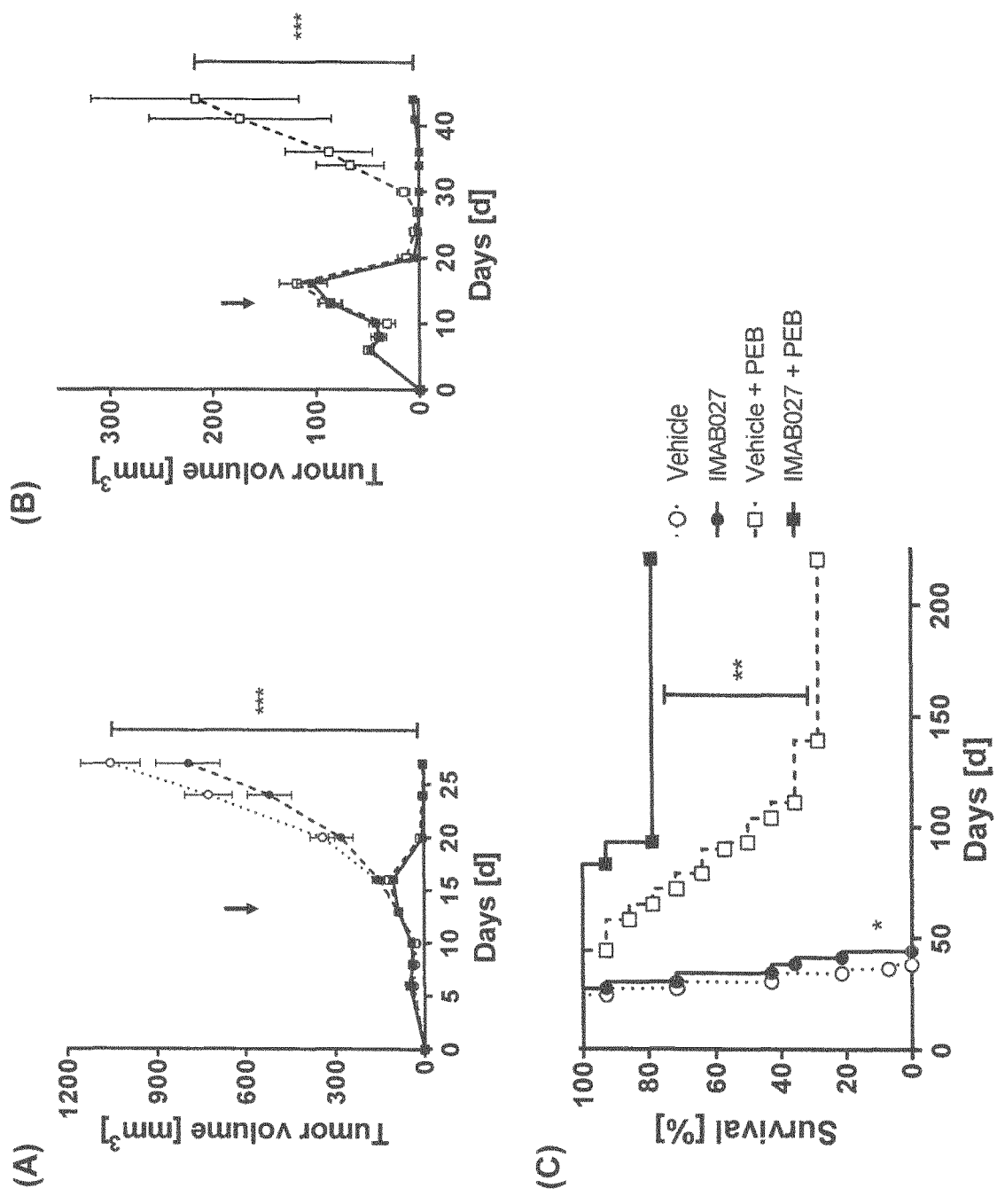

FIG. 16: Anti-tumoral effect of IMAB027 in combination with PEB treatment in a very advanced xenograft tumor model.

Subcutaneous human NEC14 xenograft tumors were grown in nude mice to a very advanced stage. Tumor therapy with PEB (cisplatin, etoposide and bleomycin) and IMAB027 started on day 13. Mice receiving the PEB regimen were treated with 1 mg/kg cisplatin and 5 mg/kg etoposide on day 13, 14, 15, 16 and 17 and with 10 mg/kg bleomycin on day 13, 17 and 21 by i.p. injections. The antibody IMAB027 was administered three times per week by alternating i.v./i.p./i.p. injections of 35 mg/kg from day 13 to 101 post graft. Vehicle control groups received 0.9% NaCl solution and drug substance buffer instead. Mice were monitored for 220 days in total. (A), (B) Mean tumor growth kinetic (±SEM) of untreated mice and mice treated with IMAB027, PEB or PEB in combination with IMAB027. The arrow marks the time point of therapy start (Dunn's multiple comparison test: ***, $p<0.001$). (C) Survival curves of untreated mice and mice treated with IMAB027, PEB or PEB in combination with IMAB027 (Mantel-Cox test: *, $p<0.05$; **, $p<0.01$). Group size: n=14.

Figure 17:
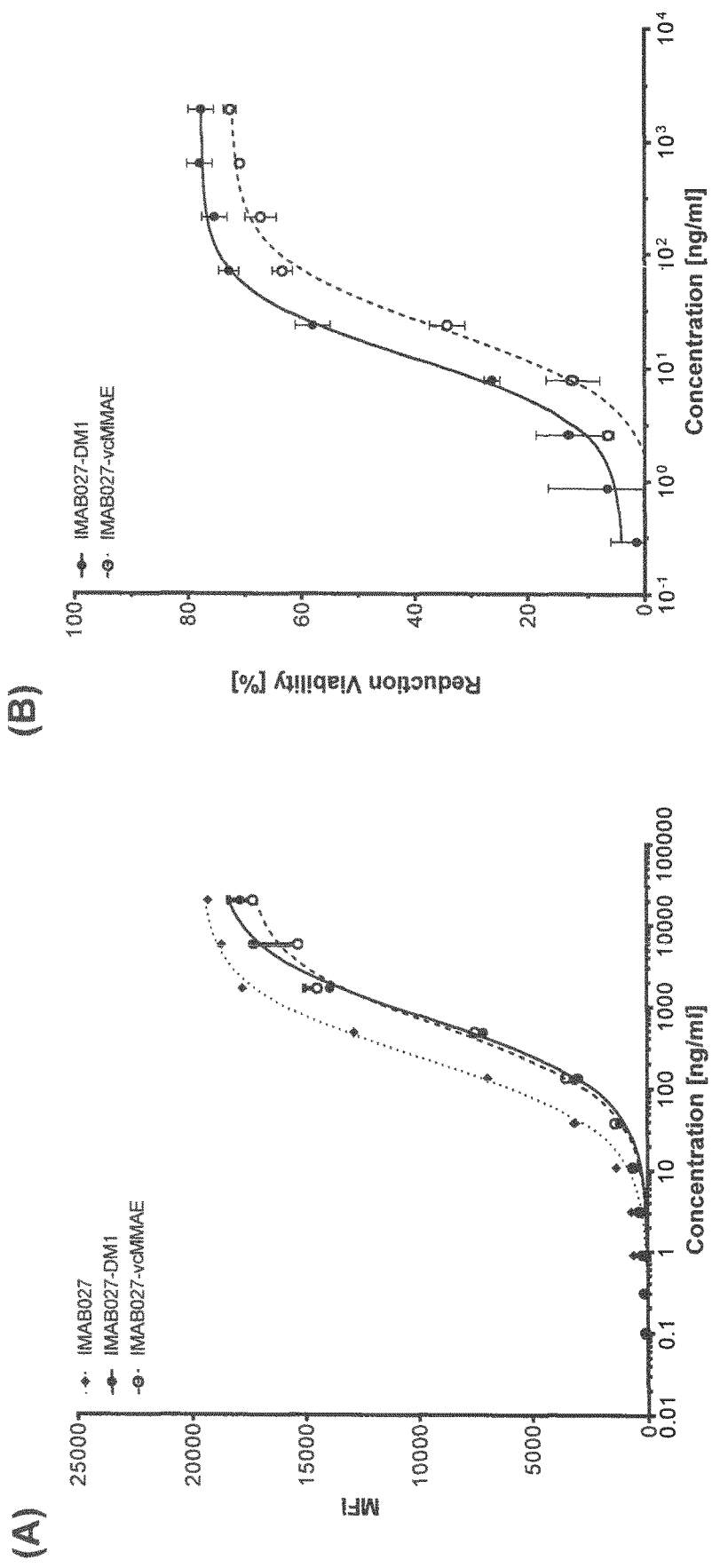

FIG. 17: Relative binding affinity and cytoxicity of IMAB27, IMAB027-DM1 and IMAB027-veMMAE.

(A) Binding of IMAB027, IMAB027-DM1 and IMAB027-vcMMAE was measured by flow cytometric analyses on endogenously CLDN6 expressing OV90 cells. (B) Dose-response curves of IMAB027-DM1 and IMAB027-vcMMAE mediated reduction of OV90 cell viability. Tumor cells were incubated for 72 h with IMAB027-DM1 or IMAB027-vcMMAE. The reduction of cell viability was measured using an XTT-based viability assay. Data points (n=3 replicates) are depicted as mean±SD. MFI: mean fluorescence intensity.

Figure 18:
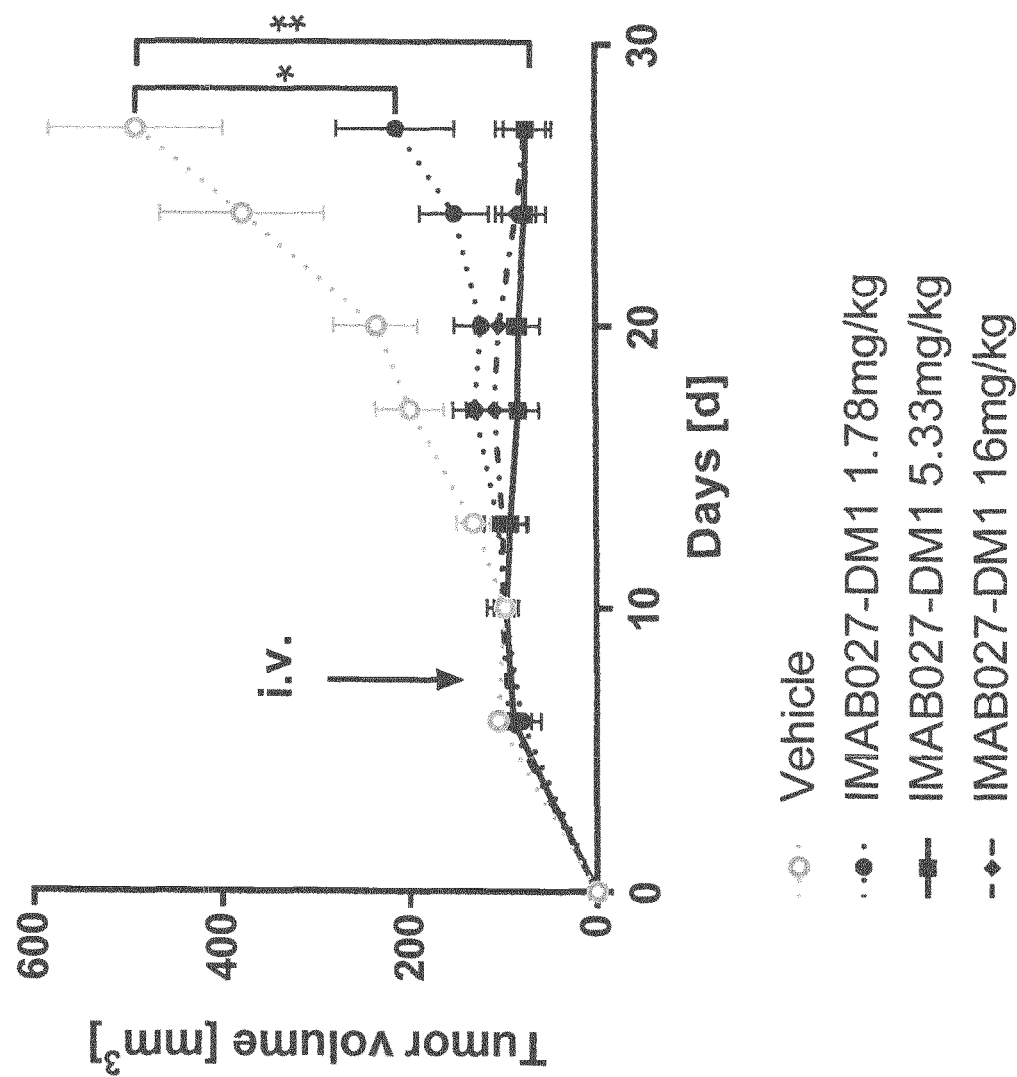

FIG. 18: Anti-tumoral effect of IMAB027-DM1 conjugates on advanced xenograft tumors.

Nude mice bearing established subcutaneous human OV90 xenograft tumors were treated 10 days post graft with intravenous single dose injections of 1.78, 5.33 or 16 mg/kg IMAB027-DM1 or vehicle control. The size of subcutaneous tumors was measured twice weekly (mean+SEM). Group size: n=5, *: $p<0.05$, **: $p<0.01$.

Figure 19:
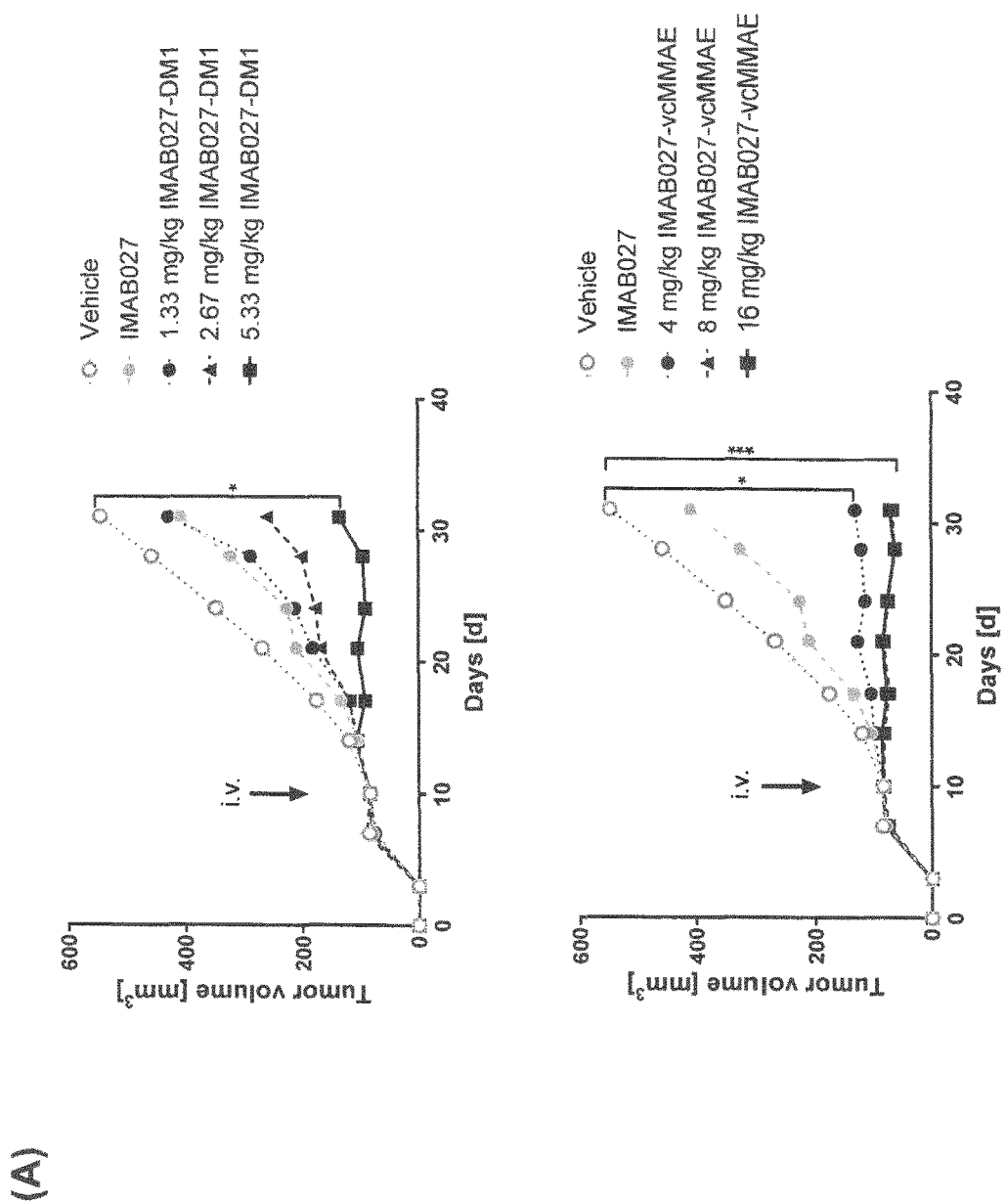
Figure 19:
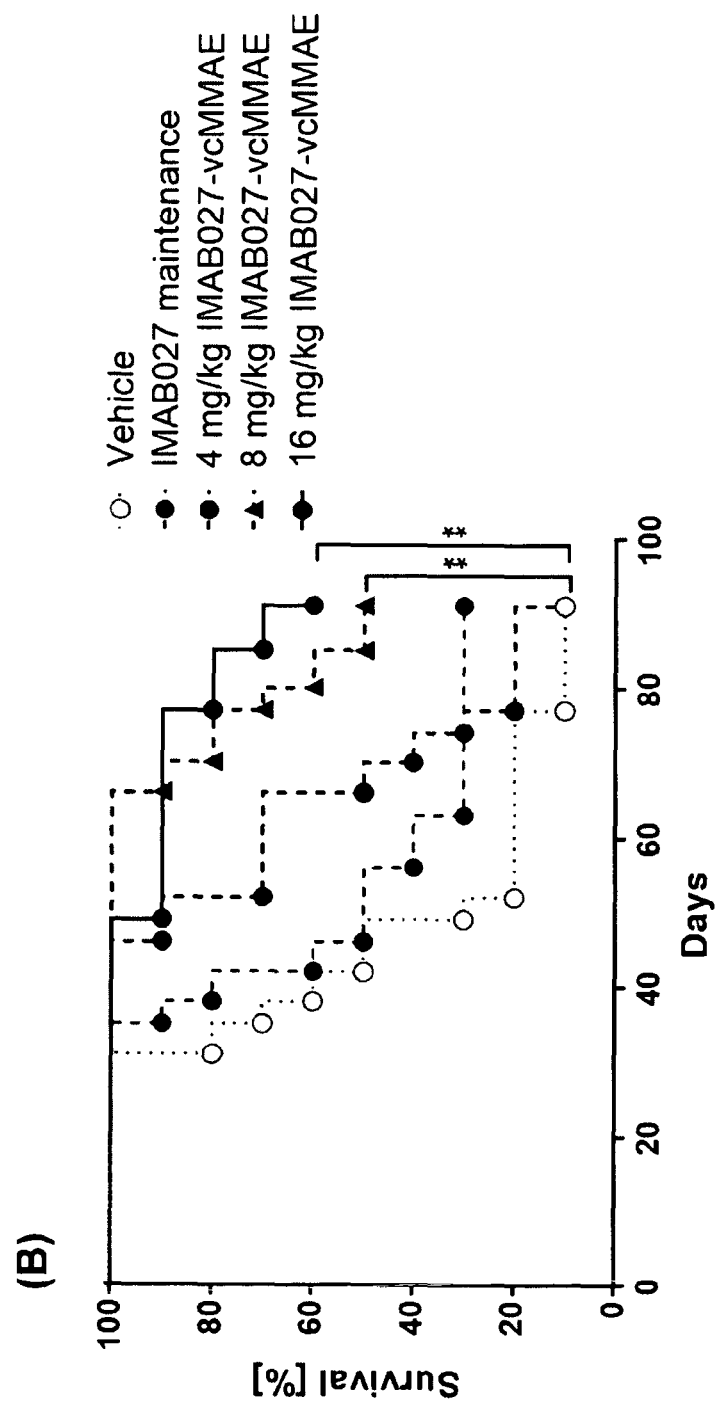

FIG. 19: Dose range finding of IMAB027-DM1 and IMAB027-vcMMAE conjugates on advanced OV90 xenograft tumors.

Nude mice with established subcutaneous human OV90 xenograft tumors were treated 10 days post graft with single dose intravenous injection of IMAB027-DM1, IMAB027-vcMMAE, vehicle or repeated dose injections of IMAB027. (A) Tumor growth of mice treated with 1.33, 2.67 or 5.33 mg/kg IMAB027-DM1 i.v. (top) or with 4, 8 or 16 mg/kg IMAB027-vcMMAE i.v. (bottom) compared to vehicle control and IMAB027 (35 mg/kg, weekly i.v./i.p./i.p.). The size of subcutaneous tumors was measured twice weekly (mean+SEM). (B) Kaplan-Meier survival curves of mice treated with vehicle or 4, 8 or 16 mg/kg IMAB027-vcMMAE. Mice were sacrificed when tumors reached a volume of 1400 mm$^3$ or if tumors became ulcerous. Group size: n=10, *: $p<0.05$, : $p<0.01$, *: $p<0.001$.

Figure 20:
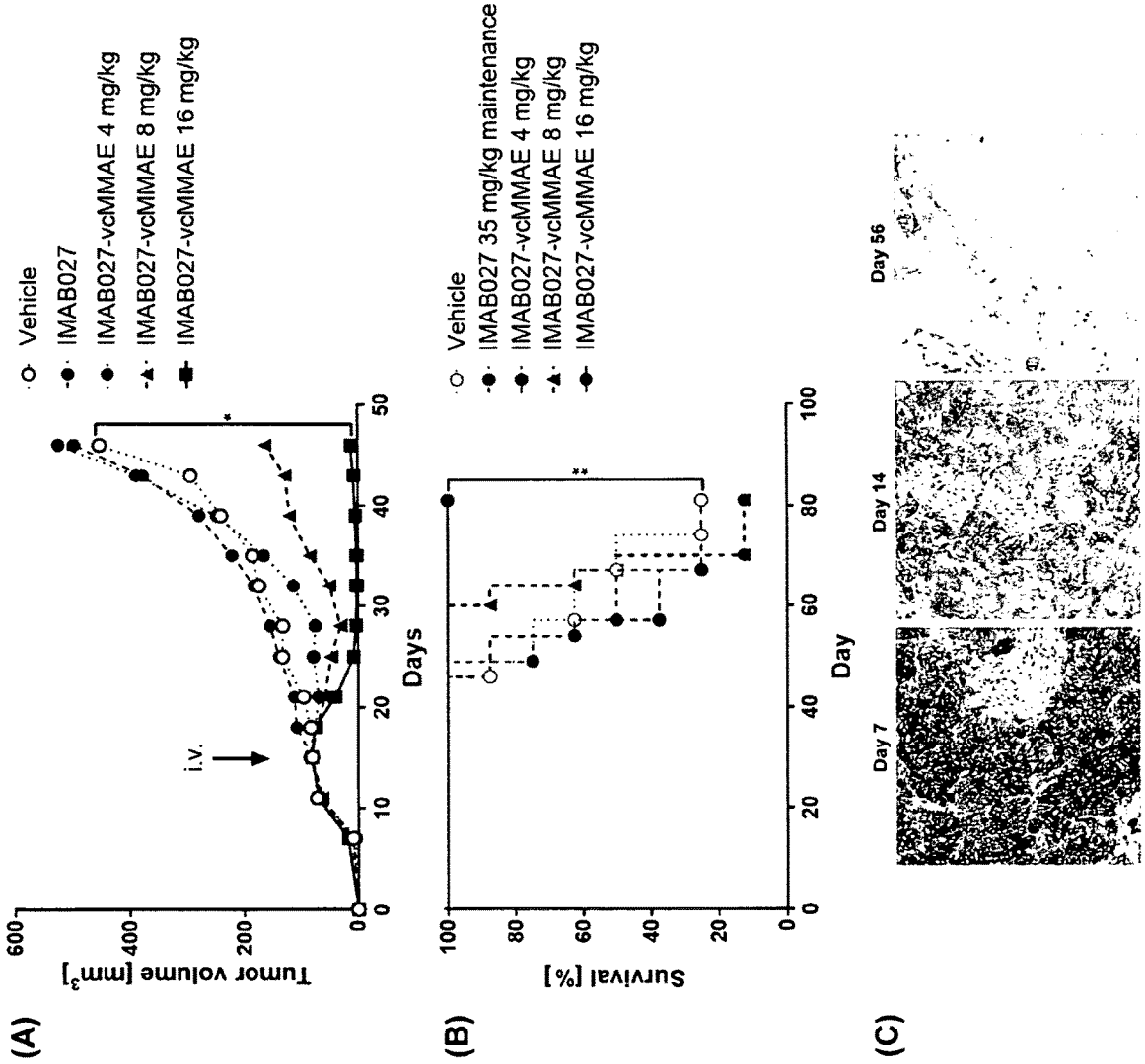

FIG. 20: Dose range finding of IMAB027-vcMMAE conjugates on advanced PA-1 xenograft tumors.

Nude mice with established subcutaneous human PA-1 xenograft tumors were treated 15 days post graft with single dose intravenous injection of IMAB027-vcMMAE, vehicle control or repeated dose injections of IMAB027. (A) Mean tumor growth (±SEM) and (B) Kaplan-Meier survival curves of mice treated with vehicle control, IMAB027 (35 mg/kg, weekly i.v./i.p./i.p.) or 4, 8 or 16 mg/kg IMAB027-vcMMAE. Mice were sacrificed when tumors reached a volume of 1400 mm$^3$ or if tumors became ulcerous. Group size: n=8, *: $p<0.05$, **: $p<0.01$, (C) Representative immunohistochemical staining against CLDN6 in PA-1 xenograft tumor sections at different time points post engraftment.

Figure 21:
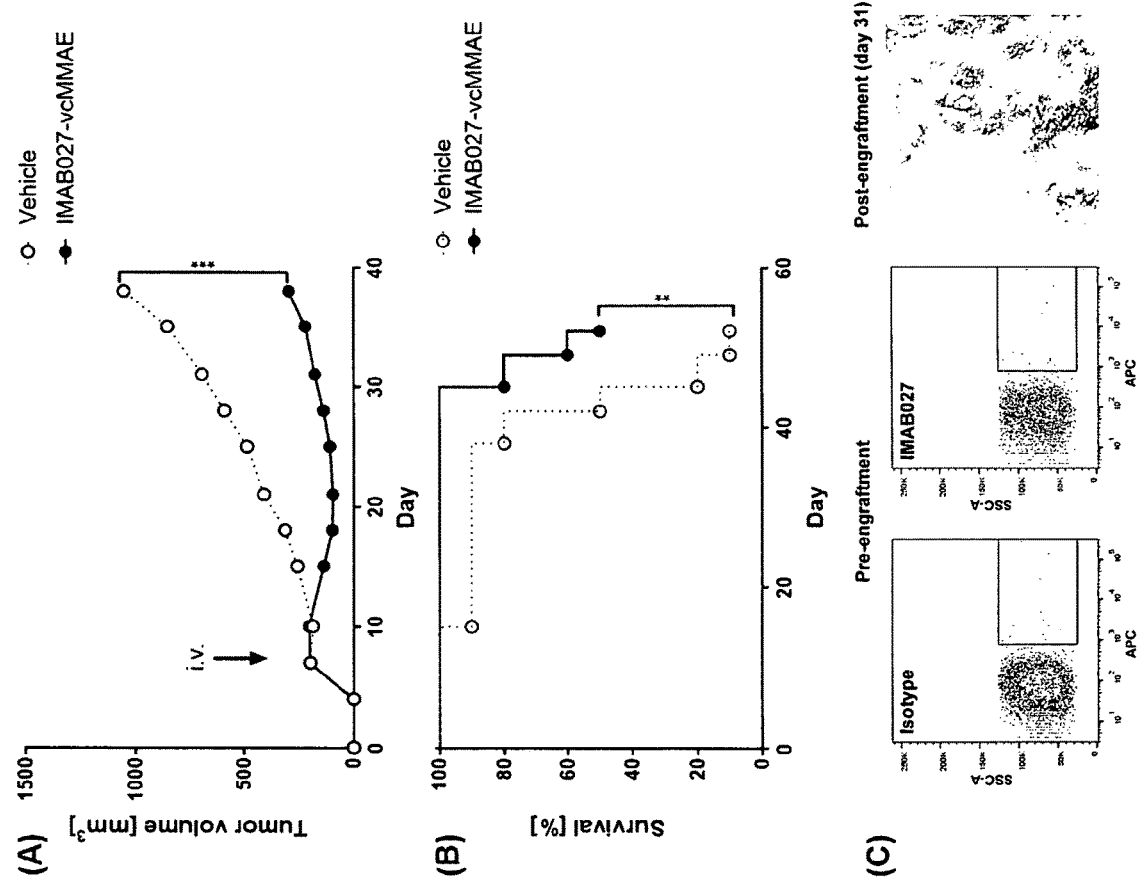

FIG. 21: Anti-tumoral effect of IMAB027-vcMMAE on advanced MKN74 xenograft tumors.

Nude mice with established subcutaneous human MKN74 xenograft tumors were treated 7 days post graft with an intravenous injection of 16 mg/kg IMAB027-vcMMAE or vehicle control. (A) Mean tumor growth (±SEM) and (B) Kaplan-Meier survival curves of mice treated with vehicle control or IMAB027-vcMMAE. Mice were sacrificed when tumors reached a volume of 1400 mm$^3$ or if tumors became ulcerous. Group size: n=10. (C) Flow cytometric analysis of CLDN6 expression on MKN74 tumor cells pre-engraftment and representative immunohistochemical staining of a non-treated MKN74 xenograft tumor at day 31 post-engraftment. : $p<0.01$, *: $p<0.001$.

Figure 22:
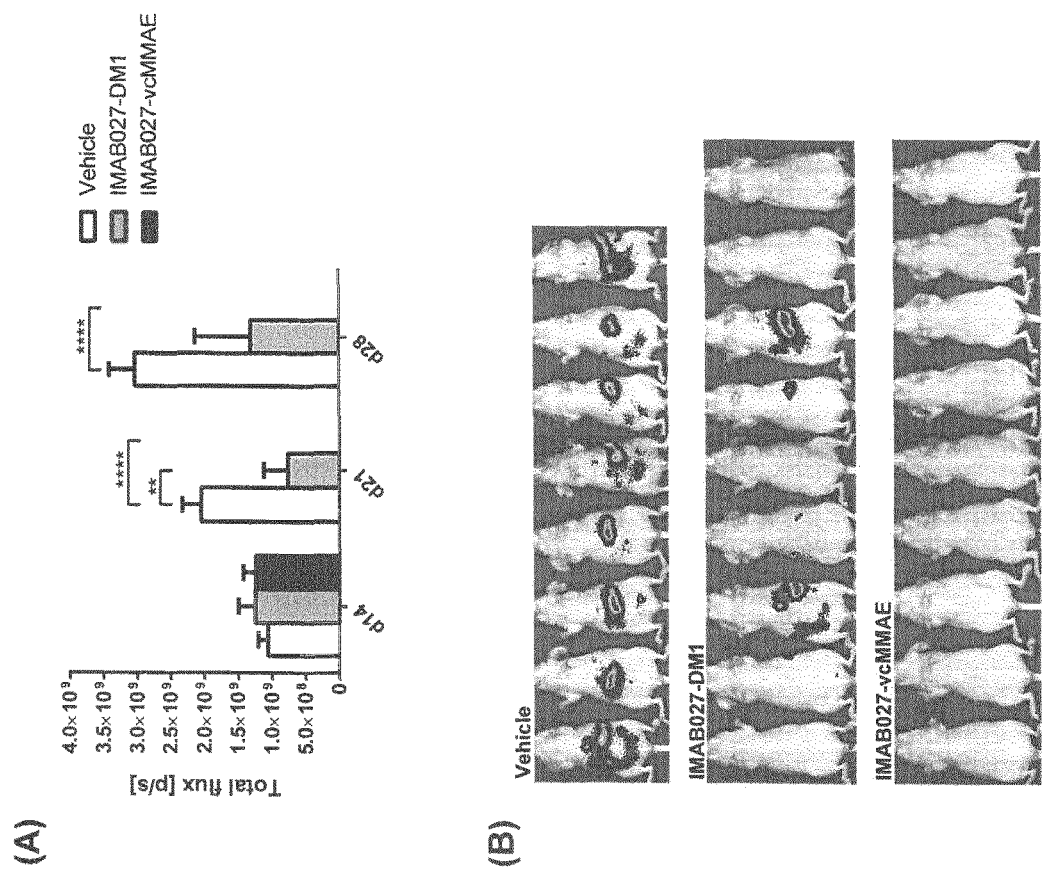

FIG. 22: Anti-tumoral effect of IMAB027-DM1 and IMAB027-veMMAE on advanced intraperitoneal metastatic human ovarian tumors.

Nude mice were engrafted intraperitoneally with the human ovarian carcinoma cell line PA-1(Luc) ectopically expressing luciferase. After the formation of intraperitoneal metastatic xenograft tumors, animals were treated with 16 mg/kg IMAB027-DM1, IMAB027-vcMMAE or vehicle control by i.p. injection on day 14 post graft. Growth of metastases was determined after luciferin administration by luminescence activity using an IVIS Lumina Imaging System. (A) Quantification of the metastasis load of mice treated with IMAB027-DM1, IMAB027-vcMMAE or vehicle. (B) In vivo whole body luminescence images of nude mice on day 28 post graft. Group size: n=8 (vehicle) or n=9 (IMAB027-DM1, IMAB027-vcMMAE), : p<0.01, **: p<0.0001.

Figure 23:
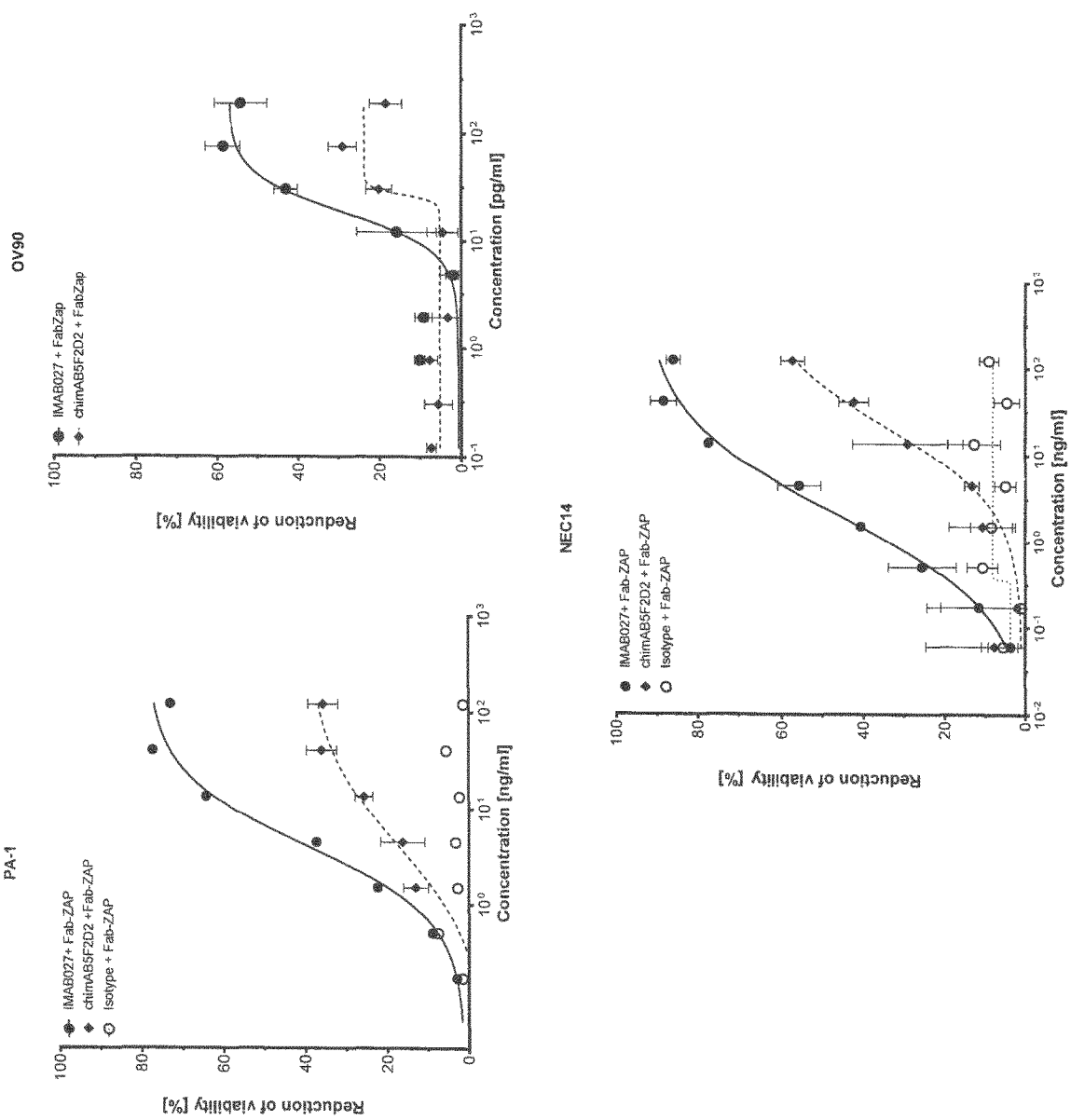

FIG. 23: Endocytosis of CLDN6 bound antibodies by human carcinoma cells.

Endocytosis of CLDN6 bound IMAB027, chimAB5F2D2 or isotype control antibodies was determined using a cytotoxicity based assay that depends on the co-internalization of the target bound antibodies and a saporin-conjugated anti-human IgG Fab fragment (FabZap). PA-1, OV90 or NEC14 human carcinoma cells were incubated for 72 h with IMAB027, chimAB5F2D2 or an isotype control antibody and the anti-human FabZap. (A) Dose-response curves of IMAB027/FabZap and chimAB5F2D2/FabZap mediated reduction of PA-1, OV90 and NEC14 cell viability, respectively. Data points (n=3 replicates) are depicted as mean±SD. (B) Comparison of IMAB027 normalized EC50 (rel EC50) and maximum (rel maximum) of flow cytometric binding and endocytosis.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family, such as CLDN6, are expressed in tumors of various origins, and are particularly suited as target structures in connection with antibody-mediated cancer immunotherapy due to their selective expression (no expression in a toxicity relevant normal tissue) and localization to the plasma membrane.

CLDN6 has been identified as differentially expressed in tumor tissues, with the only normal tissue expressing CLDN6 being placenta where low amounts of CLDN6 are detected on the RNA level. CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer.

In various embodiments of the invention, cancer diseases associated with CLDN6 expression include ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof. In one embodiment, the cancer disease associated with CLDN6 expression is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma.

The term "CLDN" as used herein means claudin and includes CLDN6. Preferably, a claudin is a human claudin.

The term "CLDN6" preferably relates to human CLDN6, and, in particular, to a protein comprising, preferably consisting of the amino acid sequence of SEQ ID NO: 1 or SEQ ID NO: 2 of the sequence listing or a variant of said amino acid sequence. The first extracellular loop of CLDN6 preferably comprises amino acids 28 to 80, more preferably amino acids 28 to 76 of the amino acid sequence shown in SEQ ID NO: 1 or the amino acid sequence shown in SEQ ID NO: 2. The second extracellular loop of CLDN6 preferably comprises amino acids 138 to 160, preferably amino acids 141 to 159, more preferably amino acids 145 to 157 of the amino acid sequence shown in SEQ ID NO: 1 or the amino acid sequence shown in SEQ ID NO: 2. Said first and second extracellular loops preferably form the extracellular portion of CLDN6.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

According to the invention, the term "claudin positive cancer" or similar terms means a cancer involving cancer cells expressing a claudin, preferably on the surface of said cancer cells. CLDN6 is expressed on the surface of cells if it is located at the surface of said cells and is accessible to binding by CLDN6-specific antibodies added to the cells.

"Cell surface" is used in accordance with its normal meaning in the art, and thus includes the outside of the cell which is accessible to binding by proteins and other molecules. For example, a transmembrane protein having one or more extracellular portions is considered as being expressed on the cell surface.

The term "extracellular portion" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

The terms "part" or "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope or peptide is preferably immunologically equivalent to the epitope or peptide it is derived from. A part or fragment of a protein sequence preferably comprises a sequence of at least 6, in particular at least 8, at least 10, at least 12, at least 15, at least 20, at least 30, at least 50, or at least 100 consecutive amino acids of the protein sequence.

According to the invention, CLDN6 is not substantially expressed in a cell if the level of expression is lower compared to expression in placenta cells or placenta tissue. Preferably, the level of expression is less than 10%, preferably less than 5%, 3%, 2%, 1%, 0.5%, 0.1% or 0.05% of the expression in placenta cells or placenta tissue or even lower. Preferably, CLDN6 is not substantially expressed in a cell if the level of expression exceeds the level of expression in non-cancerous tissue other than placenta by no more than 2-fold, preferably 1.5-fold, and preferably does not exceed the level of expression in said non-cancerous tissue. Preferably, CLDN6 is not substantially expressed in a cell if the level of expression is below the detection limit and/or if the level of expression is too low to allow binding by CLDN6-specific antibodies added to the cells.

According to the invention, CLDN6 is expressed in a cell if the level of expression exceeds the level of expression in non-cancerous tissue other than placenta preferably by more than 2-fold, preferably 10-fold, 100-fold, 1000-fold, or 10000-fold. Preferably, CLDN6 is expressed in a cell if the level of expression is above the detection limit and/or if the level of expression is high enough to allow binding by CLDN6-specific antibodies added to the cells. Preferably, CLDN6 expressed in a cell is expressed or exposed on the surface of said cell.

It has been found that CLDN6 expression is only detectable in placenta as mRNA while no protein is detectable at all. Thus, the statements made herein with respect to CLDN6 expression in placenta preferably relate to expression of mRNA.

According to the invention, the term "disease" refers to any pathological state, including cancer, in particular those forms of cancer described herein. Any reference herein to cancer or particular forms of cancer also includes cancer metastasis thereof. In a preferred embodiment, a disease to be treated according to the present application involves cells expressing CLDN6, in particular cancer stem cells expressing CLDN6.

"Diseases associated with cells expressing CLDN6" or similar expressions means according to the invention that CLDN6 is expressed in cells of a diseased tissue or organ. In one embodiment, expression of CLDN6 in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a corresponding healthy tissue is repressed. According to the invention, diseases associated with cells expressing CLDN6 include cancer diseases. Furthermore, according to the invention, cancer diseases preferably are those wherein the cancer cells express CLDN6.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. Preferably, a "cancer disease" is characterized by cells expressing CLDN6, in particular cancer stem cells expressing CLDN6.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

A refractory cancer is a malignancy for which a particular treatment is ineffective, which is either initially unresponsive to treatment, or which becomes unresponsive over time. The terms "refractory", "unresponsive" or "resistant" are used interchangeably herein.

As used herein, the term "cancer stem cell" refers to a cell that can be a progenitor of a highly proliferative cancer cell. A cancer stem cell has the ability to re-grow a tumor as demonstrated by its ability to form tumors in immunocompromised mice. Cancer stem cells are also typically slow-growing relative to the bulk of a tumor, i.e. cancer stem cells are generally quiescent. In certain embodiments, but not all, the cancer stem cell may represent only a portion such as approximately 0.1 to 10% of a tumor. A cancer stem cells may have one or more or all of the following characteristics or properties: (i) can harbor the ability to initiate a tumor and/or to perpetuate tumor growth, (ii) can be generally relatively less mutated than the bulk of a tumor (e.g. due to slower growth and thus fewer DNA replication-dependent errors, improved DNA repair, and/or epigenetic/non-mutagenic changes contributing to their malignancy), (iii) can have many features of (a) normal stem cell(s) (e.g., similar cell surface antigen and/or intracellular expression profile, self-renewal programs, multi-drug resistance, an immature phenotype, etc., characteristic of normal stem cells) and may be derived from (a) normal stem cell(s), (iv) can be the source of metastases, (v) can be slow-growing or quiescent, (vi) can be tumorigenic (e.g. as determined by NOD/SCID implantation experiments), (vii) can be relatively resistant to traditional therapies (i.e. chemoresistant), and (viii) can comprise a subpopulation of a tumor (e.g. relative to the tumor bulk).

By "treat" is meant to administer a treatment such as a compound or composition or a combination of compounds or compositions to a subject in order to prevent or eliminate a disease, including reducing the size of a tumor or the number of tumors in a subject, arrest or slow a disease in a subject, inhibit or slow the development of a new disease in a subject, decrease the frequency or severity of symptoms and/or recurrences in a subject who currently has or who previously has had a disease and/or prolong, i.e. increase or expand the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

In the context of the present invention, terms such as "protect" or "prevent" relate to the prevention or treatment or both of the occurrence and/or the propagation of a disease in a subject and, in particular, to minimizing the chance that a subject will develop a disease or to delaying the development of a disease. For example, a subject at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The term "patient" means according to the invention a subject for treatment, in particular a diseased subject, including human beings, nonhuman primates or other animals, in particular mammals such as cows, horses, pigs, sheeps, goats, dogs, cats or rodents such as mice and rats. In a particularly preferred embodiment, a patient is a human being.

As used herein, the term "combination" in the context of the administration of a therapy refers to the use of more than one therapy or therapeutic agent. The use of the term "in combination" does not restrict the order in which the therapies or therapeutic agents are administered to a subject. A therapy or therapeutic agent can be administered prior to, concomitantly with, or subsequent to the administration of a second therapy or therapeutic agent to a subject. Preferably, the therapies or therapeutic agents are administered to a subject in a sequence, amount and/or within a time interval such that the therapies or therapeutic agents can act together. In a particular embodiment, the therapies or therapeutic agents are administered to a subject in a sequence, amount and/or within a time interval such that they provide an increased benefit than if they were administered otherwise, in particular, independently from each other. Preferably, the increased benefit is a synergistic effect.

"Target cell" shall mean any undesirable cell such as a cancer cell, in particular a cancer stem cell. In preferred embodiments, the target cell expresses CLDN6.

According to the invention, the term "chemotherapy" relates to treatment with one or more chemotherapeutic agents or combinations of chemotherapeutic agents such as cytostatic agents or cytotoxic agents. Chemotherapeutic agents according to the invention include cytostatic compounds and cytotoxic compounds.

According to the invention, the term "chemotherapeutic agent" includes taxanes such as paclitaxel and docetaxel and platinum compounds such as cisplatin and carboplatin, and combinations thereof. Preferred combinations, in particular for the treatment of ovarian cancer, may comprise a combination of a taxane and a platinum compound such as a combination of paclitaxel and carboplatin. Further preferred combinations, in particular for the treatment of ovarian cancer, in particular ovarian germ cell tumors, and/or for the treatment of germ cell tumors, in particular ovarian and testicular germ cell tumors, may comprise a combination of a platinum compound such as cisplatin with etoposide and/or bleomycin. According to the invention a reference to a chemotherapeutic agent is to include any prodrug such as ester, salt or derivative such as conjugate of said agent. Examples are conjugates of said agent with a carrier substance, e.g. protein-bound paclitaxel such as albumin-bound paclitaxel. Preferably, salts of said agent are pharmaceutically acceptable.

Taxanes are a class of diterpene compounds that were first derived from natural sources such as plants of the genus *Taxus*, but some have been synthesized artificially. The principal mechanism of action of the taxane class of drugs is the disruption of microtubule function, thereby inhibiting the process of cell division. Taxanes include docetaxel (Taxotere) and paclitaxel (Taxol).

According to the invention, the term "docetaxel" refers to a compound having the following formula:

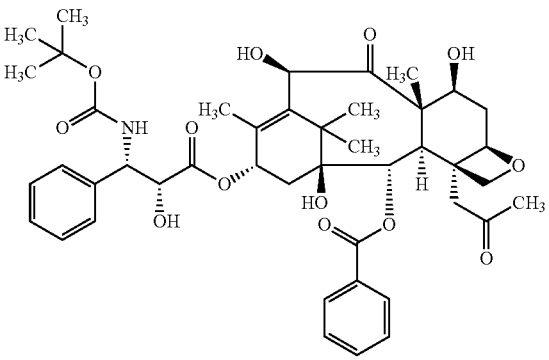 [SMILES: CC(=O)C[C@@]12CO[C@@H]1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@@](O)([C@@H](OC(=O)c4ccccc4)[C@H]21)C3(C)C]

In particular, the term "docetaxel" refers to the compound 1,7β,10β-trihydroxy-9-oxo-5β,20-epoxytax-11-ene-2α,4, 13α-triyl 4-acetate 2-benzoate 13-{(2R,3S)-3-[(tert-butoxycarbonyl)-amino]-2-hydroxy-3-phenylpropanoate}.

According to the invention, the term "paclitaxel" refers to a compound having the following formula:

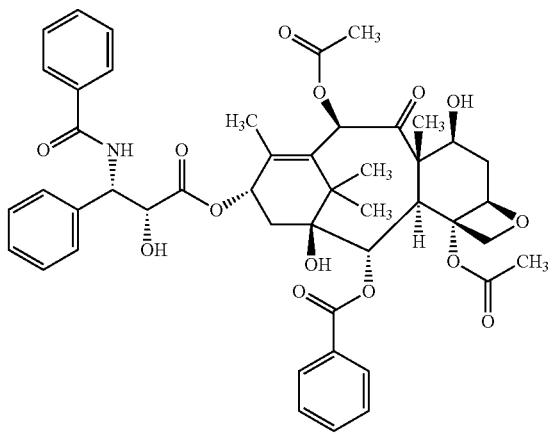 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

In particular, the term "paclitaxel" refers to the compound (2α,4α,5β,7β,10β,13α)-4,10-bis-(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate.

According to the invention, the term "platinum compound" refers to compounds containing platinum in their structure such as platinum complexes and includes compounds such as cisplatin, carboplatin and oxaliplatin.

The term "cisplatin" or "cisplatinum" refers to the compound cis-diamminedichloroplatinum(II) (CDDP) of the following formula:

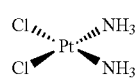

The term "carboplatin" refers to the compound cis-diammine(1,1-cyclobutanedicarboxylato)platinum(II) of the following formula:

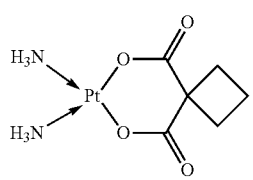

The term "oxaliplatin" refers to a compound which is a platinum compound that is complexed to a diaminocyclohexane carrier ligand of the following formula:

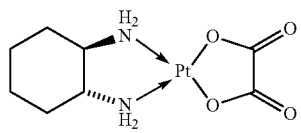

In particular, the term "oxaliplatin" refers to the compound [(1R,2R)-cyclohexane-1,2-diamine](ethanedioato-O,O')platinum(I). Oxaliplatin for injection is also marketed under the trade name Eloxatine.

Further chemotherapeutic agents which are envisioned for use in the present invention—either alone or in combination with other chemotherapeutic agents such as taxanes or platinum compounds—include but are not limited to nucleoside analogs, camptothecin analogs and anthracyclines.

The term "nucleoside analog" refers to a structural analog of a nucleoside, a category that includes both purine analogs and pyrimidine analogs.

The term "gemcitabine" is a compound which is a nucleoside analog of the following formula:

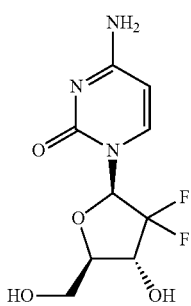 [SMILES: Nc1ccn([C@@H]2O[C@H](CO)[C@@H](O)C2(F)F)c(=O)n1]

In particular, the term refers to the compound 4-amino-1-(2-deoxy-2,2-difluoro-β-D-erythro-pentofuranosyl)pyrimidin-2(1H)-one or 4-amino-1-[(2R,4R,5R)-3,3-difluoro-4-hydroxy-5-(hydroxymethyl)oxolan-2-yl]-1,2-dihydropyrimidin-2-one.

The term "nucleoside analog" includes fluoropyrimidine derivatives such as fluorouracil and prodrugs thereof. The term "fluorouracil" or "5-fluorouracil" (5-FU or f5U) (sold under the brand names Adrucil, Carac, Efudix, Efudex and Fluoroplex) is a compound which is a pyrimidine analog of the following formula:

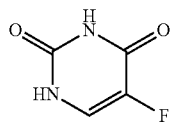

In particular, the term refers to the compound 5-fluoro-1H-pyrimidine-2,4-dione.

The term "capecitabine" (Xeloda, Roche) refers to a chemotherapeutic agent that is a prodrug that is converted into 5-FU in the tissues. Capecitabine which may be orally administered has the following formula:

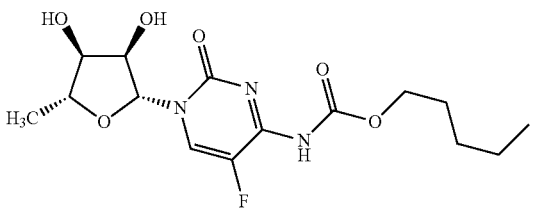 [SMILES: CCCCCOC(=O)Nc1nc(=O)n([C@@H]2O[C@H](C)[C@@H](O)[C@H]2O)cc1F]

In particular, the term refers to the compound pentyl [1-(3,4-dihydroxy-5-methyltetrahydrofuran-2-yl)-5 fluoro-2-oxo-1H-pyrimidin-4-yl]carbamate.

The term "folinic acid" or "leucovorin" refers to a compound useful in synergistic combination with the chemotherapy agent 5-fluorouracil. Thus, if reference is made herein to the administration of 5-fluorouracil or a prodrug thereof, said administration in one embodiment may comprise an administration in conjunction with folinic acid. Folinic acid has the following formula:

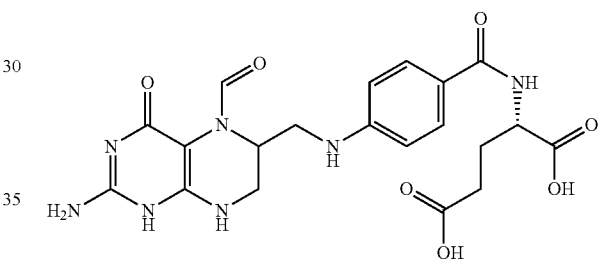

In particular, the term refers to the compound (2S)-2-{[4-[(2-amino-5-formyl-4-oxo-5,6,7,8-tetrahydro-1H-pteridin-6-yl)methylamino]benzoyl]amino}pentanedioic acid.

According to the invention, the term "camptothecin analog" refers to derivatives of the compound camptothecin (CPT; (S)-4-ethyl-4-hydroxy-1H-pyrano[3',4':6,7]indolizino[1,2-b]quinoline-3,14-(4H,12H)-dione). Preferably, the term "camptothecin analog" refers to compounds comprising the following structure:

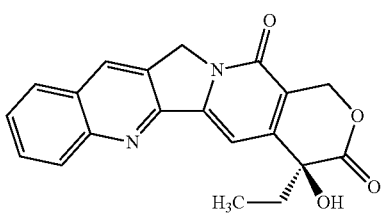 [SMILES: CC[C@@]1(O)C(=O)OCc2c1cc1n(c2=O)Cc2cc3ccccc3nc2-1]

According to the invention, preferred camptothecin analogs are inhibitors of DNA enzyme topoisomerase I (topo I). Preferred camptothecin analogs according to the invention are irinotecan and topotecan.

Irinotecan is a drug preventing DNA from unwinding by inhibition of topoisomerase I. In chemical terms, it is a semisynthetic analogue of the natural alkaloid camptothecin having the following formula:

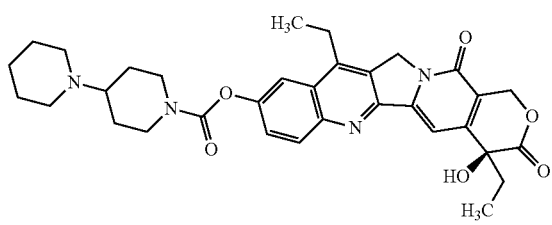 [SMILES: CCc1c2c(nc3ccc(OC(=O)N4CCC(N5CCCCC5)CC4)cc13)-c1cc3c(c(=O)n1C2)COC(=O)[C@]3(O)CC]

In particular, the term "irinotecan" refers to the compound (S)-4,11-diethyl-3,4,12,14-tetrahydro-4-hydroxy-3,14-dioxol H-pyrano[3',4':6,7]-indolizino[1,2-b]quinolin-9-yl-[1,4'-bipiperidine]-1'-carboxylate.

Topotecan is a topoisomerase inhibitor of the formula:

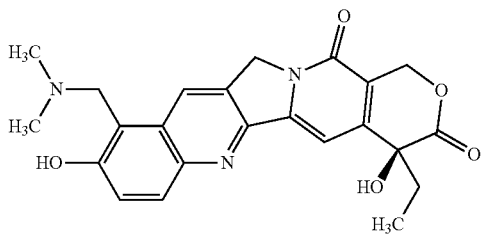 [SMILES: CC[C@@]1(O)C(=O)OCc2c1cc1n(c2=O)Cc2cc3c(CN(C)C)c(O)ccc3nc2-1]

In particular, the term "topotecan" refers to the compound (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride.

Anthracyclines are a class of drugs commonly used in cancer chemotherapy that are also antibiotics. Structurally, all anthracyclines share a common four-ringed 7,8,9,10-tetrahydrotetracene-5,12-quinone structure and usually require glycosylation at specific sites.

Anthracyclines preferably bring about one or more of the following mechanisms of action: 1. Inhibiting DNA and RNA synthesis by intercalating between base pairs of the DNA/RNA strand, thus preventing the replication of rapidly-growing cancer cells. 2. Inhibiting topoisomerase II enzyme, preventing the relaxing of supercoiled DNA and thus blocking DNA transcription and replication. 3. Creating iron-mediated free oxygen radicals that damage the DNA and cell membranes.

According to the invention, the term "anthracycline" preferably relates to an agent, preferably an anticancer agent for inducing apoptosis, preferably by inhibiting the rebinding of DNA in topoisomerase II.

Examples of anthracyclines and anthracycline analogs include, but are not limited to, daunorubicin (daunomycin), doxorubicin (adriamycin), epirubicin, idarubicin, rhodomycin, pyrarubicin, valrubicin, N-trifluoro-acetyl doxorubicin-14-valerate, aclacinomycin, morpholinodoxorubicin (morpholino-DOX), cyanomorpholino-doxorubicin (cyanomorpholino-DOX), 2-pyrrolino-doxorubicin (2-PDOX), 5-iminodaunomycin, mitoxantrone and aclacinomycin A (aclarubicin). Mitoxantrone is a member of the anthracendione class of compounds, which are anthracycline analogs that lack the sugar moiety of the anthracyclines but retain the planar polycylic aromatic ring structure that permits intercalation into DNA.

Specifically contemplated as anthracycline in the context of the present invention is epirubicin. Epirubicin is an anthracycline drug which has the following formula:

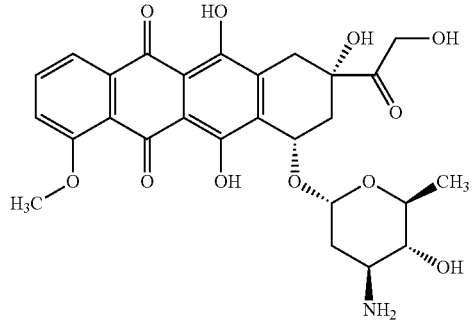 [SMILES: COc1cccc2c1C(=O)c1c(O)c3c(c(O)c1C2=O)C[C@@](O)(C(=O)CO)C[C@@H]3O[C@H]1C[C@H](N)[C@@H](O)[C@H](C)O1]

and is marketed under the trade name Ellence in the US and Pharmorubicin or Epirubicin Ebewe elsewhere. In particular, the term "epirubicin" refers to the compound (8R,10S)-10-[(2S,4S,5R,6S)-4-amino-5-hydroxy-6-methyl-oxan-2-yl]oxy-6,11-dihydroxy-8-(2-hydroxyacetyl)-1-methoxy-8-methyl-9,10-dihydro-7H-tetracen-5,12-dion. Epirubicin is favoured over doxorubicin, the most popular anthracycline, in some chemotherapy regimens as it appears to cause fewer side-effects.

The term "etoposide" refers to a semisynthetic derivative of podophyllotoxin that exhibits antitumor activity. Etoposide inhibits DNA synthesis by forming a complex with topoisomerase II and DNA. This complex induces breaks in double stranded DNA and prevents repair by topoisomerase II binding. Accumulated breaks in DNA prevent entry into the mitotic phase of cell division, and lead to cell death. Etoposide has the following formula:

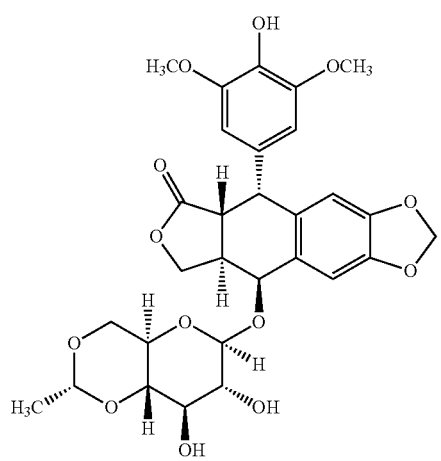 [SMILES: COc1cc([C@@H]2c3cc4c(cc3[C@@H](O[C@@H]3O[C@@H]5CO[C@@H](C)O[C@H]5[C@H](O)[C@H]3O)[C@H]3COC(=O)[C@H]23)OCO4)cc(OC)c1O]

In particular, the term refers to the compound 4'-demethyl-epipodophyllotoxin 9-[4,6-O(R)-ethylidene-beta-D-glucopyranoside], 4'-(dihydrogen phosphate).

The term "bleomycin" refers to a glycopeptide antibiotic produced by the bacterium *Streptomyces verticillus*. When used as an anticancer agent, it works by causing breaks in DNA. Bleomycin preferably comprises a compound having the following formula:

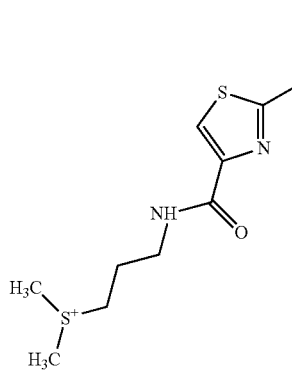
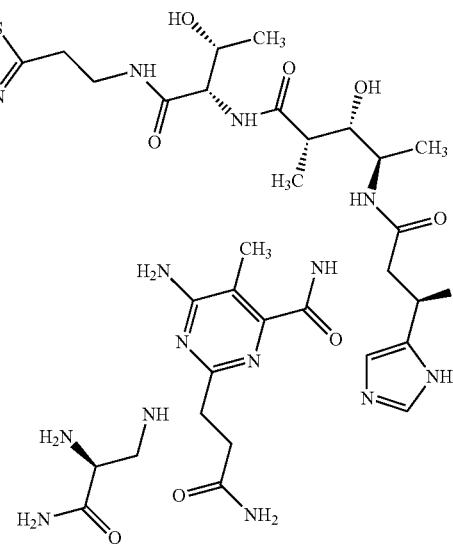

If according to the invention chemotherapy is administered in combination with an antibody having the ability of binding to CLDN6 (which may be present in a conjugate with at least one toxin drug moiety, i.e. as an antibody drug conjugate), it is preferred that the chemotherapy is administered prior to and/or simultaneously with administration of the antibody (as a mixture or as separate compositions). Preferably, administration of the chemotherapy is started prior to administration of the antibody. Preferably, the chemotherapy increases CLDN6 expression in cancer cells such as cancer stem cells and is started or administered prior to administration of the antibody such that the anti-tumoral activity of the antibody is enhanced. Preferably, administration of the chemotherapy starts at least 2, at least 4, at least 6, at least 8, at least 10, at least 12 or at least 14 days prior to the first administration of the antibody. Administration of chemotherapy may continue during administration of the antibody or may be stopped prior to or during administration of the antibody such as 1 to 3, 1 to 7, 1 to 10 or 1 to 14 days prior to administration of the antibody. Preferably, the chemotherapeutic agent comprises a taxane such as paclitaxel or docetaxel and/or a platinum compound such as cisplatin or carboplatin.

The term "antigen" relates to an agent such as a protein or peptide comprising an epitope against which an immune response is directed and/or is to be directed. In a preferred embodiment, an antigen is a tumor-associated antigen, such as CLDN6, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" or "tumor antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as CLDN6 preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" includes a glycoprotein comprising at least two heavy (H) chains and two light (L) chains inter-connected by disulfide bonds, and any molecule comprising an antigen-binding portion of such glycoprotein. The term "antibody" includes monoclonal antibodies, recombinant antibodies, human antibodies, humanized antibodies, chimeric antibodies, fragments or derivatives of antibodies, including, without limitation, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to CLDN6 is substantially free of antibodies that specifically bind antigens other than CLDN6). An isolated antibody that specifically binds to an epitope, isoform or variant of human CLDN6 may, however, have cross-reactivity to other related antigens, e.g., from other species (e.g., CLDN6 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition or mixture.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment.

Naturally occurring antibodies are generally monospecific, i.e. they bind to a single antigen. The present invention comprises antibodies binding to a target cell (by engaging CLDN6) and a second entity such as a cytotoxic cell (e.g. by engaging the CD3 receptor). The antibodies of the present invention may be bispecific or multispecific such as trispecific, tetraspecific and so on.

The term "bispecific molecule" is intended to include an agent which has two different binding specificities. For example, the molecule may bind to, or interact with (a) a cell surface antigen, and (b) a receptor such as an Fc receptor on the surface of an effector cell. The term "multispecific molecule" is intended to include an agent which has more than two different binding specificities. For example, the molecule may bind to, or interact with (a) a cell surface antigen, (b) a receptor such as an Fc receptor on the surface of an effector cell, and (c) at least one other component. Accordingly, the term "antibody having the ability of binding to CLDN6" includes, but is not limited to, bispecific, trispecific, tetraspecific, and other multispecific molecules which are directed to CLDN6, and to other targets, such as Fe receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci, USA 90: 6444-6448; Poljak, R. J., et al. (1994) Structure 2: 1121-1123).

In the context of the present invention, an "antibody having the ability of binding to CLDN6" preferably is capable of eliciting immune effector functions as described herein. Preferably, said immune effector functions are directed against cells such as cancer stem cells carrying the tumor-associated antigen CLDN6 on their surface.

The term "immune effector functions" in the context of the present invention includes any functions mediated by components of the immune system that result e.g. in the inhibition of tumor growth and/or inhibition of tumor development, including inhibition of tumor dissemination and metastasis. Preferably, immune effector functions result in killing of cancer cells, in particular cancer stem cells. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor-associated antigen, cytolysis of the cells carrying the tumor-associated antigen, and/or inhibition of proliferation of the cells carrying the tumor-associated antigen. Binding agents may also exert an effect simply by binding to tumor-associated antigens on the surface of a cancer cell. For example, antibodies may block the function of the tumor-associated antigen or induce apoptosis just by binding to the tumor-associated antigen on the surface of a cancer cell.

According to the invention, an antibody may be conjugated to a therapeutic moiety or agent such as a toxin drug moiety, in particular a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, amanitin, 1-dehydrotestosterone, glucocorticoids, procaine, tetracaine, lidocaine, propranolol, and puromycin and analogs or homologs thereof. Suitable therapeutic agents for forming antibody conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A. Particularly preferred toxin drug moieties according to the invention are compounds inhibiting microtubule assembly and having antiproliferative and/or cytotoxic effects.

Particularly preferred according to the invention is an antibody which is conjugated to a therapeutic moiety or agent, such as a cytotoxin, acting on slow-growing or quiescent cells such as cancer stem cells. Such therapeutic moieties include therapeutic moieties acting on mRNA and/or protein synthesis. Several inhibitors of transcription are known. For instance, actinomycin D, which is both a transcriptional inhibitor and a DNA damage agent, intercalates within the DNA and thus inhibits the initiation stage of transcription. Flavopiridol targets the elongation stage of transcription. α-Amanitin binds directly to RNA polymerase II, which leads to the inhibition of both initiation and elongation stages.

Antibodies also can be conjugated to a radioisotope, e.g., iodine-131, yttrium-90 or indium-111, to generate cytotoxic radiopharmaceuticals.

The antibody conjugates of the invention can be used to modify a given biological response, and the drug moiety is not to be construed as limited to classical chemical therapeutic agents. For example, the drug moiety may be a peptide. protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("II-6"), granulocyte macrophage colony stimulating factor ("GM-CSF"), granulocyte colony stimulating factor ("G-CSF"), or other growth factors. Further preferred drug moieties according to the invention are Curcumin, Salinomycin and Sulforaphane.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al, (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

In one preferred embodiment, an antibody according to the invention is conjugated to one or more maytansinoid molecules.

Maytansinoids are potent microtubule-targeted compounds that inhibit proliferation of cells at mitosis. Maytansinoids are derivatives of maytansine which is a 19-membered ansa macrolide structure attached to a chlorinated benzene ring. Maytansine has the following formula:

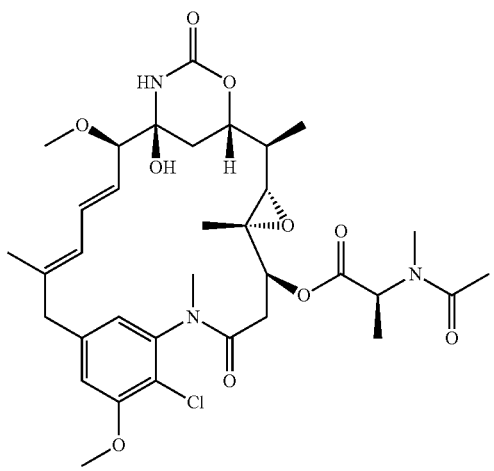

It was discovered that certain microbes also produce maytansinoids, such as maytansinol and C-3 maytansinol esters (U.S. Pat. No. 4,151,042). Synthetic maytansinol and maytansinol analogues have been reported, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,362,663; and 4,371,533, and Kawai et al (1984) Chem. Pharm. Bull. 3441-3451, herein incorporated by reference.

Maytansinoids are well known in the art and can be synthesized by known techniques or isolated from natural sources. Particularly preferred maytansinoids according to the invention are the thiol-containing derivatives of maytansine, such as DM1 and DM4. Such thiol-containing derivatives of maytansine include compounds wherein the methyl group bound to the carbonyl group is replaced by a group containing a free sulfhydryl group such as the group —R—SH where R represents an alkylene group or other carbon-containing group of atoms.

DM1, also known as mertansine, is a maytansinoid having the following formula:

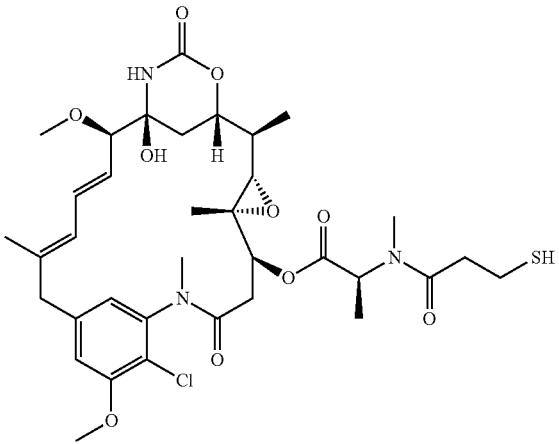

In particular, the term "mertansine" or "DM1" refers to the compound $N^{2'}$-deacetyl-$N^{2'}$-(3-mercapto-1-oxopropyl)-maytansine.

"DM4" refers to the compound $N^{2'}$-deacetyl-$N^{2'}$-(4-methyl-4-mercapto-1-oxopentyl)-maytansine.

Anti-CLDN6 antibody-maytansinoid conjugates are prepared by chemically linking an anti-CLDN6 antibody to a maytansinoid molecule without significantly diminishing the biological activity of either the antibody or the maytansinoid molecule. An average of 3-4 maytansinoid molecules may be conjugated per antibody molecule, although even one molecule of toxin/antibody is expected to enhance cytotoxicity over the use of naked antibody.

In this respect, the term "antibody covalently attached to at least one toxin drug moiety" includes situations where one or more molecules of the same drug are covalently attached to an antibody molecule as well as where different drugs are covalently attached to an antibody molecule. In the latter situation, one or more molecules of each of the different drugs may be attached to an antibody molecule, or a combination thereof (e.g. one molecule of one drug is attached while several molecules of another drug are attached).

In some embodiments of the invention, an antibody is conjugated to dolastatins or dolostatin peptidic analogs and derivatives, the auristatins (U.S. Pat. Nos. 5,635,483; 5,780, 588, herein incorporated by reference). Auristatins are synthetic analogs of dolostatin 10, a natural product derived from a marine mollusk, *Dolabela auricularia*. Like the maytansinoids, auristatins are microtubule disruptors. The dolastatin or auristatin drug moiety may be attached to the antibody through the N (amino) terminus or the C (carboxyl) terminus of the peptidic drug moiety.

Exemplary auristatin embodiments include monomethyl-auristatin drug moieties such as MMAE and MMAF which preferably are N-terminus linked.

MMAE, also known as Monomethyl auristatin E, has the following formula:

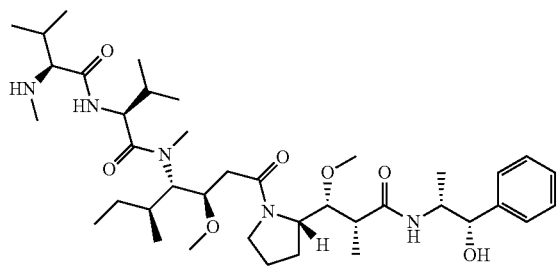 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In particular, the term "MMAE" refers to the compound (S)—N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3 methyl-2-(methylamino) butanamido)butanamide. MMAE is actually desmethyl-auristatin E, i.e., the N-terminal amino group has only one methyl substituent instead of two as in auristatin E itself. Particularly preferred according to the invention are antibody-vcAuristatin conjugates such as antibody-vcMMAE conjugates. According to the invention, the term "antibody-vcAuristatin" or "vcMMAE" refers to an antibody-drug conjugate (ADC) comprising an auristatin such as MMAE, linked via the lysosomally cleavable dipeptide, valine-citrulline (vc), to the antibody.

MMAF, also known as Monomethyl auristatin F, refers to the compound (S)-2-((2R,3R)-3-((S)-1-((3R,4S,5 S)-4-((S)—N,3 dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid.

There are many linking groups known in the art for making antibody-drug conjugates.

In one embodiment of the invention, an antibody is linked with a drug via a bifunctional crosslinking reagent. As used herein, a "bifunctional crosslinking reagent" refers to a reagent that possesses two reactive groups one of which is capable of reacting with an antibody, while the other one is capable of reacting with the drug to link the antibody with the drug, thereby forming a conjugate. Any suitable bifunctional crosslinking reagent can be used in connection with the invention, so long as the linker reagent provides for retention of the drug, e.g., cytotoxicity, and targeting characteristics of the antibody. Preferably, the linker molecule joins the drug to the antibody through chemical bonds, such that the drug and the antibody are chemically coupled (e.g., covalently bonded) to each other.

In one embodiment, the bifunctional crosslinking reagent comprises non-cleavable linkers. A non-cleavable linker is any chemical moiety that is capable of linking a drug, such as a maytansinoid, to an antibody in a stable, covalent manner. Preferably, a non-cleavable linker is not cleavable under physiological conditions, in particular inside a cell. Thus, non-cleavable linkers are substantially resistant to acid-induced cleavage, light-induced cleavage, peptidase-induced cleavage, esterase-induced cleavage, and disulfide bond cleavage, at conditions under which the drug or the antibody remains active. Suitable crosslinking reagents that form non-cleavable linkers between a drug and an antibody are well known in the art. In one embodiment, the drug is linked to the antibody through a thioether bond. Examples of non-cleavable linkers include linkers having a maleimido- or haloacetyl-based moiety for reaction with the drug such as with the sulfhydryl group of a maytansinoid. Such bifunctional crosslinking agents are well known in the art and include, but not limited to, N-succinimidyl 4-(maleimidomethyl)cyclohexanecarboxylate (SMCC) and N-succinimidyl-4-(N-maleimidomethyl)-cyclohexane-1-carboxy-(6-amidocaproate), which is a "long chain" analog of SMCC (LC-SMCC). Preferably, the bifunctional crosslinking reagent is SMCC. Using such linker, a drug such as mertansine can be linked via 4-(3-mercapto-2,5-dioxo-1-pyrrolidinylmethyl)-cylohexanecarboxylic acid to amino groups such as free NH2 groups of lysine residues of an antibody. Each antibody drug conjugate molecule may comprise a single antibody molecule bound to several molecules of mertansine.

In one particularly preferred embodiment, the linking reagent is a cleavable linker. Preferably, a cleavable linker is cleavable under physiological conditions, in particular inside a cell. Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photolabile linkers are useful at the body surface and in many body cavities that are accessible to light. Furthermore, infrared light can penetrate tissue. Peptidase labile linkers can be used to cleave certain peptides inside or outside cells. In one embodiment, the cleavable linker is cleaved under mild conditions, i.e., conditions within a cell under which the activity of the cytotoxic agent is not affected.

In one particularly preferred embodiment, the linker is a linker comprising or consisting of the dipeptide valine (Val)-citrulline (Cit) (vc), which is cleaved by cathepsin inside tumour cells.

According to the invention, the term "cancer therapy directed against cancer stem cells" relates to any therapy that can be used to target and preferably kill and/or impair proliferation or viability of cancer stem cells. Such therapy includes i) antibodies, antibody fragments, and proteins that are either naked or conjugated to a therapeutic moiety that target certain cell surface targets on cancer stem cells, for example, CLDN6, (e.g. antibodies or antibody conjugates having the ability of binding to CLDN6 as described above) or ii) small molecules which impair proliferation or viability of a cancer stem cell. In a specific embodiment, the agent binds to an antigen that is expressed at a greater level on cancer stem cells than on normal stem cells. In a specific embodiment, the agent binds specifically to a cancer stem cell antigen.

The term "binding" according to the invention preferably relates to a specific binding.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody is not (substantially) capable of binding to a target if it has no significant affinity for said target and does not bind significantly, in particular does not bind detectably, to said target in standard assays. Preferably, the antibody does not detectably bind to said target if present in a concentration of up to 2, preferably 10, more preferably 20, in particular 50 or 100 µg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for CLDN6 if it is capable of binding to CLDN6 but is not (substantially) capable of binding to other targets. Preferably, an antibody is specific for CLDN6 if the affinity for and the binding to such other targets does not significantly exceed the affinity for or binding to CLDN6-unrelated proteins such as bovine serum albumin (BSA), casein, human serum albumin (HSA) or non-claudin transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

Preferably, binding of an antibody having the ability of binding to CLDN6 to cells expressing CLDN6 induces or mediates killing of cells expressing CLDN6. The cells expressing CLDN6 are preferably cancer stem cells and are, in particular, cells of the cancer diseases described herein such as cancer stem cells of ovarian cancer. Preferably, the antibody induces or mediates killing of cells by inducing one or more of complement dependent cytotoxicity (CDC) mediated lysis, antibody dependent cellular cytotoxicity (ADCC) mediated lysis, apoptosis, and inhibition of proliferation of cells expressing CLDN6. Preferably, ADCC mediated lysis of cells takes place in the presence of effector cells, which in particular embodiments are selected from the group consisting of monocytes, mononuclear cells, NK cells and PMNs. Inhibiting proliferation of cells can be measured in vitro by determining proliferation of cells in an assay using bromodeoxyuridine (5-bromo-2-deoxyuridine, BrdU). BrdU is a synthetic nucleoside which is an analogue of thymidine and can be incorporated into the newly synthesized DNA of replicating cells (during the S phase of the cell cycle), substituting for thymidine during DNA replication. Detecting the incorporated chemical using, for example, antibodies specific for BrdU indicates cells that were actively replicating their DNA.

In preferred embodiments, antibodies described herein can be characterized by one or more of the following properties:
a) specificity for CLDN6;
b) a binding affinity to CLDN6 of about 100 nM or less, preferably, about 5-10 nM or less and, more preferably, about 1-10 nM or less,
c) the ability to induce or mediate CDC on CLDN6 positive cells;
d) the ability to induce or mediate ADCC on CLDN6 positive cells;
e) the ability to inhibit the growth of CLDN6 positive cells;
f) the ability to induce apoptosis of CLDN6 positive cells.

In one embodiment, an antibody having the ability of binding to CLDN6 has the ability of binding to an epitope present in CLDN6, preferably an epitope located within the extracellular domains of CLDN6, in particular the first extracellular loop, preferably amino acid positions 28 to 76 of CLDN6 or the second extracellular loop, preferably amino acid positions 141 to 159 of CLDN6. In particular embodiments, an antibody having the ability of binding to CLDN6 binds to an epitope on CLDN6 which is not present on CLDN9. Preferably, an antibody having the ability of binding to CLDN6 binds to an epitope on CLDN6 which is not present on CLDN4 and/or CLDN3. Most preferably, an antibody having the ability of binding to CLDN6 binds to an epitope on CLDN6 which is not present on a CLDN protein other than CLDN6.

An antibody having the ability of binding to CLDN6 preferably binds to CLDN6 but not to CLDN9 and preferably does not bind to CLDN4 and/or CLDN3. Preferably, an antibody having the ability of binding to CLDN6 is specific for CLDN6. Preferably, an antibody having the ability of binding to CLDN6 binds to CLDN6 expressed on the cell surface. In particular preferred embodiments, an antibody having the ability of binding to CLDN6 binds to native epitopes of CLDN6 present on the surface of living cells.

In a preferred embodiment, an antibody having the ability of binding to CLDN6 comprises a heavy chain variable region (VH) comprising an amino acid sequence selected from the group consisting of SEQ ID NOs: 3, 5, 7, 9, and a fragment thereof.

In a preferred embodiment, an antibody having the ability of binding to CLDN6 comprises a light chain variable region (VL) comprising an amino acid sequence selected from the group consisting of SEQ ID NOs: 4, 6, 8, 10, 11, 12, and a fragment thereof.

In certain preferred embodiments, an antibody having the ability of binding to CLDN6 comprises a combination of heavy chain variable region (VH) and light chain variable region (VL) selected from the following possibilities (i) to (vii):
(i) the VH comprises an amino acid sequence represented by SEQ ID NO: 3 or a fragment thereof and the VL comprises an amino acid sequence represented by SEQ ID NO: 4 or a fragment thereof,
(ii) the VH comprises an amino acid sequence represented by SEQ ID NO: 5 or a fragment thereof and the VL comprises an amino acid sequence represented by SEQ ID NO: 6 or a fragment thereof,
(iii) the VH comprises an amino acid sequence represented by SEQ ID NO: 7 or a fragment thereof and the VL comprises an amino acid sequence represented by SEQ ID NO: 8 or a fragment thereof,
(iv) the VH comprises an amino acid sequence represented by SEQ ID NO: 9 or a fragment thereof and the VL comprises an amino acid sequence represented by SEQ ID NO: 10 or a fragment thereof,
(v) the VH comprises an amino acid sequence represented by SEQ ID NO: 5 or a fragment thereof and the VL comprises an amino acid sequence represented by SEQ ID NO: 4 or a fragment thereof,
(vi) the VH comprises an amino acid sequence represented by SEQ ID NO: 5 or a fragment thereof and the VL comprises an amino acid sequence represented by SEQ ID NO: 11 or a fragment thereof,
(vii) the VH comprises an amino acid sequence represented by SEQ ID NO: 5 or a fragment thereof and the VL comprises an amino acid sequence represented by SEQ ID NO: 12 or a fragment thereof.

In a particularly preferred embodiment, an antibody having the ability of binding to CLDN6 comprises the following combination of heavy chain variable region (VH) and light chain variable region (VL):
the VH comprises an amino acid sequence represented by SEQ ID NO: 5 or a fragment thereof and the VL comprises an amino acid sequence represented by SEQ ID NO: 4 or a fragment thereof.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment an antibody comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of antibodies made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment an antibody comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

It is to be understood that the antibodies described herein may be delivered to a patient by administering a nucleic acid such as RNA encoding the antibody and/or by administering a host cell comprising a nucleic acid such as RNA encoding the antibody. Thus, a nucleic acid encoding an antibody when administered to a patient may be present in naked form or in a suitable delivery vehicle such as in the form of liposomes or viral particles, or within a host cell. The nucleic acid provided can produce the antibody over extended time periods in a sustained manner mitigating the instability at least partially observed for therapeutic antibodies. Nucleic acids to be delivered to a patient can be produced by recombinant means. If a nucleic acid is administered to a patient without being present within a host cell, it is preferably taken up by cells of the patient for expression of the antibody encoded by the nucleic acid. If a nucleic acid is administered to a patient while being present within a host cell, it is preferably expressed by the host cell within the patient so as to produce the antibody encoded by the nucleic acid.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the antibody described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

The genome of alphaviruses is single stranded RNA of positive sense (ssRNA(+)) that encodes two open reading frames (ORF) for large polyproteins. The ORF at the 5'-end of the genome encodes the non-structural proteins nSP1 to nSP4 (nsP1-4), which are translated and processed to an RNA-dependent RNA-polymerase (replicase); the ORF at the 3'-end encodes the structural proteins—capsid and glycoproteins. Both ORFs are separated by the so called sub-genomic promoter (SGP), which governs the transcription of the structural ORF. When exploited as gene vectors, the structural proteins behind the SGP are commonly replaced by transgenes. In order to package such vectors into viral particles, the structural proteins are commonly expressed in trans from helper constructs. Alphaviruses replicate in the cytoplasm of infected cells exclusively at the RNA level. After infection, the ssRNA(+) genome acts as mRNA for the translation of the nsP1234 poly-protein precursor which is at early stages of the viral life cycle autoproteolytically processed to the fragments nsP123 and nsP4. Fragments nsP123 and nsP4 form the (−)strand replicase complex that transcribes (−)stranded RNA from the genomic RNA template. At later stages, the nsP1234 polyprotein is completely cleaved to the single proteins which assemble to the (+)strand replicase complex that synthesizes new (+)stranded genomes, as well as subgenomic transcripts that code the structural proteins or transgenes. Subgenomic RNA as well as new genomic RNA is capped and poly-adenylated and thus recognized as mRNA after target cells infection. Only new genomic RNA contains a packaging signal which ensures exclusive packaging of genomic RNA into budding virions. The attractiveness of alphaviral replicons for vectorology is based on the positive orientation of the capped and poly-adenylated RNA genome. Translatable replicon RNA can easily be synthesized in vitro, whereby capping may be achieved with cap-analoga added to the in vitro transcription reaction and poly-A tails may be encoded as poly-T tracks on the plasmid templates. In vitro transcribed (IVT) replicons are transfected by conventional transfection techniques and even low amounts of starting IVT RNA are multiplied rapidly. Within a few hours after transfer, transgenes which are placed downstream of the SGP are transcribed to very high copy numbers of about 40.000 to 200.000 copies of subgenomic RNA per cell, thus it is not surprising that recombinant proteins are strongly expressed. Dependend on the specific aim, IVT replicons may be transfected directly into target cells, or packaged into alphaviral particles with helper vectors that provide structural genes in trans. Transfer into the skin or muscles leads to high and sustained local expression, paralleled by a strong induction of humoral and cellular immune response In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human 3-globin gene.

Preferably, RNA if delivered to, i.e. transfected into, a cell, in particular a cell present in vivo, expresses the protein or peptide it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in placenta means that said protein is primarily expressed in placenta and is not expressed in other tissues or is not expressed to a significant extent in other tissue or organ types. Thus, a protein that is exclusively expressed in cells of the placenta and to a significantly lesser extent in any other tissue is specifically expressed in cells of the placenta In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs.

According to the invention, the term "RNA encoding" means that RNA, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding an antibody described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding of an antibody to its target or to sustain effector functions of an antibody. Preferably, a sequence which is a variant with respect to a specific sequence, when it replaces the specific sequence in an antibody retains binding of said antibody to CLDN6 and preferably functions of said antibody as described herein, e.g. CDC mediated lysis or ADCC mediated lysis.

For example, the sequences shown in the sequence listing can be modified so as to remove one or more, preferably all free cysteine residues, in particular by replacing the cysteine residues by amino acids other than cysteine, preferably serine, alanine, threonine, glycine, tyrosine, leucine or methionine, most preferably alanine or serine.

It will be appreciated by those skilled in the art that in particular the sequences of the CDR, hypervariable and variable regions can be modified without losing the ability to bind CLDN6.

For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci, USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (Tor example *Saccharomyces cerevisiae*), *Schizosaccharomyces* (for example Schizo *saccharomyces pombe*), *Pichia* (for example *Pichia pastoris* and *Pichia methanolied*), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

The term "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN6 antibodies when immunized with CLDN6 antigen and/or cells expressing CLDN6. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN6 (e.g., IgG, IgA and/or IgE) by undergoing V-D-J recombination and isotype switching.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Although the following provides considerations regarding the mechanism underlying the therapeutic efficacy of antibodies it is not to be considered as limiting to the invention in any way.

The antibodies described herein preferably interact with components of the immune system, preferably through ADCC or CDC. Antibodies described herein can also be used to target payloads (e.g., radioisotopes, drugs or toxins) to directly kill tumor cells or can be used synergistically with traditional chemotherapeutic agents, attacking tumors through complementary mechanisms of action that may include anti-tumor immune responses that may have been compromised owing to a chemotherapeutic's cytotoxic side effects on T lymphocytes. However, antibodies described herein may also exert an effect simply by binding to CLDN6 on the cell surface, thus, e.g. blocking proliferation of the cells.

Antibody-Dependent Cell-Mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fe receptors have been identified, and specific cell populations characteristically express defined Fe receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Antibodies described herein can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice," The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodes for cancer therapy ISBN-0-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. E. coli. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

Murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci, U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies to bind an antigen can be determined using standard binding assays (e.g., ELISA, Western Blot, Immunofluorescence and flow cytometric analysis).

To purify antibodies, selected hybridomas can be grown in two-liter spinner-flasks for monoclonal antibody purification. Alternatively, antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at $-80°$ C.

To determine if the selected monoclonal antibodies bind to unique epitopes, site-directed or multi-site directed mutagenesis can be used.

To determine the isotype of antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

In order to demonstrate presence of antibodies in sera of immunized mice or binding of monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at $4°$ C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of antibodies in sera of immunized mice or binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal cal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against the antigen for 30 min. at $25°$ C. After washing, cells can be reacted with an Alexa555-labelled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendors instructions.

Antibodies can be tested for their ability to mediate phagocytosis and killing of cells expressing CLDN6. The testing of monoclonal antibody activity in vitro will provide an initial screening prior to testing in vivo models.

Antibody Dependent Cell-Mediated Cytotoxicity (ADCC)

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}$Cr labeled target cells expressing CLDN6, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidated by viable cells only. Purified anti-CLDN6 IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-CLDN6 monoclonal antibodies can also be tested in various combinations to determine whether cytolysis is enhanced with multiple monoclonal antibodies.

Complement Dependent Cytotoxicity (CDC)

Monoclonal anti-CLDN6 antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5\times10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3\times10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 g/ml). Then, supernatants are replaced by PBS containing 2.5 µg/ml ethidium bromide and fluorescence emission upon excitation at 520 nm is measured at 600 nm using a Tecan Safire. The percentage specific lysis is calculated as follows: % specific lysis=(fluorescence sample–fluorescence background)/(fluorescence maximal lysis–fluorescence background)×100.

Induction of Apoptosis and Inhibition of Cell Proliferation by Monoclonal Antibodies To test for the ability to initiate apoptosis, monoclonal anti-CLDN6 antibodies can, for example, be incubated with CLDN6 positive tumor cells or CLDN6 transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 gi/ml in PBS) in a FACS tube and assessed immediately by flow cytometry (as above). Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Binding agents described herein also can be tested in an in vivo model (e.g. in immune deficient mice carrying xenografted tumors inoculated with cell lines expressing CLDN6 to determine their efficacy in controlling growth of CLDN-expressing tumor cells.

In vivo studies after xenografting CLDN6 expressing tumor cells into immunocompromised mice or other animals can be performed using antibodies described herein. Antibodies can be administered to tumor free mice followed by injection of tumor cells to measure the effects of the antibodies to prevent formation of tumors or tumor-related symptoms. Antibodies can be administered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies animals can be inoculated with antibodies or control reagents and thoroughly investigated for symptoms possibly related to CLDN6-antibody therapy. Possible side effects of in vivo application of CLDN6 antibodies particularly include toxicity at CLDN6 expressing tissues including placenta. Antibodies recognizing CLDN6 in human and in other species, e.g. mice, are particularly useful to predict potential side effects mediated by application of monoclonal CLDN6-antibodies in humans.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

The pharmaceutical compositions of the invention are preferably sterile and contain effective amount of the antibodies described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer lactate.

The term "carrier" refers to an organic or inorganic component, of a natural or synthetic nature, in which the active component is combined in order to facilitate, enhance or enable application, According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. In particular, the term "effective amount" refers to the amount of a therapy that is sufficient to result in the prevention of the development, recurrence, or onset of cancer and one or more symptoms thereof, reduce the severity, the duration of cancer, ameliorate one or more symptoms of cancer, prevent the advancement of cancer, cause regression of cancer, and/or prevent cancer metastases. In an embodiment of the invention, the amount of a therapy is effective to achieve a stabilization, reduction or elimination of the cancer stem cell population and/or eradication, removal, or control of primary cancer, metastatic cancer and/or recurrent cancer.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients to treat or prevent a cancer disease, e.g., a cancer disease such as described herein characterized by the presence of cancer stem cells expressing CLDN6.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment may be effectively combined with various other drugs. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer into a chronic disease. The following list provides some non-limiting examples of anti-cancer drugs and therapies which can be used in combination with the present invention:

1. Chemotherapy

Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumour agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. A synergistic anti-cancer action of chemotherapeutic and vaccination-based immunotherapeutic drugs has been demonstrated in multiple studies (see e.g. Quoix et al. 2011: Therapeutic vaccination with TG4010 and first-line chemotherapy in advanced non-small-cell lung cancer: a controlled phase 2B trial. Lancet Oncol. 12(12): 1125-33; see also Liseth et al. 2010: Combination of intensive chemotherapy and anticancer vaccines in the treatment of human malignancies: the hematological experience. J Biomed Biotechnol. 2010: 6920979; see also Hirooka et al 2009: A combination therapy of gemcitabine with immunotherapy for patients with inoperable locally advanced pancreatic cancer. Pancreas 38(3): e69-74). There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), crizotinib (Xalkori), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), liposome-encapsulated doxorubicin (Doxil), methotrexate (Folex, Mexate, Amethopterin), paclitaxel (Taxol, Abraxane), sorafinib (Nexavar), sunitinib (Sutent), topotecan (Hycamtin), trabectidin (Yondelis), vincristine (Oncovin, Vincasar PFS), and vinblastine (Velban).

2. Surgery

Cancer surgery—an operation to remove the tumor—remains the foundation of cancer treatment. Surgery can be combined with other cancer treatments in order to delete any remaining tumor cells. Combining surgical methods with subsequent immunotherapeutic treatment is a promising approach which has been demonstrated countless times.

3. Radiation

Radiation therapy remains an important component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver the radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or seeds directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review see Baskar et al. 2012: Cancer and radiation therapy: current advances and future directions. Int. J Med Sci. 9(3): 193-199.

4. Antibodies

Antibodies (preferably monoclonal antibodies) achieve their therapeutic effect against cancer cells through various mechanisms. They can have direct effects in producing apoptosis or programmed cell death. They can block components of signal transduction pathways such as e.g. growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Combining surgical methods with immunotherapeutic drugs or methods is an successful approach, as e.g. demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present invention: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumornab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNTO888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolormab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-I), Gemtuzumab ozogamicin (CD33), Gevokizumab (IL-1β), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Narnatumab (RON), Necitumumab (EGFR), Nimotuzumab (EGFR), Nivolumab (IgG4), Ofatumumab (CD20), Olaratumnab (PDGF-R α), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzumab (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBSO7 (GD2), Tremelimumab (CTLA-4), Tucotuzumab celmoleukin (EpCAM), Ublituximab (MS4A1), Urelumab (4-1 BB), Volociximab (integrin α5β1), Votumumab (tumor antigen CTAA16.88), Zalutumumab (EGFR), Zanolimumab (CD4).

5. Cytokines, Chemokines, Costimulatory Molecules, Fusion Proteins

Combined usage of the antigen-coding pharmaceutical compositions of the present invention with cytokines, chemokines, costimulatory molecules and/or fusion proteins thereof to evoke beneficial immune modulation or tumor inhibition effects is another embodiment of the present invention. In order to increase the infiltration of immune cells into the tumor and facilitate the movement of antigen-presenting cells to tumor-draining lymph nodes, various chemokines with C, CC, CXC and CX3C structures might be used. Some of the most promising chemokines are e.g CCR7 and its ligands CCL19 and CCL21, furthermore CCL2, CCL3, CCL5, and CCL16. Other examples are CXCR4, CXCR7 and CXCL12. Furthermore, costimulatory or regulatory molecules such as e.g. B7 ligands (B7.1 and B7.2) are useful. Also useful are other cytokines such as e.g. interleukins especially (e.g. IL-1 to IL17), interferons (e.g. IFNalpha1 to IFNalpha8, IFNalpha10, IFNalpha13, IFNalpha14, IFNalpha16, IFNalpha17, IFNalpha21, IFNbeta1, IFNW, IFNE1 and IFNK), hematopoietic factors, TGFs (e.g. TGF-α, TGF-β, and other members of the TGF family), finally members of the tumor necrosis factor family of receptors and their ligands as well as other stimulatory molecules, comprising but not limited to 4-1BB, 4-1BB-L, CD137, CD137L, CTLA-4GITR, GITRL, Fas, Fas-L, TNFR1, TRAIL-R1, TRAIL-R2, p75NGF-R, DR6, LT.beta.R, RANK, EDAR1, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

6. Bacterial Treatments

Researchers have been using anaerobic bacteria, such as *Clostridium novyi*, to consume the interior of oxygen-poor tumours. These should then die when they come in contact with the tumour's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumour, the enzyme is expressed solely in the tumour. Thus, a systemically applied prodrug is metabolised to the toxic drug only in the tumour. This has been demonstrated to be effective with the nonpathogenic anaerobe *Clostridium sporogenes*.

7. Kinase Inhibitors

Another large group of potential targets for complementary cancer therapy comprises kinase inhibitors, because the growth and survival of cancer cells is closely interlocked with the deregulation of kinase activity. To restore normal kinase activity and therefor reduce tumor growth a broad range of inhibitors is in used. The group of targeted kinases comprises receptor tyrosine kinases e.g. BCR-ABL, B-Raf, EGFR, HER-2/ErbB2, IGF-IR, PDGFR-α, PDGFR-β, c-Kit, Flt-4, Flt3, FGFR1, FGFR3, FGFR4, CSF1R, c-Met, RON, c-Ret, ALK, cytoplasmic tyrosine kinases e.g. c-SRC, c-YES, Abl, JAK-2, serine/threonine kinases e.g. ATM, Aurora A & B, CDKs, mTOR, PKCi, PLKs, b-Raf, S6K, STKIi/LKB1 and lipid kinases e.g. PI3K, SK1. Small molecule kinase inhibitors are e.g. PHA-739358, Nilotinib, Dasatinib, and PD166326, NSC 743411, Lapatinib (GW-572016), Canertinib (CI-1033), Semaxinib (SU5416), Vatalanib (PTK787/ZK222584), Sutent (SU11248), Sorafenib (BAY 43-9006) and Lefunomide (SU101). For more information see e.g. Zhang et al. 2009: Targeting cancer with small molecule kinase inhibitors. Nature Reviews Cancer 9, 28-39.

8. Toll-Like Receptors

The members of the Toll-like receptor (TLRs) family are an important link between innate and adaptive immunity and the effect of many adjuvants rely on the activation of TLRs. A large number of established vaccines against cancer incorporate ligands for TLRs for boosting vaccine responses. Besides TLR2, TLR3, TLR4 especially TLR7 and TLR 8 have been examined for cancer therapy in passive immunotherapy approaches. The closely related TLR7 and TLR8 contribute to antitumor responses by affecting immune cells, tumor cells, and the tumor microenvironment and may be activated by nucleoside analogue structures. All TLR's have been used as stand-alone immunotherapeutics or cancer vaccine adjuvants and may be synergistically combined with the formulations and methods of the present invention. For more information see van Duin et al. 2005: Triggering TLR signaling in vaccination. Trends in Immunology, 27(1):49-55.

9. Angiogenesis Inhibitors

In addition to therapies which target immune modulatory receptors affected by tumor-mediated escape mechanisms and immune suppression there are therapies which target the tumor environment. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which may be combined with the present invention are soluble VEGF (VEGF isoforms VEGF121 and VEGF165, receptors VEGFR1, VEGFR2 and co-receptors Neuropilin-1 and Neuropilin-2) 1 and NRP-1, angiopoietin 2, TSP-1 and TSP-2, angiostatin and related molecules, endostatin, vasostatin, calreticulin, platelet factor-4, TIMP and CDAI, Meth-1 and Meth-2, IFN-α, -β and -γ, CXCL10, IL-4, -12 and -18, prothrombin (kringle domain-2), antithrombin III fragment, prolactin, VEGI, SPARC, osteopontin, maspin, canstatin, proliferin-related protein, restin and drugs like e.g. bevacizumab, itraconazole, carboxyamidotriazole, TNP-470, CM101, IFN-α, platelet factor-4, suramin, SU5416, thrombospondin, VEGFR antagonists, angiostatic steroids+heparin, cartilage-derived angiogenesis Inhibitory factor, matrix metalloproteinase inhibitors, 2-methoxyestradiol, tecogalan, tetrathiomolybdate, thalidomide, thrombospondin, prolactinα Vβ3 inhibitors, linomide, tasquinimod, For review see Schoenfeld and Dranoff 2011: Anti-angiogenesis immunotherapy. Hum Vaccin. (9):976-81.

10. Small Molecule Targeted Therapy Drugs

Small molecule targeted therapy drugs are generally inhibitors of enzymatic domains on mutated, overexpressed, or otherwise critical proteins within the cancer cell. Prominent and non-limiting examples are the tyrosine kinase inhibitors imatinib (Gleevec/Glivec) and gefitinib (Iressa). The use of small molecules e.g. sunitinib malate and/or sorafenib tosylate targeting some kinases in combination with vaccines for cancer therapy is also described in previous patent application US2009004213.

11. Virus-Based Vaccines

There are a number of virus-based cancer vaccines available or under development which can be used in a combined therapeutic approach together with the formulations of the present invention.

One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting anti-tumour specific responses. Recombinant viruses such as vaccinia viruses, herpes simplex viruses, adenoviruses, adeno-associated viruses, retroviruses and avipox viruses have been used in animal tumour models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g. the hepatitis B virus or other virus families including Parvoviridae (e.g. adeno-associated virus), Retroviridae (e.g. HIV), and Flaviviridae (e.g. Hepatitis C virus). For a general review see Sorensen and Thompsen 2007: Virus-based immunotherapy of cancer: what do we know and where are we going?APMIS 115(11): 1177-93; virus-like particles against cancer are reviewed in Buonaguro et al. 2011: Developments in virus-like particle-based vaccines for infectious diseases and cancer. Expert Rev Vaccines 10(11):1569-83; and in Guillén et al. 2010: Virus-like particles as vaccine antigens and adjuvants: application to chronic disease, cancer immunotherapy and infectious disease preventive strategies. Procedia in Vaccinology 2 (2), 128-133.

12. Multi-Epitope Strategies

The use of multi epitopes shows promising results for vaccination. Fast sequencing technologies combined with intelligent algorithms systems allow the exploitation of the tumor mutanome and may provide multi epitopes for individualized vaccines which can be combined with the present invention. For more information see 2007: Vaccination of metastatic colorectal cancer patients with matured dendritic cells loaded with multiple major histocompatibility complex class I peptides. J Immunother 30: 762-772; furthermore Castle et al. 2012: Exploiting the mutanome for tumor vaccination. Cancer Res 72 (5):1081-91.

13. Adoptive T Cell Transfer

For example, a combination of a tumor antigen vaccination and T cell transfer is described in: Rapoport et al. 2011: Combination immunotherapy using adoptive T-cell transfer and tumor antigen vaccination on the basis of hTERT and survivin after ASCT for myeloma. Blood 117(3):788-97.

14. Peptide-Based Target Therapies

Peptides can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

15. Other Therapies

There are numerous other cancer therapies which can be combined with the present invention in order to create synergistic effects. Non-limiting examples are treatments targeting apoptosis, hyperthermia, hormonal therapy, telomerase therapy, insulin potentiation therapy, gene therapy and photodynamic therapy.

Various methods known in the art can be used to detect and/or determine the amount of cells expressing CLDN6.

For example, an immunoassay may be used for detecting CLDN6 protein expression in cells or on the cell surface. According to the present invention, immunoassays include, but are not limited to, western blots, immunohistochemistry, radioimmunoassays, ELISA (enzyme linked immunosorbent assay), "sandwich" immunoassays, immunoprecipitation assays, precipitaton reactions, gel diffusion precipitaton reactions, immunodiffusion assays, agglutination assays, complement-fixation assays, immunoradiometric assays, fluorescent immunoassays, immunofluorescence, protein A immunoassays, flow cytometry, or FACS analysis.

In one embodiment, the cells are bound with one or more labeled antibodies having the ability of binding to CLDN6 prior to detection and/or determination of the amount.

Alternatively, expression of CLDN6 mRNA may be detected or the amount of CLDN6 mRNA may be determined to detect and/or determine the amount of cells expressing CLDN6.

In certain embodiments of the invention, a sample obtained from a patient for detecting and/or determining the amount of cells expressing CLDN6 is a biological fluid, which includes but is not limited to blood, bone marrow, serum, urine, or interstitial fluid. In other embodiments, the sample from the patient is a tissue sample (e.g., a biopsy from a subject with or suspected of having cancerous tissue). Most preferably, the sample is a biopsy of a tumor.

In accordance with the methods of the invention, a sample may be a biological sample which has been subjected to one or more pretreatment steps prior to the detection and/or determination of the amount of cells expressing CLDN6. In certain embodiments, a biological fluid is pretreated by centrifugation, filtration, precipitation, dialysis, or chromatography, or by a combination of such pretreatment steps. In other embodiments, a tissue sample is pretreated by freezing, chemical fixation, paraffin embedding, dehydration, permeablization, or homogenization followed by centrifugation, filtration, precipitation, dialysis, or chromatography, or by a combination of such pretreatment steps.

The amount of cancer stem cells in a sample can be expressed as the percentage of, e.g., overall cells or overall cancer cells in the sample, or quantitated relative to area (e.g. cells per field), volume (e.g. cells per ml) or weight (e.g. cells per ml).

The amount of cancer stem cells in a test sample can be compared with the amount of cancer stem cells in (a) reference sample(s). In one embodiment, the reference sample is a sample obtained from the subject undergoing therapy at an earlier time point (e.g., prior to receiving the therapy as a baseline reference sample, or at an earlier time point while receiving the therapy). In this embodiment, the therapy desirably results in a decrease in the amount of cancer stem cells in the test sample as compared with the reference sample. In another embodiment, the reference sample is obtained from a healthy subject who has no detectable cancer, or from a patient that is in remission for the same type of cancer. In this embodiment, the therapy desirably results in the test sample having an equal amount of cancer stem cells, or less than the amount of cancer stem cells than are detected in the reference sample. In a specific embodiment, a stabilization or reduction in the amount of cancer stem cells relative to an earlier (previously detected) cancer stem cell amount determined for the subject indicates an improvement in the subject's prognosis or a positive response to the therapy, whereas an increase relative to the earlier cancer stem cell amount indicates the same or worse prognosis, and/or a failure to respond to the therapy.

In some embodiments, a combination of cell surface markers, e.g. CLDN6 combined with other markers typical for cancer stem cells, is utilized in order to determine the amount of cancer stem cells in the sample.

The present invention also provides a kit comprising one or more containers filled with reagents for detecting, determining the amount or monitoring cells expressing CLDN6. In one embodiment, the kit optionally comprises instructions for the use of the reagents for determining cancer stem cells or monitoring the efficacy of a cancer therapy by detecting and/or determining the amount of cells expressing CLDN6, in particular for the use of the reagents in the methods of the invention. In one embodiment, the kit comprises an agent that specifically binds to CLDN6 protein or CLDN6 mRNA. In some embodiments, the agent is an antibody or an antibody fragment. In other embodiments, the agent is a nucleic acid. For nucleic acid detection, the kits generally comprise (but are not limited to) probes specific for CLDN6 mRNA. For Quantitative PCR, the kits generally comprise pre-selected primers specific for CLDN6 nucleic acid sequences. The Quantitative PCR kits may also comprise enzymes suitable for amplifying nucleic acids (e.g., polymerases such as Taq), and deoxynucleotides and buffers needed for the reaction mixture for amplification. The Quantitative PCR kits may also comprise probes specific for CLDN6 nucleic acid sequences. In some embodiments, the Quantitative PCR kits also comprise components suitable for reverse-transcribing RNA including enzymes (e.g. reverse transcriptases) and primers for reverse transcription along with deoxynucleotides and buffers needed for the reverse transcription reaction.

In certain embodiments, the agent is detectably labeled. Further, the kits may comprise instructions for performing the assay and methods for interpreting and analyzing the data resulting from the performance of the assay.

Based on the results obtained (i.e. whether cancer stem cells are present or whether the cancer stem cell amount has stabilized or decreased), the medical practitioner may choose a particular cancer therapy, e.g. a cancer therapy directed against cancer stem cells, or may choose to continue the therapy. Alternatively, based on the result that no cancer stem cells are present or the cancer stem cell amount has increased, the medical practitioner may choose to administer cancer therapy not directed against cancer stem cells or continue, alter or halt the therapy.

In certain embodiments of the present invention, if a reduction in the cancer stem cell population is determined to be inadequate upon comparing the cancer stem cell population in the sample obtained from the patient undergoing the cancer therapy with the sample from the patient taken earlier from the patient, then a medical practitioner has a number of options to adjust the therapy. For example, the medical practitioner can then increase the dosage of the cancer therapy, the frequency of administration, the duration of administration, or any combination thereof. In a specific embodiment, after the determination is made, an additional cancer therapy can be administered to the patient either in place of the first therapy or in combination with the first therapy.

In other certain embodiments, if the reduction in the cancer stem cell population is determined to be acceptable upon comparing the cancer stem cell population in the sample obtained from the patient undergoing the cancer therapy with the sample from the patient taken earlier from the patient, then the medical practitioner may elect not to adjust the cancer therapy. For example, the medical practitioner may elect not to increase the dosage of the cancer therapy, the frequency of administration, the duration of administration, or any combination thereof. Further, the medical practitioner may elect to add additional therapies or combine therapies.

The present invention is further illustrated by the following examples which are not be construed as limiting the scope of the invention.

EXAMPLES

Figure 1:
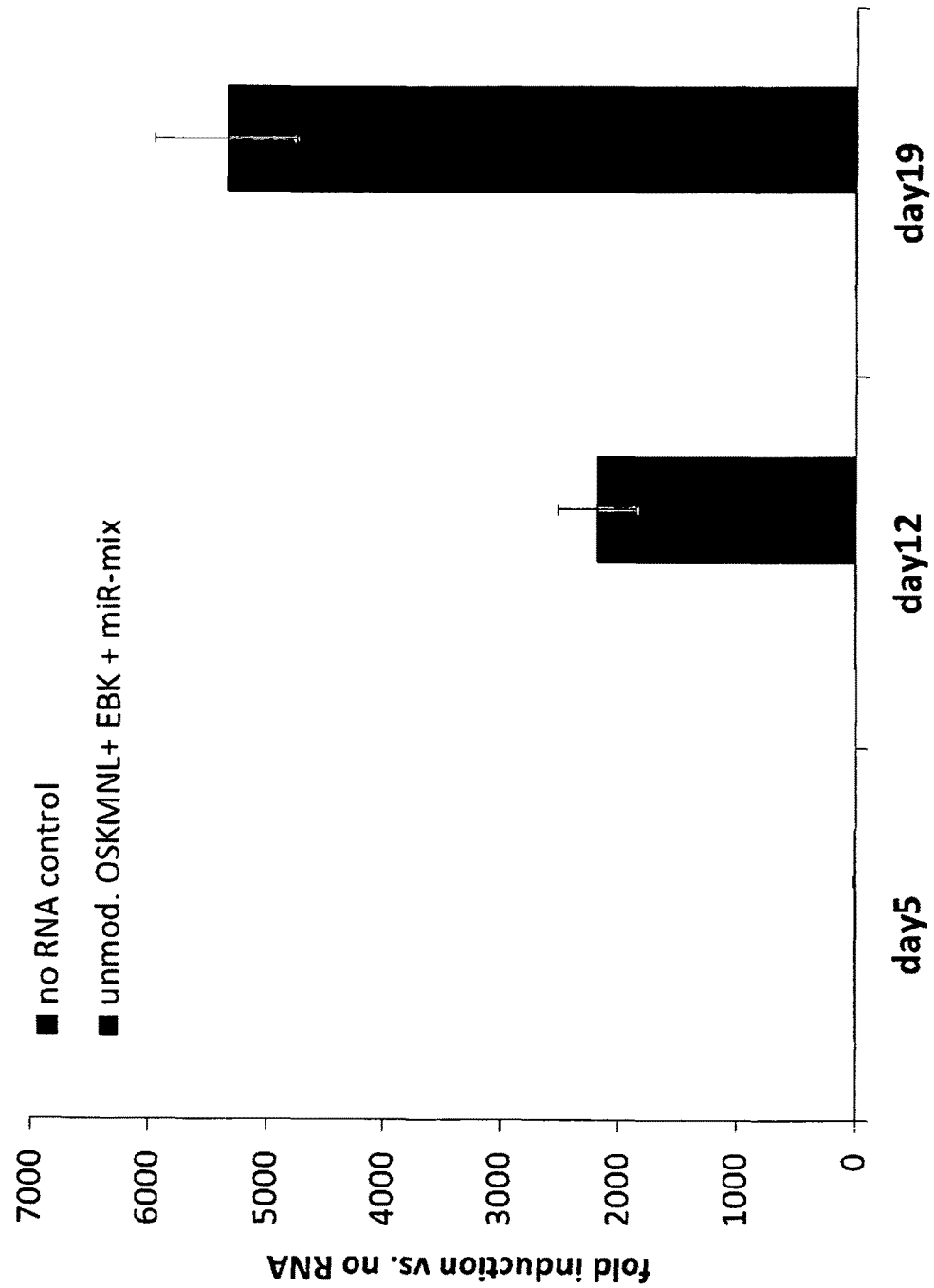
FIG. 1: CLDN6 mRNA is expressed in human iPS cells.
Human foreskin fibroblasts (HFF) were transfected using Lipofectamine RNAiMAX (Life Technologies) either without RNA (no RNA control) or with a reprogramming cocktail (unmod. OSKMNL+EBK+miR-mix) and cells were collected at day 5, 12 and 19 post treatment. RNA was extracted, transcribed into cDNA and afterwards analyzed by quantitative real-time RT-PCR using an ABI PRISM 7300 sequence detection system and software (Applied Biosystems with QuantiTect SYBR green Kit (Qiagen)). Shown is fold induction of CLDN6 expression of cells treated with the reprogramming cocktail (black bars) relative to HFF cells from day 1 of treatment (grey bars). CLDN6 mRNA expression was normalized to mRNA expression of the housekeeping gene HPRT1 OSKMNL=transcription factors OCT4, SOX2, KLF4, cMYC, NANOG und LIN28, EBK=IFN-escape proteins E3, K3 und B18R, miR-mix=miRNA-302a/b/c/d and 367.

Example 1: CLDN6 is Expressed on the Surface of Induced Human Pluripotent Stem Cells To analyze if CLDN6 is expressed in human induced pluripotent stem cells (iPSC), the transcript expression of CLDN6 was analyzed in neonatal HFF (human foreskin fibroblasts, System Bioscience) at several time points of treatment with a reprogramming cocktail (unmodified OSK-MNL+EBK+miR-mix; consisting of in vitro transcribed (IVT) RNA of OSKMNL=transcription factors OCT4, SOX2, KLF4, cMYC, NANOG und LIN28, IVT-RNA of EBK=IFN-escape proteins E3, K3 und B18R and a miRNA mix consisting of miR-302a/b/c/d and 367; according to the protocol described in PCT/EP2012/04673 or mock transfected HFFs (no RNA control) by quantitative real-time RT-PCR (qRT-PCR) using an ABI PRISM 7300 sequence detection system and software (Applied Biosystems with QuantiTect SYBR green Kit (Qiagen)). The cells were cultured in Nutristem serum-free medium (Stemgent, Cambridge (Mass.)) supplemented with 10 ng/ml bFGF and 0.5 µM Thiazovivin. The reprogramming cocktail was transfected using Lipofectamine RNAiMAX (Life Technologies) at day 1, 2, 3, 4, 8, 9, 10 and 11 of the experiment. As a control, the cells were treated with Lipofectamine RNAiMAX only (no RNA control). We detected a clear almost 6000-fold up-regulation of CLDN6 compared to untreated HFF at day 19 of treatment, and at day 12 of treatment we observed an approximately 2000-fold up-regulation of CLDN6 (FIG. 1). Thus, CLDN6 is expressed in human induced pluripotent stem cells (iPSC).

Figure 2:
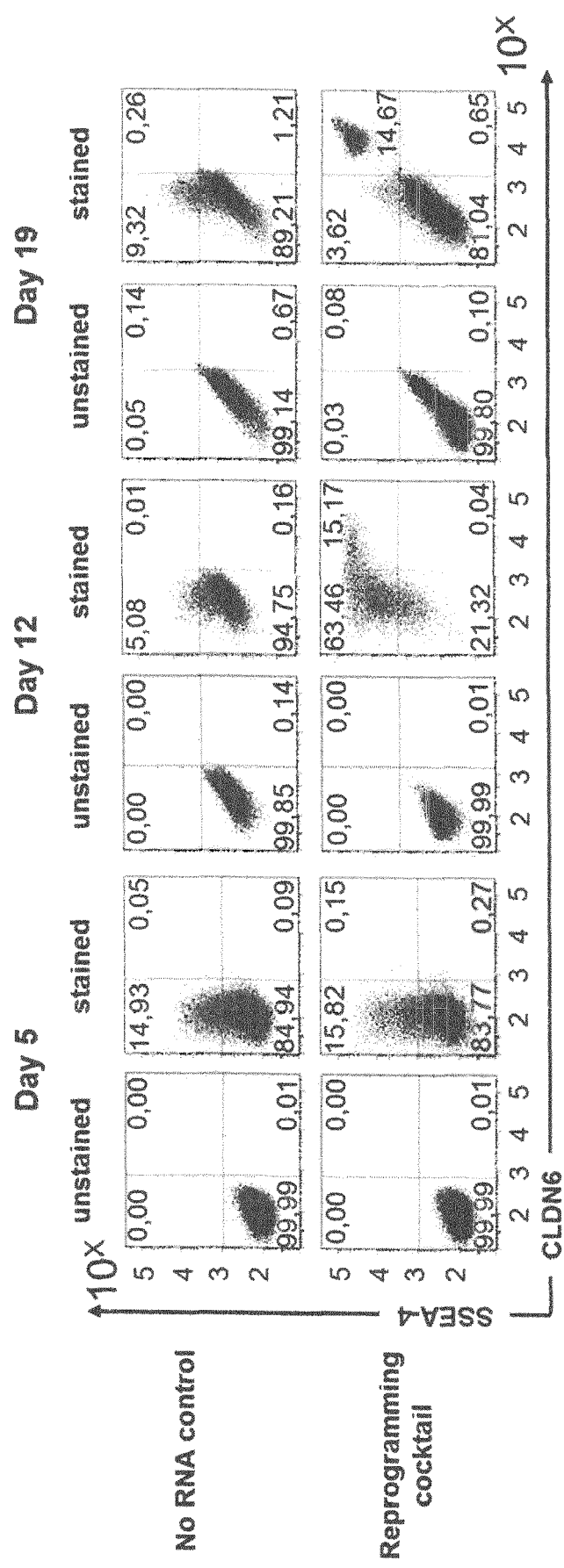
FIG. 2: CLDN6 is expressed on the surface of human iPS cells.
HFF cells were transfected without RNA (no RNA control) or with a reprogramming cocktail (unmod. OSKMNL+EBK+miRmix) and cells were collected at day 5 (A), 12 (B) and 19 (C) post treatment. Cells were stained with 1 µg/ml CLDN6-specific IMAB027-AF647 and SSEA-4-V450 antibody (2.5 µl per test, purchased from BD) for 30 min at 4° C. and surface expression was analyzed by flow cytometry. The experiment was performed in duplicates and representative dot plots are shown. OSKMNL=transcription factors OCT4, SOX2, KLF4, cMYC, NANOG and LIN28, EBK=IFN-escape proteins E3, K3 und B18R, miR-mix=miRNA-302a/b/c/d and 367.

Flow cytometry was used to examine if CLDN6 is also expressed on the surface of iPSC. As the iPSC are grown on HFF feeder cells, we combined the analysis with staining for SSEA-4, a well-accepted stem cell marker, to ensure that iPSCs are specifically detected. For this purpose, HFF cells treated with the reprogramming cocktail or the mock contril (without RNA) were collected at day 5, 12 and 19 of treatment and stained with 1 µg/ml CLDN6-specific IMAB027-AF647 and 2 µl SSEA-4 antibody for 30 min at 4° C. and surface expression was analyzed by flow cytometry. We also included the Viability Dye 7-AAD in our staining protocol in order to exclude dead cells from our analyses. The experiment was performed in duplicates and 50.000 events were recorded from each sample using a BD Canto II Flow Cytometer. Analysis of recorded cells was performed using FlowJo Software and representative dot plots are shown (FIG. 2).

At day 5, CLDN6 is not detectable on the surface HFF neither if treated with the reprogramming cocktail or not. Unexpectedly, we find SSEA-4 to be expressed at 15% of HFF, irrespective if treated with the reprogramming cocktail or not. This could be explained by the fact that the used HFF are neonatal fibroblasts and it is possible that these cells retain certain positivity for SSEA-4. At day 12 of treatment, about 63% of the treated HFF are positive for SSEA-4 and we observe a CLDN6-SSEA-4 double positive fraction of about 15%. On day 19 of treatment, 15% of the treated HFF are positive for CLDN6 and SSEA-4, representing a distinct subpopulation. It is assumed that the CLDN6-SSEA-4 positive subpopulation marks the iPSC only whereas the CLDN6-SSEA-4 negative subpopulation is regarded to be HFF feeder cells or not reprogrammed cells and the SSEA-4 single positive cells represent cells which are at the beginning of reprogramming.

As we find 15% of the HFF cells to be positive for SSEA-4 but not for CLDN6, it is assumed that CLDN6 represents a more specific marker for human iPSC than SSEA-4. SSEA-4 is also expressed in neonatal HFF whereas CLDN6 seems to be specifically expressed only in fully reprogrammed HFF cells which represent the iPSC fraction.

Thus, CLDN6 is specifically expressed on the surface of human iPSC.

Example 2: CLDN6 is Important for Colon Formation of Ovarian Cancer Cells

Figure 3:
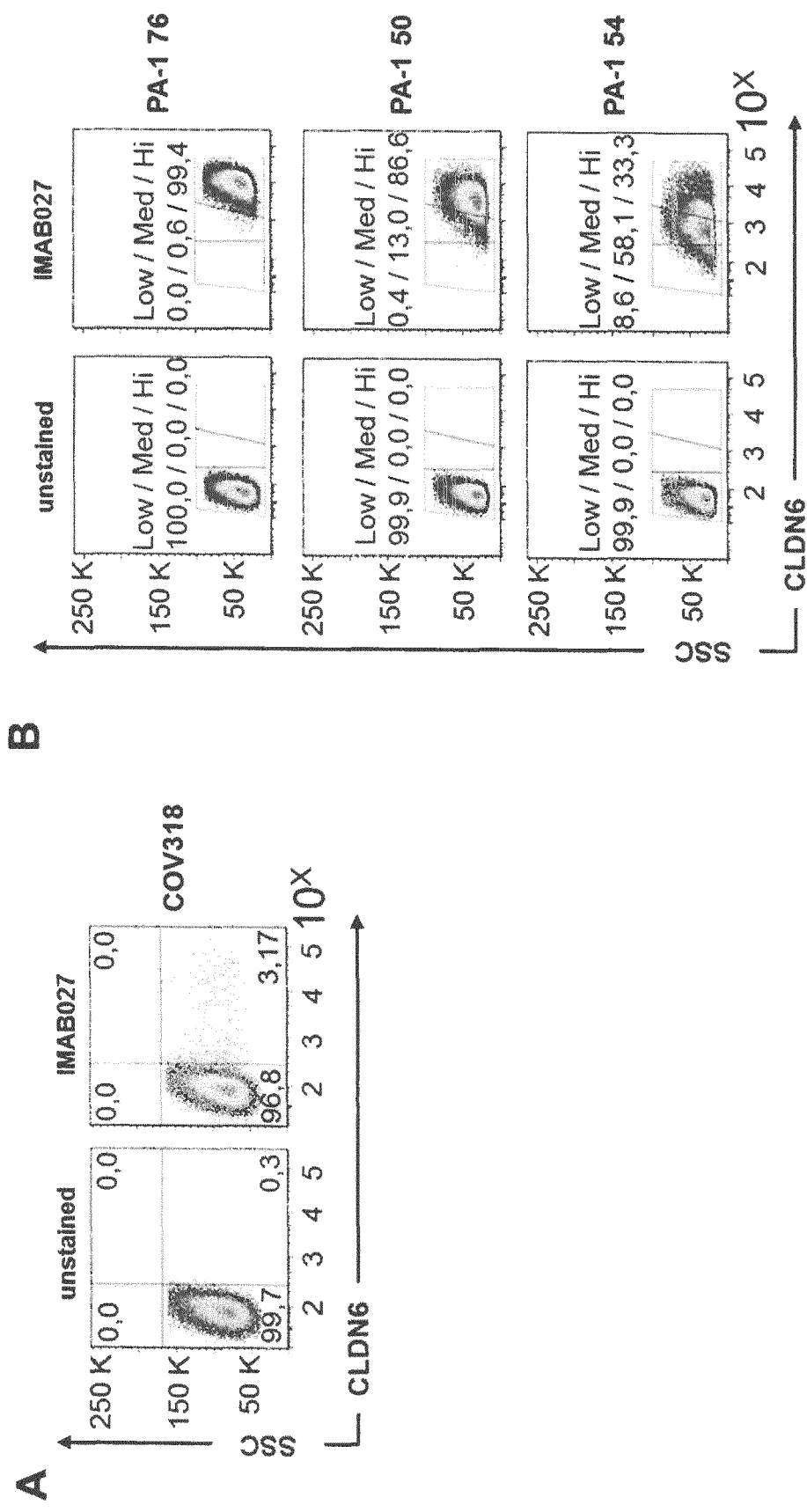
FIG. 3: CLDN6 surface expression in ovarian cancer cell lines.
To analyze CLDN6 expression 1E6 cells were stained with 1 µg/ml IMAB027-AF647 for 30 min at 4° C. and surface expression was analyzed by flow cytometry. In (A) COV318 cells are shown. Experiments were performed in triplicates and one representative dot plot is presented. In (B) PA-1 cells stably transfected with either a control vector (PA-1 76) or with a vector expressing shRNAs against CLDN6 (clones PA-1 50 and PA-1 54) are shown. Experiments were performed in triplicates and one representative dot plot is presented. shRNA=small hairpin RNA

A potent assay to analyze CSC-like properties of tumor cells is the colony formation assay. Using this assay, one can easily examine self-renewal capacity and tumor formation potency of single tumor cells. To analyze if CLDN6 plays a role in tumor formation, we have chosen on the one hand COV318, an ovarian tumor cell line which shows only a subpopulation of CLDN6 positive cells, and on the other hand PA-1, a homogenously CLDN6 expressing cell line, carrying a stable lentiviral small hairpin RNA (shRNA) mediated knockdown of CLDN6 (clones PA-1 50, PA-1 54); cf. FIG. 3.

Figure 4:
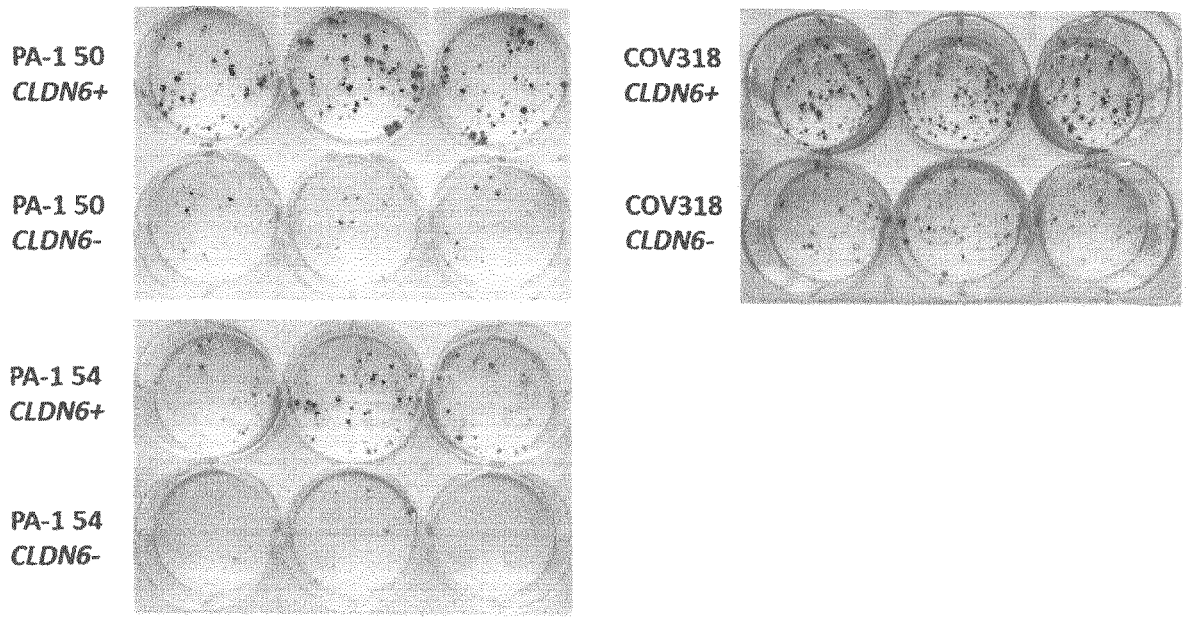
FIG. 4: CLDN6 is important for colony formation of ovarian cancer cells.
Figure 4:
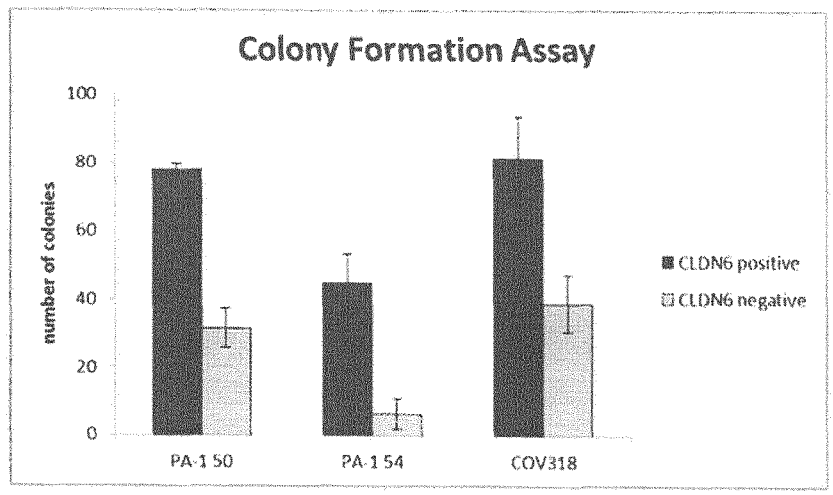

Cells were stained for CLDN6 with 1 µg/ml IMAB027-AF647 for 30 min at 4° C. and were afterwards sorted by FACS (fluorescence activated cell sorting) using a BD FACSAria cell sorter regarding their CLDN6 expression. 500 (PA-1 50, PA-1 54) or 700 (COV318) cells of the CLDN6-positive or -negative subpopulation were sorted directly into wells of a 6-well plate and were allowed to grow for up to 14 days until sufficient colonies have been formed. Twice a week, the culture medium was changed. The colonies were stained and fixed with 0.5% crystal violet in 10% ethanol for 20 min, washed three times with distilled water and allowed to air-dry. Pictures were taken and colonies were counted manually. At least 50 cells were considered to be a colony. In FIG. 4, representative colony formation assays of COV318 and CLDN6-knockdown cell lines PA-1 50 and 54 cells are shown.

Intriguingly, CLDN6 negative cells show a significantly lower colony formation compared to CLDN6 positive cells in both cell lines. From these results we conclude that CLDN6 plays an important role in colony formation capacity, which is an essential feature of cancer stem cells.

Example 3: CLDN6 is Co-Expressed with CSC Markers CD24, CD90 and CD44 in the Ovarian Cancer Cell Line The use of specific surface marker expression profiles is a common strategy for the identification and isolation of CSCs from solid tumors and cell lines. Surface markers used in the literature for the isolation of CSCs from ovarian cancers include CD44, CD24, CD90, CD34, CD117 and CD133. In order to analyze if we can identify CSC subpopulations in ovarian cancer cell lines which contain a small sub-population of CLDN6 positive cells, we set up a FACS panel comprising antibodies against these surface markers (Table 1). Further, we also included an antibody for the detection of CLDN6 in the panel to investigate the percentage of co-localization of CLDN6 with the well-established CSC markers, thus judging the potential of CLDN6 to serve as a marker for CSCs. For this purpose, 1E6 cells of the cell line COV318 were stained for 30 min at 4° C. with the indicated amounts of antibodies (see Table 1) and cells were afterwards analyzed by flow cytometry for their surface marker expression profile. We also included the Viability Dye eFluor®506 in our staining protocol in order to exclude dead cells from our analyses. The experiment was performed in triplicates and 50.000 events were recorded from each sample using a BD Canto II Flow Cytometer. Analysis of recorded cells was performed using FlowJo Software.

TABLE 1

CSC FACS panel. FACS panel used for the analysis of CSC marker and CLDN6 expression in ovarian cancer cell lines is shown. Amounts of antibodies used for the corresponding markers and coupled fluorochromes are listed.

| Surface Marker | Amount of antibody/Test | Fluorochrome of antibody |
| --- | --- | --- |
| CD44 | 5 μl/100 μl test | FITC |
| CD133/1 | 2 μl/100 μl test | PE |
| CD90 | 2.5 μl/100 μl test | PerCP-Cy™ 5.5 |
| CD117 | 1 μg/100 μl Test Biotin 0.05 μg/100 μl Test SA | APC-Cy7 |
| CD34 | 5 μl/100 μl test | Brilliant Violet™ 421 |
| CD24 | 2 μl/100 μl test | PE-Cy7 |
| CLDN6 | 0.25 μl/100 μl test | Alexa Fluor® 647 |
| live/dead | 0.2 μl/200 μl PBS | Fixable viability dye eFluor® 506 |

FACS analyses revealed that COV318 cells express subpopulations of the CSC marker CD44, CD90 and CD24 and that CLDN6 co-localizes at least partly with all three markers (FIG. 5A). We then used different gating strategies to calculate percentages of co-localization of all four markers. First, we calculated the percentage of CD44, CD24, CD90 and CLDN6 positive cells in the whole viable cell population. We found that 0.18% of viable cells are positive for all four markers. Next, we then calculated the percentage of CD44, CD24 and CD90 positive cells in the viable cell population, which could represent the CSC fraction. We found 0.23% of cells to be positive for all three markers when put into relation to the whole viable cell population, while when set into relation to the CLDN6-positive sub-population we found a fraction of 20.1% of cells to be triple positive indicating an 87 fold concentration of the three markers in the CLDN6-positive sub-fraction. In the last step we then calculated the percentage of CLDN6 positive cells on the one hand in the whole viable cell population and on the other hand in the CD44/CD24/CD90 positive sub-population. We found a concentration of CLDN6 expressing cells from 0.91% in the whole cell population to 66.87% in the CSC fraction, indicating a 74-fold increase (FIG. 5B).

Together, these data show that CLDN6 is accumulated in the CSC fraction and vice versa CSC markers are enriched in the CLDN6-positive sub-population. These findings indicate that CLDN6 is a marker for CSCs.

Example 4: Enrichment of CLDN6 Expressing Cells Leads to an Accumulation of the Established CSC Markers CD44 CD24 and CD90

Isolated CSC fractions from cell lines and tumors have been shown to be often enriched for CSC markers, such as CD44 and CD24. To analyze the potential of CLDN6 to serve as a novel marker for CSCs, we investigated whether cell isolation of CLDN6-positive fractions from bulk cells leads to an accumulation of established ovarian CSC markers.

For this purpose, COV318 cells were stained with 0.5 μg/ml IMAB027 for 30 min at 4° C. followed by incubation with goat anti-human IgG secondary antibody (1:300) for 10 min at 4° C. and afterwards CLDN6-positive and CLDN6-negative cell fractions were isolated from COV318 cells by FACS sorting using a BD FACSAria cell sorter. Selected cells were then expanded for 10 days under standard growth conditions. 1E6 cells of both sub-populations were stained for the CSC markers CD44, CD24, CD90, CD34, CD117 and CD133 for 30 min at 4° C. (for details see Table 1) and analyzed by flow cytometry for their surface marker expression profile. 50.000 events were recorded from each sample using a BD Canto II Flow Cytometer and analysis of recorded cells was performed using FlowJo Software.

FACS analyses showed that about 50% of cells of the CLDN6-positive sorted fraction are still positive for CLDN6 following cultivation under standard conditions for 10 days, while CLDN6-negative sorted cells are completely negative for CLDN6. Importantly, we found that the CLDN6-positive fraction showed an accumulation of the CSC markers CD44, CD24 and CD90 when compared to the CLDN6-negative cell fraction of COV318 cells. Representative dot plots of the different samples are shown in FIG. 6A. Further quantification of the expression levels of these markers revealed a 99-fold enrichment of CD44, an 8-fold enrichment of CD90 and a 33-fold enrichment of CD24 when CLDN6-positive and CLDN6-negative sub-populations were compared (FIG. 6B).

These findings demonstrate that CLDN6 can be used as a selection marker to separate CSC fractions from bulk cell lines indicating that CLDN6 is a novel CSC marker.

Example 5: CLDN6 High Express in Cell Lines Show an Enrichment of CSC Markers Compared to CLDN6 Low Expressing Cells CLDN6 has been shown to be highly expressed in germ cell tumors, ovarian adenocarcinomas and some cancers with primitive phenotype. In case that CLDN6 is a CSC marker we would expect an accumulation of cells with CSC-like characteristics in such cell lines or tumors and thus an accumulation of CSC marker positive cells.

We investigated four CLDN6-high expressing cell lines, the ovarian carcinoma cell lines OV90 and PA-1 and the testis carcinoma cell lines NEC-8 and NEC-14, for their expression levels of established CSC markers. For this purpose, 1E6 cells of each cell line were stained for the surface markers CD44, CD24, CD90, CD34, CD117 and CD133 as well as for CLDN6 for 30 min at 4° C. (for details see Table 1) and cells were afterwards analyzed by flow cytometry for their expression profiles. Experiments were performed in triplicates and 50.000 events were recorded from each sample using a BD Canto II Flow Cytometer and analysis of recorded cells was performed using FlowJo Software. Dead cells were excluded from analysis by counterstaining of cells with the viability dye eFluor®506. Representative dot plots from each sample are shown in FIG. 7.

FACS analyses revealed that all cell lines investigated are about 95% positive for CLDN6. As expected, these CLDN6-high expressing cell lines show besides CLDN6 also an accumulation of established CSC markers, with OV90 cells showing high expression of CD44, CD133, CD24 and CD117, PA-1 cells showing high expression of CD44, CD133, CD90 and CD117 and NEC-8 and NEC-14 cells showing elevated expression levels of the markers CD133, CD90, CD24 and CD117.

These findings indicate that CLDN6-high expressing cell lines are enriched for CSC-like cells and further support that CLDN6 is a CSC marker.

Example 6: Treatment of Advanced Human Xenoaraft Tumors with a Combination of a CLDN6 Antibody and Chemotherapeutic Drugs Inhibits Tumor Cell Growth and Prolongs Survival in a Synergistic Manner Hsd:Athymic Nude-Foxn1$^{nu}$ mice were engrafted with human cancer cell lines. After tumors have established, tumor-bearing mice were grouped and received a CLDN6-specific monoclonal antibody (IMAB027), a chemotherapeutic drug or a combination of both. The control group received antibody buffer (vehicle control).

Specifically, for treatment of human ES-2(CLDN6) xenograft tumors, the human ovarian carcinoma cell line ES-2 stably transfected with human CLDN6 was cultivated in Minimum Essential Media (Life Technologies) containing 1× non-essential amino acids solution (Life Technologies), 700 µg/ml G418 (Life Technologies) and 10% FCS (Life Technologies) at 37° C. in a humidified incubator with 5% $CO_2$. For engraftment, 6 week-old female Hsd:Athymic Nude-Foxn1$^{nu}$ mice were subcutaneously inoculated with $5×10^6$ ES-2(CLDN6) cells in 200 µl PBS into the flank. On day 3 post subcutaneous tumor inoculation, mice were treated with either saline control, antibody or chemotherapeutic drug monotherapy and antibody/cytostatic drug combination therapy groups (n=12 per group). 15 mg/kg paclitaxel or a saline control were administered on day 3, 10 and 17 post engraftment. Antibody maintenance treatment started on day 4 with three times a week 35 mg/kg IMAB027 or a vehicle control (IMAB027 buffer) bolus injections (alternating i.v./i.p./i.p.). Tumor burden and animal health were monitored twice a week. Mice were sacrificed, when the tumor achieved a volume to a maximum of 1400 mm$^3$ or when the tumor became ulcerous. Inhibition of tumor growth was analyzed using the Kruskal-Wallis test and the post-hoc Dunn's multiple comparison test.

For treatment of advanced human NEC14 xenograft tumors the human testicular germ cell tumor cell line NEC14 was cultivated according to the instructions of the supplier in RPMI 1640 medium GlutaMAX™ (Life Technologies) containing 10% FCS (Life Technologies) at 37° C. in a humidified incubator with 5% $CO_2$. For engraftment, 6-8 week-old female Hsd:Athymic Nude-Foxn1$^{nu}$ mice were subcutaneously inoculated with $2×10^7$ NEC14 cells in 200 µl PBS into the flank. In the advanced treatment study, tumors were grown to a volume between 50 and 150 mm$^3$ and mice were grouped into control, antibody or cytostatic drug monotherapy and antibody/cytostatic drug combination therapy groups (n=19 per group) before treatment. 6 days post engraftment, the drugs alone or in combination or a vehicle control (saline) were administered as follows: 1 mg/kg cisplatin bolus i.p. injections on day 6, 7, 8, 9 and 10; 30 mg/kg carboplatin bolus i.p. injections on day 6, 13 and 20 and antibody maintenance treatment with three times a week 35 mg/kg IMAB027 or a vehicle control (IMAB027 buffer) bolus injections (alternating i.v./i.p./i.p.). Tumor burden were monitored twice a week. Mice were sacrificed, when the tumor achieved a volume to a maximum of 1400 mm$^3$ or when the tumor became ulcerous. Inhibition of tumor growth was analyzed using the Kruskal-Wallis test and the post-hoc Dunn's multiple comparison test.

Compared to the control group, the treatment of human ES-2(CLDN6) xenograft tumors ectopically expressing human CLDN6 with paclitaxel is not effective and does not show anti-tumoral activity. In contrast, IMAB027 inhibits tumor growth and prolongs survival in mice. The treatment with a combination of IMAB027 and paclitaxel synergistically inhibits tumor growth (FIG. 8).

Furthermore, both cisplatin and IMAB027 as single agents are able to highly significantly reduce tumor growth in NEC14 tumor bearing animals. However, after the initial tumor growth inhibition we observed recurrent tumor growth in most animals. In a combination therapy approach cisplatin and IMAB027 act synergistically and do not only inhibit tumor growth, but evoke a complete NEC14 tumor remission. Survival data most impressively show the therapeutic efficacy of IMAB027 in combination with cisplatin. Compared to the single agent approaches almost all mice treated with IMAB027 together with cisplatin were still alive 90 days after tumor engraftment (FIG. 9).

In the advanced treatment of mice-bearing NEC14 xenograft tumors, other platin-derivatives such as carboplatin show only very limited anti-tumoral efficacy. The combination of carboplatin with IMAB027, however, results in synergistic tumor inhibiting effects with highly efficient inhibition of tumor growth and prolongation of survival (FIG. 10).

Thus, the combination of a CLDN6-specific antibody with chemotherapeutic drugs increases inhibition of tumor growth and prolongs survival of mive engrafted with human tumor cells. The combination of the antibody with chemotherapeutic drugs produces a synergistic effect regarding the inhibition of tumor cell growth and prolongation of survival.

Example 7: CLDN6 is a CSC Marker

Example 7.1: CLDN6 is Important for the Spheres Forming Behavior of Ovarian Cancer Cells Another potent assay to analyze CSC-like properties of tumor cells is the spheres forming assay. Using this assay, one can easily examine the capacity of cells for anchorage independent growth, a typical feature of CSCs. To analyze if CLDN6 plays a role in anchorage independent growth of tumor cells, we chose COV318 cells, the ovarian tumor cell line which only contains a subpopulation of CLDN6 positive cells. COV318 cells were sorted regarding their CLDN6 expression and CLDN6 positive and negative cell populations were allowed to form spheres for 21 days under stem cell-specific conditions. Spheres Forming Assays revealed that CLDN6 positive COV318 cells show the ability to form spheres when cultivated under stem cell-specific conditions, while CLDN6 negative cells almost completely died (FIG. 11A). These findings indicate that the CLDN6 positive fraction represents a stem cell enriched population, which displays the capacity of anchorage independent growth.

In order to define the ability of CLDN6 positive COV318 cells to go through numerous cycles of cell division while maintaining their undifferentiated state we analyzed the spheres' capacity to produce second generation spheres. For this purpose first generation spheres of CLDN6 positive COV318 cells (day 22 post seeding) were dissociated into single cells and were then re-plated. 23 days following re-plating we could clearly observe that a second generation of spheres has formed and these newly formed spheres were morphologically more regular than the initial first generation spheres (FIG. 11B). These observations further confirm that the CLDN6 positive fraction of COV318 cells represents the stem cell fraction of this cell line.

Taken together, these results clearly show that CLDN6 plays a striking role in the anchorage independent growth of ovarian cancer cells, which is an essential feature of cancer stem cells.

Example 7.2: Enrichment of CLDN6-Positive COV318 Cells after Treatment with Chemotherapeutic Drugs In Vitro The ovarian cancer cell line COV318 shows a heterogeneous expression of CLDN6 and a very small subpopulation of cells (~0.3-0.5%) expresses CLDN6. The treatment of COV318 cells with platin-derivatives in vitro generates in each case a residual cell population with a higher percentage (>2%) of CLDN6 positive cells (FIG. 12). The specific accumulation of CLDN6 positive cells after treatment indicates that these cells may have a selective survival or growth advantage during chemotherapy. Resistance to conventional chemotherapy is a feature of CSCs.

Example 7.3: Enrichment of CLDN6-Positive COV318 Cells In Vivo

In previous studies, we found that COV318 cells subcutaneously injected into the flank of athymic nude mice are weakly tumorigenic. In contrast, mice which received COV318 cells by intraperitoneal injection developed malignant ascites and peritoneal tumors within more than 100 days. In contrast to parental COV318 cells (FIG. 13A), the majority of cells isolated from ascites and tumors were CLDN6 positive (FIG. 13B, upper panel). COV318 cells lose CLDN6 expression in vitro again after they have been cultivated under standard conditions (FIG. 13B, lower panel). This means that CLDN6 positive COV318 cells exhibit a greater tumor-forming capacity, suggesting that the small CLDN6 positive subpopulation contains CSCs.

Example 7.4: CLDN6 Correlates with Ovarian Cancer Stem Cell Markers in Primary Tumor Samples As our previous results showed that CLDN6 co-localizes with some CSC markers in ovarian cancer cell lines we next asked whether CLDN6 expression also correlates with CSC markers in primary tumor samples from ovarian cancer patients.

For this purpose, mRNA expression of CLDN6 and selected markers described in the literature to be cancer stem cell specific in ovarian cancer (CTCFL, LIN28B, CD24, GNL3, EpCAM, CD44, ABCG2, ALDH1A1, AMACR, ATXN1, BMI1, BMP4, CD34, CD117, Myd88, Nanog, Notch 1, Pou5F1, CD133, Snail, Sox 2) was analyzed in 42 human ovarian cancer samples by qRT-PCR. A subsequent correlation analysis of CLDN6 with these markers was performed using Spearman's r. Scatter plots from significant correlations as well as a summary of all correlations are shown in FIG. 14.

A positive correlation was found for CLDN6 with CTCFL, LIN28B, CD24, GNL3 and EPCAM, whereas CD44 was found to correlate negatively with CLDN6 in the analyzed ovarian cancer samples (FIG. 14A). For all other investigated markers no significant correlation was observed (FIG. 14B).

These findings further support that CLDN6 is a CSC marker.

Example 8: Anti-Tumoral Activity of Anti-CLDN6 Antibodies is Enhanced by Combination with Chemotherapeutic Drugs

Example 81: Influence of Chemotherapeutic Agents on IMAB27-Mediated ADCC

The influence of chemotherapeutic agents on IMAB027-mediated ADCC was analyzed with COV362(Luc) cells, which were pretreated with carboplatin, gemcitabine, paclitaxel, doxorubicin and topotecan, respectively. Pretreatment of target cells results in increased protein levels of CLDN6 on the cell surface, as shown by flow cytometry (FIGS. 15B, D, F, H and J). Compared to untreated target cells, the maximum lysis of cells treated with chemotherapeutics is increased up to 3-fold (FIGS. 15A, C, F, G and I). In summary, the anti-tumoral activity of IMAB027 can be enhanced in combination with chemotherapeutic drugs.

Example 8.2: The Combination of the Multi-Chemotherapy PEB (Cisplatin, Etoposide and Bleomycin) with IMAB027 Highly Effectively Increases Inhibition of Tumor Growth and Prolongs Survival of Mice Engrafted with the Human Tumor Cell Line NEC14

Hsd:Athymic Nude-Foxn1$^{nu}$ mice were subcutaneously engrafted with the human testicular germ cell tumor cell line NEC14. Mice with very advanced tumors were randomized and treated with the antibody IMAB027, the multi-chemotherapy PEB (cisplatin, etoposide and bleomycin) or a combination of IMAB027 and PEB.

Compared to untreated and IMAB027-treated mice the multi-chemotherapy highly significantly reduces tumor growth (FIG. 16A). However, after the tumors initially respond to the PEB treatment they started to grow in most animals at day 30. A sustainable inhibition of tumor growth was only achieved in a combined approach in which PEB and IMAB027 act synergistically together (FIG. 16B). Untreated mice showed a median survival of 30 days, whereas median survivals of 34 and 97 days were observed in mice treated with IMAB027 and PEB, respectively. In the group treated with PEB, 3/14 (21%) mice showed complete tumor remission and 1/14 (7%) mice presented with a residual tumor mass of ~30 mm$^3$ at the end of the study. Surprisingly, complete tumor regression was observed in 12/14 (86%) mice treated with PEB in combination with IMAB027. 11 mice were cured without any relapse for over 6 months and one tumor-free mouse was euthanized on day 93 due to poor general health conditions (FIG. 16C). The study showed that animals with very advanced human NEC14 testicular tumors which received PEB in combination with IMAB027 had a significantly longer survival and a significantly higher response rate compared with animals treated with the multi-chemotherapy alone.

Example 9: Anti-CLDN6 Antibody-Drug Conjugates are Highly Effective in Treating CLDN6-Expressing Tumors

Example 9.1: Binding and Anti-Tumoral Activity of Toxin-Conjugated IMAB027 In Vitro Relative binding affinities of the IMAB027-drug conjugates IMAB027-DM1 and IMAB027-vcMMAE were tested on the ovarian cancer cell line OV90 using flow cytometry. In the saturation binding experiment the concentration of the antibodies was plotted against the median of fluorescence intensity (MFI) and the EC50 (antibody concentration that binds to half the binding sites at equilibrium) and the maximum binding was calculated by nonlinear regression. Compared to non-conjugated IMAB027, both IMAB027-drug conjugates exhibited similar low EC50 values and saturation of binding was achieved at low concentrations (FIG. 17A). The cytotoxic activities of the IMAB027-drug conjugates were determined with OV90 cells using the XTT proliferation assay. Dose-response curves show similar inhibition of tumor cell growth for IMAB027-DM1 and IMAB027-vcMMAE in vitro (FIG. 17B). In summary, IMAB027 conjugated to DM1 or vcMMAE bind with similar relative affinities to CLDN6 positive target cells highly efficiently inducing tumor cell killing.

Example 9.2: Treatment of Advanced Human Xenograft Tumors with a Toxin-Conjugated IMAB027 Anti-CLDN6 Antibody Inhibits Tumor Cell Growth, Prolongs Survival and Mediates Complete Tumor Regression The anti-tumoral activity of the CLDN6-specific antibody IMAB027 conjugated to a cytotoxic drug was tested in mice that were engrafted with CLDN6 positive human carcinoma cell lines. In this targeted approach, IMAB027 was attached to maytansinoid DM1 or the auristatin E (MMAE) and the tumor growth was monitored in athymic nude-Foxn1$^{nu}$ mice bearing advanced xenograft tumors.
Treatment of an Advanced Human OV90 Ovarian Subcutaneous Xenograft Tumor Model:

The anti-tumoral effect of toxin-conjugated IMAB027 was tested in mice with advanced human xenograft tumors with homogeneous CLDN6 expression. Treatment was started at day 10 after tumor cell engraftment. After a single i.v. bolus injection, IMAB027-DM1 and IMAB027-vcMMAE highly significantly inhibited tumor growth of OV90 ovarian carcinoma cell xenografts homogenously expressing CLDN6 (FIGS. 18 and 19A). More importantly, the single application of 16 mg/kg IMAB027-vcMMAE resulted in complete tumor remission in 60% of treated mice (FIG. 19B).
Treatment of an Advanced Human PA-1 Ovarian Subcutaneous Xenograft Tumor Model:

The anti-tumoral effect of toxin-conjugated IMAB027 was also tested in an advanced xenograft tumor model with heterogeneous CLDN6 expression. After subcutaneous engraftment, PA-1 xenograft tumors lose CLDN6 expression after a certain period of time (FIG. 20C). Treatment was started at day 15. At that time, PA-1 xenograft tumors begin to lose CLDN6 expression. Animals received 4, 8 or 16 mg/kg IMAB027-vcMMAE by a single i.v. bolus injection. Control animals received unconjugated IMAB027 or vehicle control buffer instead.

The treatment with IMAB027-vcMMAE highly significantly inhibited tumor growth of PA-1 xenografts and prolonged survival of tumor-bearing mice, while IMAB027 or IMAB027-DM1 (data not shown) did not affect PA-1 tumor growth (FIGS. 20A and B).

The reduced level of CLDN6 positive tumor cells in the tumor bulk is probably responsible for the weak anti-tumoral activity of IMAB027 and IMAB027-DM1 in this in vivo tumor model. IMAB027-DM1 is conjugated via a non-cleavable linker to the non-membrane-permeable toxin DM1. In contrast, IMAB027-vcMMAE is conjugated to the cell membrane-permeable toxin MMAE via a cathepsin cleavable linker. The release of membrane-permeable forms of MMAE after cellular processing facilitates the killing of tumor cells lacking the particular epitope (bystander effect). Therefore, treatment with IMAB027-vcMMAE is highly effective in eradicating PA-1 tumors containing both CLDN6 positive and CLDN6 negative cells.

In summary, IMAB027-vcMMAE is highly efficient in killing human xenograft tumors with heterogeneous CLDN6 expression by target cell-activated killing of bystander cells.
Treatment of an Advanced Human MKN74 Gastric Subcutaneous Xenograft Tumor Model:

In contrast to the PA-1 xenograft tumors which lose CLDN6 expression in advanced tumors, MKN74 xenograft tumors gain CLDN6 expression. As shown by flow cytometry using the CLDN6-specific antibody IMAB027<0.3% cells of the gastric cancer cell line MKN74 are CLDN6 positive in vitro. Interestingly, a considerable number of tumor cells exhibits CLDN6 expression after subcutaneous engraftment in athymic nude mice (FIG. 21C). Treatments of established MKN74 xenograft tumors with 16 mg/kg IMAB027-vcMMAE resulted in a highly significant inhibition of tumor growth and prolong survival (FIGS. 21A and B).

The tumor growth inhibition observed with IMAB027-vcMMAE can be caused by target cell-activated killing of bystander cells.
Treatment of an Advanced Human PA-1 Ovarian Intraperitoneal Xenograft Tumor Model:

In addition to the treatment of s.c. xenograft tumors, toxin-conjugated IMAB027 antibodies were also tested for their anti-tumoral activity in an i.p. xenograft tumor model using PA-1 cells ectopically expressing luciferase for in vivo monitoring (FIG. 22). Mice received 16 mg/kg IMAB027-DM1 or 16 mg/kg IMAB027-vcMMAE by a single bolus i.v. injection on day 14 after tumor cell engraftment.

Measurement of bioluminescence intensities in vivo revealed an inhibited tumor growth of peritoneal PA-1 metastases after treatment with IMAB027-DM1. Furthermore, IMAB027-veMMAE showed a significantly higher anti-tumoral effect than IMAB027-DM1 or vehicle with complete regression of peritoneal tumors in 100% of the animals (FIG. 22).

In summary, IMAB027-vcMMAE and IMAB027-DM1 are highly effective without showing toxic side effects in the concentration range tested in vivo. IMAB027-DM1 significantly inhibited tumor growth of subcutaneous xenograft tumors and decreased tumor growth of peritoneal xenograft tumors. IMAB027-vcMMAE highly significantly inhibited tumor growth and prolonged survival of animals with subcutaneous or peritoneal human xenograft tumors with homogeneous or even heterogeneous CLDN6 expression. Most impressively, a large part of tumor-bearing animals were cured after the treatment with the MMAE-conjugated antibody. The outstanding anti-tumoral activity of IMAB027-vcMMAE, especially observed in animals whose tumors exhibited heterogeneous CLDN6 expression, demonstrates that IMAB027-vcMMAE conjugates are suitable to treat tumors with low percentage of CLDN6 positivity.

Example 9.3: Endocytosis of CLDN6-Specific Antibodies Depends on their Affinity and the CLDN6 Binding Epitope The cytotoxic efficacy of toxin-conjugated antibodies strictly depends on their target-mediated potential for internalization. Thus, the generation of antibodies with high endocytosis rates is the essential key factor in the development of toxin-conjugated antibodies.

The efficiency of endocytosis was tested in vitro by incubating endogenously CLDN6 expressing human carcinoma cells together with CLDN6-reactive monoclonal chimeric antibodies and anti-human Fab fragments that are conjugated with the toxin saporin. The internalization of CLDN6-bound antibody/Fab-saporin complexes results in the specific killing of the cells and can be measured using a cell viability assay. Screening of different CLDN6-reactive antibodies demonstrates, that endocytosis not only depends on the binding affinity of an antibody but also on the antigenic epitope. We observe that binding of CLDN6-specific antibodies to an epitope in the first extracellular loop of CLDN6 supports endocytosis in OV-90 and PA-1 human carcinoma cells. Noteworthy, the CLDN6-reactive antibody 5F2D2 that binds with similar to higher affinity but to another epitope shows a lower cytotoxic potential in this assay (FIG. 23).

Example 10: Materials and Methods Used in the Above Examples 7 to 9

Cell Culture:

COV362(Luc) and PA-1(Luc) cells stably expressing a luminescent reporter gene were generated by stable transfection of the cell lines COV362 (ECACC, 07071910) and PA-1 (ATCC, CRL-1572) with firefly luciferase, respectively.

NEC14 (JCRB, 0162) and MKN74 (JCRB, 0255) cells were cultured in RPMI1640 medium (Gibco, 61870-010) supplemented with 10% heat-inactivated FCS (Gibco, 10270-106). COV318 (ECACC, 07071903) and COV362 (Luc) cells were cultured in DMEM (Gibco, 41965-039) containing 2 mM GlutaMAX (Gibco, 35050-038) and 10% heat-inactivated FCS. PA-1 and PA-1(Luc) cells were cultured in MEM (Gibco, 31095-029) supplemented with 1.5 g/l sodium bicarbonate (Invitrogen, 25080), 1 mM sodium pyruvate (Invitrogen, 11360), 1% non-essential amino acids (Gibco, 11140-035) and 10% heat-inactivated FCS. OV90 (ATCC, CRL-11732) cells were cultured in a 1:1 mixture of MCB105 (Sigma, M6395) and 199 medium (Sigma, M4530) supplemented with 1.5 g/l sodium bicarbonate and 15% heat-inactivated FCS. Cells were grown at 37° C. and 5% $CO_2$.

Determination of CLDN6 Expression by Flow Cytometry:

Cells were harvested with 0.05% Trypsin/EDTA (Gibco, 25300-054), washed with FACS buffer (PBS containing 2% FCS (Gibco, 10270-106) and 0.1% sodium azide (Applichem, A1430) and resuspended in FACS buffer at a concentration of $2\times10^6$ cells/ml 100 µl of the cell suspension were incubated with of the anti-CLDN6 antibody IMAB027 or an isotype control human IgG1 antibody (Sigma, 15154) at a concentration of 2.5 µg/ml for 30 min at 4° C. The cells were washed three times with FACS buffer and incubated with an APC-conjugated F(ab')$_2$ fragment goat anti-human IgG (Jackson ImmunoResearch, 109-136-170) diluted 1:200 in FACS buffer for 30 min at 4° C. The cells were washed twice and resuspended in FACS buffer. The binding was analysed by flow cytometry using a BD FACSArray (BD Biosciences) and FlowJo software (Tree Star Inc.). The live/dead dye propidium iodide (Sigma, P4864) was used to exclude dead cells from the analysis.

Treatment of COV318 Cells with Platin-Derivatives:

COV318 cells ($1.2\times10^6$ cells per 100 mm cell culture dish) were grown under standard conditions. After 24 h, cells were treated with 0.5 µg/ml cisplatin or 2 µg/ml carboplatin and incubated for 96 h. The medium was changed and the treated cells were grown under standard growth conditions. After 3 and 6 days, cells were analyzed for CLDN6 expression by flow cytometry.

Antibody-Dependent Cellular Cytotoxicity (ADCC) after Treatment with Cytostatic Agents:

The human ovarian carcinoma cell line COV362 stably transfected with luciferase as a reporter was used to determine the influence of carboplatin and paclitaxel on IMAB027-mediated ADCC. COV362(Luc) cells ($3\times10^6$ cells per 150 mm cell culture dish) were grown under standard conditions. After 24 h, cells were treated with 5 ng/ml paclitaxel, 20 µg/ml carboplatin, 25 ng/ml gemcitabine, 20 ng/ml doxorubicin or 7.5 ng/ml topotecan and incubated for 4 days. The medium was changed and the treated cells were grown under standard growth conditions for further 3 days for carboplatin and gemcitabine or 10 days for paclitaxel, doxorubicin or topotecan.

The cells were harvested with 0.05% Trypsin/EDTA (Gibco, 25300-054) and adjusted to a concentration of $2\times10^5$ cells/ml in DMEM containing 2 mM glutamine (Gibco, 25030-081) and 20 mM HEPES (Gibco, 15630-056). $1\times10^4$ cells per well were seeded into a white 96-well PP-plate and incubated for ~5 h at 37° C. and 5% $CO_2$.

PBMC (peripheral blood mononucleated cells) were isolated from human donor blood samples by density gradient centrifugation using Ficoll Hypaque (GE Healthcare, 17144003). The PBMC containing interphase was isolated and cells were washed three times with PBS containing 2 mM EDTA. PBMC were resuspended in X-Vivo 15 medium (Lonza, BE04-418Q) at a concentration of $1.6\times10^7$ cells/m and stored at 37° C. and 5% $CO_2$ until assaying.

25 µl IMAB027 and isotype control antibody were added to the cells at indicated concentrations. After that, 25 µl of the PBMC suspension were added and the cells were incubated for 24 h at 37° C. and 5% $CO_2$.

After adding 10 µl 8% Triton X-100 (Sigma, T8787) in PBS to the total lysis controls and 10 µl PBS to the max viable cells controls and to the samples, 50 µl luciferin mix (3.84 mg/ml D-luciferin (Sigma Aldrich, 50227) and 160 mM HEPES in ddH$_2$O) were added and the cells were incubated in the dark at room temperature for 90 min. The bioluminescence was measured using a luminometer (Infinite M200, TECAN). Results are given as integrated digital relative light units.

The specific lysis is calculated as:

$$\text{specific lysis [\%]} = 100 - \left[\frac{(\text{sample} - \text{total lysis})}{(\text{max viable cells} - \text{total lysis})} \times 100\right]$$

max viable cells: 10 µl PBS, without antibody
total lysis: 10 µl 8% Triton X-100 in PBS, without antibody Intraperitoneal Engraftment of COV318 Cells in Athymic Nude Mice:

In vivo tumorigenicity of the human ovarian carcinoma cell line COV318 and accumulation of CLDN6 positive cells were tested in mice. Therefore, $2\times10^7$ COV318 cells resuspended in PBS were injected intraperitoneally into 6-8 week-old female Hsd:Athymic Nude-Foxn1$^{nu}$ mice. Mice were monitored on a daily basis. Once life-threatening symptoms became markedly manifest the animal was euthanized. Tumor and ascites cells were isolated and cultivated for further analysis. Tumors were mechanically dissociated, passed through a mesh and washed with DMEM medium (Gibco, 41965-039). To obtain a single cell suspension, the tumor cells were treated with accutase (Life Technologies, A11105-01) for 30 min at 37° C., passed through a 40 m cell strainer and washed with DMEM medium. Ascites was collected and contaminating red blood cells were removed by using ACK (ammonium-chloride-potassium) lysing buffer (Invitrogen, A10492-01). Tumor and ascites cells were grown under standard conditions using standard COV318 medium supplemented with penicillin/streptomycin (Gibco, 15140). Cells were screened for CLDN6 expression by flow cytometry.

Treatment of Very Advanced Human NEC14 Xenograft Tumors

For engraftment, 6-8 week-old female Hsd:Athymic Nude-Foxn1$^{nu}$ mice were subcutaneously inoculated with $2 \times 10^7$ NEC14 cells in 200 µl PBS into the flank. In the very advanced treatment study, tumors were grown for 13 days to a volume of maximal 170 mm³ and mice were grouped into control, IMAB027, PEB (cisplatin, etoposide, bleomycin) and IMAB027/PEB groups (n=14 per group) before treatment.

13 days post engraftment, the drugs were administered as follows: 1 mg/kg cisplatin bolus i.p. injections on day 13, 14, 15, 16 and 17; 5 mg/kg etoposide bolus i.p. injections on day 13, 14, 15, 16 and 17; 10 mg/kg bleomycin bolus i.p. injections on day 13, 17 and 21. IMAB027 was applied three times a week from day 13 to day 101 by bolus alternating i.v./i.p./i.p. injections of 35 mg/kg IMAB027. As vehicle controls, mice received drug substance buffer instead of antibody or 0.9% NaCl solution instead of PEB, respectively.

Tumor burden and animal health were monitored twice a week. Mice were sacrificed, when the tumor achieved a volume of 1400 mm³ or when the tumor became ulcerous. Inhibition of tumor growth was analyzed using the Kruskal-Wallis test and the post-hoc Dunn's multiple comparison test.

Spheres Forming Assay:

For spheres forming assay, COV318 cells were stained for CLDN6 with 0.5 µg/ml IMAB027 for 30 min at 4° C. followed by incubation with a goat anti-human IgG secondary antibody (1:300) for 10 min at 4° C. and cells were afterwards sorted regarding their CLDN6 expression using a BD FACSAria cell sorter. $1 \times 10^6$ CLDN6-positive or -negative sorted cells were then seeded into wells of a 6-well Ultra Low Attachment Plate (Corning) in serum-free DMEM/F12 medium containing 0.4% Bovine Serum Albumin, 20 ng/ml basic Fibroblast Growth Factor, 10 ng/ml Epidermal Growth Factor and 5 gi/ml Insulin and cells were allowed to form spheres for 21 days under these stem cell-specific conditions. Medium was exchanged every second day without disrupting the spheres and representative pictures were taken regularly.

For production of second generation spheres, first generation spheres of CLDN6 positive COV318 cells (day 22 post seeding) were dissociated into single cells and were then re-plated into wells of 6-well Ultra Low Attachment Plates. Again, medium was exchanged every second day without disrupting formed spheres and representative pictures were taken regularly.

Quantitative real-time RT-PCR analysis using a Bio Mark™ HD System (Fluidigm):

42 human ovarian cancer samples were analyzed by qRT-PCR with TaqMan® gene expression assays (Life technologies) for selected ovarian cancer stem cell specific factors (CTCFL, LIN28B, CD24, GNL3, EpCAM, CD44, ABCG2, ALDH1A1, AMACR, ATXN1, BMI1, BMP4, CD34, CD117, Myd88, Nanog, Notch 1, PouSF1, CD133, Snail, Sox 2) using a Bio Mark™ HD System (Fluidigm). Isolation of RNA from ovarian cancer samples was performed using RNeasy Mini Kit (Qiagen) and cDNA was synthesized using PrimeScript RT Reagent Kit (Takara Bio Inc.) according to the respective manufacturer's instructions. Samples were prepared and analyzed according to the Fluidigm® Advanced Development Protocol 28—Fast Gene Expression Analysis using TaqMan® GE Assays rev A2. Loading onto 96.96 Gene Expression Dynamic Array IFCs was accomplished by the IFC Controller HX. Chip arrays were analyzed via a Fluidigm BioMark™ HD system. TaqMan PreAmp MasterMix was purchased from Applied Biosystems. Data sets were evaluated according to the ΔΔCt-method. Correlation analysis of CLDN6 with the selected ovarian cancer stem cell markers was performed using Spearman's r. Significance of correlation values was assessed by a test on the correlation coefficients. P-values were adjusted for multiple testing using the method of Benjamini and Hochberg, and adjusted p-values≤0.05 were considered as significant.

Toxin-Conjugation of CLDN6 Antibody

The toxin-conjugations of the monoclonal antibodies were performed at Piramal Healthcare (Grangemouth, UK).

For DM1 conjugation, naked antibodies were modified with SMCC (6× molarity) reacting with free NH2 residues of lysine groups by incubation in PBS (pH 7.2) for 1 h at RT. Subsequently the modified antibodies were dialyzed into 35 mM Citrate buffer (pH 5.0) and linker to antibody ratio was determined using reversed Ellman's assay. DM1 (6× molarity) was conjugated via its sulfhydryl group to the maleimide moiety of the SMCC linker by incubation for 17 h at RT. Conjugated antibodies were dialyzed into formulation buffer (20 mM His, 85 mg/ml sucrose, pH 5.8) and stored at −80° C. Drug antibody ratio was analyzed by UV spectrometry, the monomer content by SEC-HPLC and free drug content by RP-HPLC.

For MMAE conjugation, naked antibodies were dialyzed into PBS (pH 7.2) and modified by thiolation of free NH2 groups of lysine residues using Traut's reagent (2-Iminothiolane) (20× molarity) for 2 h at RT. Subsequently the thiolated antibodies were dialyzed into 35 mM Citrate buffer (pH 5.5) and linker to antibody ratio was determined using reversed Ellman's assay. vcMMAE (6× molarity) was conjugated via the valin of the cathepsin-cleavable linker to the sulfhydryl group of the thiolated antibodies by incubation for 15 h at RT. Conjugated antibodies were dialyzed into formulation buffer (20 mM His, 85 mg/ml Sucrose, pH 5.8) and stored at −80° C. Drug antibody ratio was analyzed by UV spectrometry, the monomer content by SEC-HPLC and free drug content by RP-HPLC.

Determination of Relative Binding Affinities by Flow Cytometry:

Cells were harvested with 0.05% Trypsin/EDTA (Gibco, 25300-054), washed with FACS buffer (PBS containing 2% FCS (Gibco, 10270-106) and 0.1% sodium azide (Applichem, A1430)) and resuspended in FACS buffer at a concentration of $2 \times 10^6$ cells/ml. 100 yl of the cell suspension were incubated for 30 min at 4° C. with IMAB027, IMAB027-DM1 or IMAB027-vcMMAE (titration series from 0.1 ng/ml to 20 µg/ml). The cells were then washed three times with FACS buffer and incubated for 30 min at 4° C. with anti-human IgG (Jackson ImmunoResearch, 109-136-170) diluted 1:200 in FACS buffer. Subsequently, the cells were washed twice and resuspended in 100 µl FACS buffer. Binding was analyzed by flow cytometry using a BD FACSArray (BD Biosciences) and FlowJo software (Tree Star Inc.).

Viability Assay with Toxin-Conjugated IMAB027:

The effect of IMAB027-DM1 and IMAB027-vcMMAE on viability of human tumor cell lines was determined in vitro using a colorimetric assay that detects cellular metabolic activities (Cell Proliferation Kit XTT from AppliChem).

OV90 cells were harvested with 0.05% Trypsin/EDTA (Gibco, 25300-054) and 2500 cells were seeded in 50 µl growth medium in a 96-well culture. After 24 h, concentration series of DM1- and MMAE-conjugated IMAB027 or an isotype control antibody diluted in 50 µl medium were added. Cells were cultivated for 3 to 7 days until the untreated cells reached a confluence of ~80%. Cell viability was analyzed using the AppliChem Cell Proliferation Kit II (AppliChem, A8088-1000) according to the manufacturer's instructions. After 3-5 h incubation with XTT reagent, 100 µl of the cell supernatants were transferred into a new 96 well assay plate and the absorbance was measured at 480 nm (reference 630 nm) using a spectrophotometer (Tecan). Viability was calculated using the following equation:

$$\text{reduction of viability } [\%] = 100 - \left[\frac{(\text{sample} - \text{blank})}{(\text{max. viable cells} - \text{blank})} * 100\right]$$

blank: medium and XTT without cells
max. viable cells: cells, medium and XTT

The EC50 values were determined using the GraphPad Prism 6 software by non-linear regression.

Treatment of Advanced Subcutaneous OV90 Xenograft Tumors:

The human ovary carcinoma cell line OV90 was cultivated under standard conditions. For engraftment, 6-8 week-old female Hsd:Athymic Nude-Foxn1$^{nu}$ mice were subcutaneously inoculated with $1\times10^7$ OV90 cells in 200 µl PBS into the flank. In the advanced treatment study, tumors were grown for 10 days and mice with established tumors of 50-150 mm$^3$ volume were randomized into vehicle and antibody groups (n=10) before treatment. The tumor volume (TV=(length×width$^2$)/2) was monitored bi-weekly. TV is expressed in mm$^3$, allowing construction of tumor growth curves over time.

In the initial dose range finding study, animals were injected once i.v. with vehicle, IMAB027-DM1 (1.78 mg/kg, 5.33 mg/kg or 16 mg/kg) and dissected on day 35 after engraftment. In a second dose range finding study, animals were injected once i.v. with vehicle, IMAB027-vcMMAE (4 mg/kg, 8 mg/kg or 16 mg/kg) or IMAB027-DM1 (1.33 mg/kg, 2.67 mg/kg or 5.33 mg/kg). IMAB027 was applied three times a week by bolus alternating i.v./i.p./i.p. injections of 35 mg/kg IMAB027. Mice were sacrificed when the tumors reached a volume bigger than 1400 mm$^3$ or ulcerated. Inhibition of tumor growth was analyzed using the Kruskal-Wallis test and the post-hoc Dunn's multiple comparison test. Survival was analyzed using the Mantel Cox test.

Treatment of Advanced Subcutaneous PA-1 Xenograft Tumors and Immunhistochemistry of Tumor Sections:

The human ovary carcinoma cell line PA-1 was cultivated under standard conditions. For engraftment, 6-8 week-old female Hsd:Athymic Nude-Foxn1$^{nu}$ mice were subcutaneously inoculated with $1\times10^7$ PA-1 cells in 200 µl PBS into the flank. In the advanced treatment study, tumors were grown for 15 days and mice with established tumors of 40-120 mm$^3$ volume were randomized into vehicle and antibody group (n=10) before treatment. The tumor volume (TV=(length×width$^2$)/2) was monitored bi-weekly. TV is expressed in mm$^3$, allowing construction of tumor growth curves over time.

Animals were injected once i.v. with vehicle, IMAB027-vcMMAE (4 mg/kg, 8 mg/kg or 16 mg/kg) or IMAB027-DM1 (4 mg/kg, 8 mg/kg or 16 mg/kg). IMAB027 was applied three times a week by bolus alternating i.v./i.p./i.p. injections of 35 mg/kg IMAB027. Mice were sacrificed when the tumors reached a volume bigger than 1400 mm$^3$ or ulcerated. Inhibition of tumor growth was analyzed using the Kruskal-Wallis test and the post-hoc Dunn's multiple comparison test. Survival was analyzed using the Mantel Cox test.

To analyze CLDN6 expression during tumor establishment and progression PA-1 tumors of untreated mice were dissected on day 7, 14 and 56, respectively, formalin fixated and embedded in paraffin. 4 µm tissue sections were prepared from each sample FFPE (formalin fixated paraffin embedded) block, mounted on adhesive slides (SuperFrost Ultra Plus, Thermo Fisher Scientific), and baked for 60 min at 60° C. Before staining, the FFPE tissue sections were deparaffinized. The sections were boiled in 10 mM citric acid supplemented with 0.05% Tween-20 (pH 6.0) at 120° C. for 10 min. Endogenous peroxidases were quenched by incubation in 0.3% H$_2$O$_2$ in PBS for 15 min. After washing with PBS, unspecific antibody binding sites were blocked for 30 min with blocking buffer (10% goat serum in PBS) at RT, followed by overnight incubation with 0.2 µg/ml of the primary rabbit anti-Claudin-6 antibody (IBL-America, 18865) diluted in blocking buffer. Samples were then washed 3 times with PBS and incubated with the respective secondary ready-to-use antibody (Power Vision HRP goat anti-rabbit; Immunologic) for 30 min at RT. Visualization was performed for 4:30 min using the substrate-chromogen solution (VectorRed; Vector Laboratories). After counterstaining with hematoxylin, dehydration and mounting, sections were analyzed using a Leica DM2000 microscope.

Treatment of Advanced Subcutaneous MKN74 Xenograft Tumors and Immunohistochemistry of Tumor Sections:

The human gastric carcinoma cell line MKN74 was cultivated under standard conditions. For engraftment, 6-8 week-old female Hsd:Athymic Nude-Foxn1$^{nu}$ mice were subcutaneously inoculated with $1\times10^7$ MKN74 cells in 200 µl PBS into the flank. In the advanced treatment study, tumors were grown for 7 days and mice with established tumors of 200±30 mm$^3$ volume were randomized into vehicle and antibody groups (n=10) before treatment. The tumor volume (TV=(length×width$^2$)/2) was monitored bi-weekly. TV is expressed in mm$^3$, allowing construction of tumor growth curves over time.

Animals received vehicle control buffer or 16 mg/kg IMAB027-vcMMAE on day 8 by a single bolus i.v. injection. Mice were sacrificed when the tumors reached a volume bigger than 1400 mm$^3$ or ulcerated. Inhibition of tumor growth was analyzed using the Kruskal-Wallis test and the post-hoc Dunn's multiple comparison test. Inhibition of tumor growth was analyzed using Mann-Whithney test and the post-hoc Dunn's multiple comparison test. Survival was analyzed using the Mantel Cox test.

CLDN6 target expression on MKN74 cells was analyzed by flow cytometry pre-engraftment and by histochemistry on untreated MKN74 xenografts dissected on day 31.

For immunohistochemistry, tissue sections with a thickness of 3 µm were prepared, mounted on slides and air dried 90 min at RT. All tissue sections were fixed for 10 min in acetone at −20° C. and washed for 5 min in PBS. Endogenous peroxidases were quenched by 15 min incubation with 0.03% hydrogen peroxide (Dakocytomation EnVision System, K4011). After washing with PBS, unspecific antibody binding sites were blocked for 30 min with blocking buffer (10% goat serum in PBS) at RT, followed by 60 min incubation with 5 µg/ml IMAB027-FITC at RT. Samples were then washed 3 times with PBS and incubated with the respective secondary ready-to-use antibody (Bright Vision poly-HRP anti-rabbit IgG, Immunologic, DPVR-110HRP) for 30 min at RT. Visualization was performed for 2:30 min using the substrate-chromogen solution (VectorRed; Vector Laboratories). After counterstaining with hematoxylin, dehydration and mounting, sections were analysed using a Leica DM2000 microscope.

Treatment of Advanced Intraperitoneal PA-1(Luc) Xenograft Tumors:

The human ovarian teratocarcinoma cell line PA-1(Luc) stably expressing firefly luciferase as a luminescent reporter gene was used as an intraperitoneal xenograft tumor model to study the anti-tumoral activity of toxin-conjugated IMAB027 antibodies in vivo. Previous engraftment experiments revealed that the intraperitoneal inoculation of PA-1 (Luc) cells resulted in intraperitoneal tumor nodules.

$1 \times 10^7$ PA-1(Luc) cells resuspended in PBS were injected intraperitoneally into female Hsd:Athymic Nude-Foxn1$^{nu}$. Bioluminescence imaging started at day 14 after tumor cell inoculation and thereafter weekly until study termination. D-luciferin (PerkinElmer, 122796) was dissolved in sterile water and injected intraperitoneally (150 mg/kg, injection volumes 200 µl) 5 min prior to imaging with IVIS Lumina Imaging System (Advanced Molecular Vision). Mice were anesthetized with isofluorane and placed into the dark chamber of IVIS Lumina and photons emitted were quantified for an integration time of 1 min. The intensity of transmitted light originating from luciferase expressing PA-1 cells within the animal was represented as a pseudocolor image, where blue is the least intense and red the most intense bioluminescence signal. Grayscale photographic images of mice were also obtained under LED low light illumination. The images were superimposed using the Living Image software (Xenogen). Comparable illumination settings were used for all images. To quantify the bioluminescence, regions of interest (ROI) were determined and total flux of the respective ROI was measured with a unit of photons/sec (p/s). A background bioluminescence value obtained from a non-signal emitting region on the animal was subtracted from the respective bioluminescence value for each animal.

On day 14, mice were randomized and treated by intraperitoneal administration of 16 mg/kg IMAB027-DM1 or IMAB027-vcMMAE, respectively. Control animals received vehicle buffer. Tumor growth was monitored weekly by bioluminescence imaging from ventral views and subsequent analysis of total flux (photons/sec) in regions of interest covering the abdomen of the mouse.

Endocytosis:

The endocytosis of CLDN6 bound antibody was determined using a cytotoxicity based endocytosis assay that relies on the co-internalization of the target bound antibody and a saporin-conjugated anti-human IgG Fab fragment (Fab-ZAP human, Advanced Targeting Systems, IT-51). Saporin is a ribosome-inactivating protein which upon internalization inhibits protein biosynthesis and therefore results in cell death.

PA-1 cells were harvested with 0.05% Trypsin/EDTA (Gibco, 25300-054) and $2.5 \times 10^3$ cells/well were seeded in 50 µl growth medium in a 96-well culture plate. After 24 h, Fab-ZAP and subsequently IMAB027 or isotype control antibody in a volume of 25 µl each were added. CLDN6 antibodies were administered in a 6 or 8 step dilution series while constant concentrations of Fab-ZAP were applied (Fab-ZAP:Antibody ratio 3:1 to 6561:1). Cells were cultured for additional 72 h in a 37° C. humidified $CO_2$ incubator. Afterwards, cell viability was analyzed using the Cell Proliferation Kit II from AppliChem (AppliChem, A8088-1000) according to the manufacturer's instructions. The absorbance was measured using a spectrophotometer (Tecan) at 480 nm (reference 630 nm).

The invention claimed is:

1. A method of treating cancer comprising:
administering to a cancer patient identified as having ovarian cancer characterized by chemoresistant cancer cells expressing CLDN6 an antibody drug conjugate that binds to CLDN6, wherein the antibody drug conjugate comprises a heavy chain variable region (VH) of SEQ ID NO: 5 and a light chain variable region (VL) of SEQ ID NO: 4 and at least one toxin drug moiety that targets microtubules selected from N2'-deacetyl-N2'(3-mercapto-1-oxopropyl)-maytansine (mertansine or DM1) and monomethyl auristatin E (MMAE).

2. The method of claim 1 wherein the antibody drug conjugate comprises a cleavable linker between the antibody and the at least one toxin drug moiety.

3. The method of claim 1 further comprising administering radiation therapy.

4. The method of claim 2 wherein the cleavable linker is cleavable by a cathepsin.

5. A method of treating a cancer patient having a chemoresistant cancer selected from the group consisting of ovarian cancer, testicular cancer, uterine cancer, germ cell tumors, gastric cancer, and metastatic forms thereof, the method comprising administering to the cancer patient, an antibody drug conjugate that binds to CLDN6, wherein the antibody drug conjugate comprises a heavy chain variable region (VH) of SEQ ID NO: 5 and a light chain variable region (VL) of SEQ ID NO: 4 and at least one toxin drug moiety that targets microtubules selected from N2'-deacetyl-N2'(3-mercapto-1-oxopropyl)-maytansine (mertansine or DM1) and monomethyl auristatin E (MMAE), wherein the cancer is characterized by cancer cells expressing CLDN6.

6. The method of claim 5 which further comprises administering radiation therapy.

7. The method of claim 5 wherein the antibody drug conjugate comprises a cleavable linker between the antibody and the at least one toxin drug moiety.

8. The method of claim 7 wherein the cleavable linker is cleavable by a cathepsin.

9. The method of claim 5 wherein,
when the cancer is a germ cell tumor, the germ cell tumor is selected from the group consisting of teratocarcinoma, embryonal carcinoma, tumors of the testis, and tumors of the ovary; and
when the cancer is testicular cancer, the testicular cancer is selected from the group consisting of testicular seminoma, testicular teratoma and testicular embryonal carcinoma.

10. The method of claim 5, wherein the cancer is ovarian cancer.

* * * * *